(12) United States Patent
Li et al.

(10) Patent No.: US 8,247,184 B2
(45) Date of Patent: *Aug. 21, 2012

(54) ASSAYS USING CHIMERIC T1R POLYPEPTIDES FOR IDENTIFYING PUTATIVE TASTE MODULATORY COMPOUNDS

(75) Inventors: Xiaodong Li, San Diego, CA (US); Feng Zhang, San Diego, CA (US); Hong Xu, San Diego, CA (US); Qing Li, San Diego, CA (US)

(73) Assignee: Senomyx, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/020,068

(22) Filed: Feb. 3, 2011

(65) Prior Publication Data

US 2011/0223618 A1 Sep. 15, 2011

Related U.S. Application Data

(63) Continuation of application No. 11/583,097, filed on Oct. 19, 2006, now Pat. No. 7,906,627, which is a continuation-in-part of application No. 10/569,870, filed as application No. PCT/US2004/025459 on Aug. 6, 2004, now abandoned.

(60) Provisional application No. 60/728,324, filed on Oct. 20, 2005, provisional application No. 60/494,071, filed on Aug. 6, 2003, provisional application No. 60/552,064, filed on Mar. 9, 2004.

(51) Int. Cl.
*G01N 33/53* (2006.01)
*G01N 33/567* (2006.01)
*C12N 1/00* (2006.01)
*C12N 5/07* (2010.01)
*C12N 5/10* (2006.01)

(52) U.S. Cl. ...... 435/7.1; 435/7.2; 435/7.21; 435/254.2; 435/348; 435/349

(58) Field of Classification Search ........................ None
See application file for complete search history.

(56) References Cited

U.S. PATENT DOCUMENTS

2004/0175793 A1 9/2004 Zoller et al.

FOREIGN PATENT DOCUMENTS

WO 2005/015158 2/2005

OTHER PUBLICATIONS

Hiroaki Matsunami et al., Taste Perception: How to Make a Gourmet Mouse, Current Biology, Feb. 3, 2002, vol. 14, (3 pages).
H. Xu et al., PNAS 101(390): 14258-14263, Sep. 28, 2004.

*Primary Examiner* — Robert Landsman
(74) *Attorney, Agent, or Firm* — Hunton & Williams LLP

(57) ABSTRACT

This invention relates to chimeric taste receptors comprising the extracellular portion of one T1R or a variant or fragment thereof, either T1R1 or T1R2, and the transmembrane portion of another T1R or a variant or fragment thereof, either T1R1 or T1R2, preferably associated with a T1R3 polypeptide and a suitable G protein. These chimeric taste receptors and cells which express such chimeric taste receptors are useful in assays for identifying sweet and umami ligands as well in assays for identifying sweet and umami enhancers. Additionally, these chimeric taste receptors and cells which express same can be used to map and determine where specific sweet and umami ligands interact with their respective receptors and to elucidate the mechanism of receptor activation.

37 Claims, 21 Drawing Sheets

FIGURE 1
hT1R2-1 nucleotide sequence

ATGGGGCCCAGGGCAAAGACCATCTGCTCCCTGTTCTTCCTCCTATGGGTCCTGGCT
GAGCCGGCTGAGAACTCGGACTTCTACCTGCCTGGGGATTACCTCCTGGGTGGCCTC
TTCTCCCTCCATGCCAACATGAAGGGCATTGTTCACCTTAACTTCCTGCAGGTGCCCA
TGTGCAAGGAGTATGAAGTGAAGGTGATAGGCTACAACCTCATGCAGGCCATGCGCT
TCGCGGTGGAGGAGATCAACAATGACAGCAGCCTGCTGCCTGGTGTGCTGCTGGGCT
ATGAGATCGTGGATGTGTGCTACATCTCCAACAATGTCCAGCCGGTGCTCTACTTCCT
GGCACACGAGGACAACCTCCTTCCCATCCAAGAGGACTACAGTAACTACATTTCCCGT
GTGGTGGCTGTCATTGGCCCTGACAACTCCGAGTCTGTCATGACTGTGGCCAACTTC
CTCTCCCTATTTCTCCTTCCACAGATCACCTACAGCGCCATCAGCGATGAGCTGCGAG
ACAAGGTGCGCTTCCCGGCTTTGCTGCGTACCACACCCAGCGCCGACCACCACGTCG
AGGCCATGGTGCAGCTGATGCTGCACTTCCGCTGGAACTGGATCATTGTGCTGGTGA
GCAGCGACACCTATGGCCGCGACAATGGCCAGCTGCTTGGCGAGCGCGTGGCCCGG
CGCGACATCTGCATCGCCTTCCAGGAGACGCTGCCCACACTGCAGCCCAACCAGAAC
ATGACGTCAGAGGAGCGCCAGCGCCTGGTGACCATTGTGGACAAGCTGCAGCAGAGC
ACAGCGCGCGTCGTGGTCGTGTTCTCGCCCGACCTGACCCTGTACCACTTCTTCAATG
AGGTGCTGCGCCAGAACTTCACGGGCGCCGTGTGGATCGCCTCCGAGTCCTGGGCCA
TCGACCCGGTCCTGCACAACCTCACGGAGCTGGGCCACTTGGGCACCTTCCTGGGCA
TCACCATCCAGAGCGTGCCCATCCCGGCTTCAGTGAGTTCCGCGAGTGGGGCCCAC
AGGCTGGGCCGCCACCCCTCAGCAGGACCAGCCAGAGCTATACCTGCAACCAGGAGT
GCGACAACTGCCTGAACGCCACCTTGTCCTTCAACACCATTCTCAGGCTCTCTGGGGA
GCGTGTCGTCTACAGCGTGTACTCTGCGGTCTATGCTGTGGCCCATGCCCTGCACAG
CCTCCTCGGCTGTGACAAAAGCACCTGCACCAAGAGGGTGGTCTACCCCTGGCAGCT
GCTTGAGGAGATCTGGAAGGTCAACTTCACTCTCCTGGACCACCAAATCTTCTTCGAC
CCGCAAGGGGACGTGGCTCTGCACTTGGAGATTGTCCAGTGGCAATGGGACCGGAGC
CAGAATCCCTTCCAGAGCGTCGCCTCCTACTACCCCCTGCAGCGACAGCTGAAGAAC
ATCCAAGACATCTCCTGGCACACCGTCAACAACACGATCCCTATGTCCATGTGTTCCA
AGAGGTGCCAGTCAGGGCAAAAGAAGAAGCCTGTGGGCATCCACGTCTGCTGCTTCG
AGTGCATCGACTGCCTTCCCGGCACCTTCCTCAACCACACTGAAGATGAATATGAATG
CCAGGCCTGCCCCGAATAACGAGTGGTCCTACCAGAGTGAGACCTCCTGCTTCAAGCG
GCAGCTGGTCTTCCTcGAgTTGCGTGAGCACACCTCTTGGGTGCTGCTGGCAGCTAAC
ACGCTGCTGCTGCTGCTGCTGCTTGGGACTGCTGGCCTGTTTGCCTGGCACCTAGAC
ACCCCTGTGGTGAGGTCAGCAGGGGCCGCCTGTGCTTTCTTATGCTGGGCTCCCTG
GCAGCAGGTAGTGGCAGCCTCTATGGCTTCTTTGGGGAACCCACAAGGCCTGCGTGC
TTGCTACGCCAGGCCCTCTTTGCCCTTGGTTTCACCATCTTCCTGTCCTGCCTGACAG
TTCGCTCATTCCAACTAATCATCATCTTCAAGTTTTCCACCAAGGTACCTACATTCTAC
CACGCCTGGGTCCAAAACCACGGTGCTGGCCTGTTTGTGATGATCAGCTCAGCGGCC
CAGCTGCTTATCTGTCTAACTTGGCTGGTGGTGTGGACCCCACTGCCTGCTAGGGAA
TACCAGCGCTTCCCCCATCTGGTGATGCTTGAGTGCACAGAGACCAACTCCCTGGGC
TTCATACTGGCCTTCCTCTACAATGGCCTCCTCTCCATCAGTGCCTTTGCCTGCAGCT
ACCTGGGTAAGGACTTGCCAGAGAACTACAACGAGGCCAAATGTGTCACCTTCAGCC
TGCTCTTCAACTTCGTGTCCTGGATCGCCTTCTTCACCACGGCCAGCGTCTACGACGG
CAAGTACCTGCCTGCGGCCAACATGATGGCTGGGCTGAGCAGCCTGAGCAGCGGCTT
CGGTGGGTATTTTCTGCCTAAGTGCTACGTGATCCTCTGCCGCCCAGACCTCAACAGC
ACAGAGCACTTCCAGGCCTCCATTCAGGACTACACGAGGCGCTGCGGCTCCACCTGA

FIGURE 2
hT1R2-1 protein sequence
MGPRAKTICSLFFLLWVLAEPAENSDFYLPGDYLLGGLFSLHANMKGIVHLNFLQVPM
CKEYEVKVIGYNLMQAMRFAVEEINNDSSLLPGVLLGYEIVDVCYISNNVQPVLYFLAH
EDNLLPIQEDYSNYISRVVAVIGPDNSESVMTVANFLSLFLLPQITYSAISDELRDKVRF
PALLRTTPSADHHVEAMVQLMLHFRWNWIIVLVSSDTYGRDNGQLLGERVARRDICIA
FQETLPTLQPNQNMTSEERQRLVTIVDKLQQSTARVVVVFSPDLTLYHFFNEVLRQNF
TGAVWIASESWAIDPVLHNLTELGHLGTFLGITIQSVPIPGFSEFREWGPQAGPPPLSRT
SQSYTCNQECDNCLNATLSFNTILRLSGERVVYSVYSAVYAVAHALHSLLGCDKSTCTK
RVVYPWQLLEEIWKVNFTLLDHQIFFDPQGDVALHLEIVQWQWDRSQNPFQSVASYY
PLQRQLKNIQDISWHTVNNTIPMSMCSKRCQSGQKKKPVGIHVCCFECIDCLPGTFLN
HTEDEYECQACPNNEWSYQSETSCFKRQLVFLELREHTSWVLLAANTLLLLLLGTAG
LFAWHLDTPVVRSAGGRLCFLMLGSLAAGSGSLYGFFGEPTRPACLLRQALFALGFTIF
LSCLTVRSFQLIIIFKFSTKVPTFYHAWVQNHGAGLFVMISSAAQLLICLTWLVVWTPLP
AREYQRFPHLVMLECTETNSLGFILAFLYNGLLSISAFACSYLGKDLPENYNEAKCVTF
SLLFNFVSWIAFFTTASVYDGKYLPAANMMAGLSSLSSGFGGYFLPKCYVILCRPDLNS
TEHFQASIQDYTRRCGST

FIGURE 3
hT1R1-2 nucleotide sequence

```
ATGCTGCTCTGCACGGCTCGCCTGGTCGGCCTGCAGCTTCTCATTTCCTG
CTGCTGGGCCTTTGCCTGCCATAGCACGGAGTCTTCTCCTGACTTCACCC
TCCCCGGAGATTACCTCCTGGCAGGCCTGTTCCCTCTCCATTCTGGCTGT
CTGCAGGTGAGGCACAGACCCGAGGTGACCCTGTGTGACAGGTCTTGTAG
CTTCAATGAGCATGGCTACCACCTCTTCCAGGCTATGCGGCTTGGGGTTG
AGGAGATAAACAACTCCACGGCCCTGCTGCCCAACATCACCCTGGGGTAC
CAGCTGTATGATGTGTGTTCTGACTCTGCCAATGTGTATGCCACGCTGAG
AGTGCTCTCCCTGCCAGGGCAACACCACATAGAGCTCCAAGGAGACCTTC
TCCACTATTCCCCTACGGTGCTGGCAGTGATTGGGCCTGACAGCACCAAC
CGTGCTGCCACCACAGCCGCCCTGCTGAGCCCTTTCCTGGTGCCCATGAT
TAGCTATGCGGCCAGCAGCGAGACGCTCAGCGTGAAGCGGCAGTATCCCT
CTTTCCTGCGCACCATCCCCAATGACAAGTACCAGGTGGAGACCATGGTG
CTGCTGCTGCAGAAGTTCGGGTGGACCTGGATCTCTCTGGTTGGCAGCAG
TGACGACTATGGGCAGCTAGGGGTGCAGGCACTGGAGAACCAGGCCACTG
GTCAGGGGATCTGCATTGCTTTCAAGGACATCATGCCCTTCTCTGCCCAG
GTGGGCGATGAGAGGATGCAGTGCCTCATGCGCCACCTGGCCCAGGCCGG
GGCCACCGTCGTGGTTGTTTTTTCCAGCCGGCAGTTGGCCAGGGTGTTTT
TCGAGTCCGTGGTGCTGACCAACCTGACTGGCAAGGTGTGGGTCGCCTCA
GAAGCCTGGGCCCTCTCCAGGCACATCACTGGGGTGCCCGGGATCCAGCG
CATTGGGATGGTGCTGGGCGTGGCCATCCAGAAGAGGGCTGTCCCTGGCC
TGAAGGCGTTTGAAGAAGCCTATGCCCGGGCAGACAAGAAGGCCCCTAGG
CCTTGCCACAAGGGCTCCTGGTGCAGCAGCAATCAGCTCTGCAGAGAATG
CCAAGCTTTCATGGCACACACGATGCCCAAGCTCAAAGCCTTCTCCATGA
GTTCTGCCTACAACGCATACCGGGCTGTGTATGCGGTGGCCCATGGCCTC
CACCAGCTCCTGGGCTGTGCCTCTGGAGCTTGTTCCAGGGGCCGAGTCTA
CCCCTGGCAGCTTTTGGAGCAGATCCACAAGGTGCATTTCCTTCTACACA
AGGACACTGTGGCGTTTAATGACAACAGAGATCCCCTCAGTAGCTATAAC
ATAATTGCCTGGGACTGGAATGGACCCAAGTGGACCTTCACGGTCCTCGG
TTCCTCCACATGGTCTCCAGTTCAGCTAAACATAAATGAGACCAAAATCC
AGTGGCACGGAAAGGACAACCAGGTGCCTAAGTCTGTGTGTTCCAGCGAC
TGTCTTGAAGGGCACCAGCGAGTGGTTACGGGTTTCCATCACTGCTGCTT
TGAGTGTGTGCCCTGTGGGGCTGGGACCTTCCTCAACAAGAGTGACCTCT
ACAGATGCCAGCCTTGTGGGAAAGAAGAGTGGGCACCTGAGGGAAGCCAG
ACCTGCTTCCCGCGCACTGTGGTGTTTCTCGAGTGGCATGAGGCACCCAC
CATCGCTGTGGCCCTGCTGGCCGCCCTGGGCTTCCTCAGCACCCTGGCCA
TCCTGGTGATATTCTGGAGGCACTTCCAGACACCCATAGTTCGCTCGGCT
GGGGGCCCCATGTGCTTCCTGATGCTGACACTGCTGCTGGTGGCATACAT
GGTGGTCCCGGTGTACGTGGGGCCGCCCAAGGTCTCCACCTGCCTCTGCC
GCCAGGCCCTCTTTCCCCTCTGCTTCACAATTTGCATCTCCTGTATCGCC
GTGCGTTCTTTCCAGATCGTCTGCGCCTTCAAGATGGCCAGCCGCTTCCC
ACGCGCCTACAGCTACTGGGTCCGCTACCAGGGGCCCTACGTCTCTATGG
CATTTATCACGGTACTCAAAATGGTCATTGTGGTAATTGGCATGCTGGCC
ACGGGCCTCAGTCCCACCACCCGTACTGACCCCGATGACCCCAAGATCAC
AATTGTCTCCTGTAACCCCAACTACCGCAACAGCCTGCTGTTCAACACCA
GCCTGGACCTGCTGCTCTCAGTGGTGGGTTTCAGCTTCGCCTACATGGGC
AAAGAGCTGCCCACCAACTACAACGAGGCCAAGTTCATCACCCTCAGCAT
GACCTTCTATTTCACCTCATCCGTCTCCCTCTGCACCTTCATGTCTGCCT
ACAGCGGGGTGCTGGTCACCATCGTGGACCTCTTGGTCACTGTGCTCAAC
CTCCTGGCCATCAGCCTGGGCTACTTCGGCCCCAAGTGCTACATGATCCT
CTTCTACCCGGAGCGCAACACGCCCGCCTACTTCAACAGCATGATCCAGG
GCTACACCATGAGGAGGGACTAG
```

FIGURE 4
hT1R1-2 Protein Sequence

MLLCTARLVGLQLLISCCWAFACHSTESSPDFTLPGDYLLAGLFPLHSGC
LQVRHRPEVTLCDRSCSFNEHGYHLFQAMRLGVEEINNSTALLPNITLGY
QLYDVCSDSANVYATLRVLSLPGQHHIELQGDLLHYSPTVLAVIGPDSTN
RAATTAALLSPFLVPMISYAASSETLSVKRQYPSFLRTIPNDKYQVETMV
LLLQKFGWTWISLVGSSDDYGQLGVQALENQATGQGICIAFKDIMPFSAQ
VGDERMQCLMRHLAQAGATVVVVFSSRQLARVFFESVVLTNLTGKVWVAS
EAWALSRHITGVPGIQRIGMVLGVAIQKRAVPGLKAFEEAYARADKKAPR
PCHKGSWCSSNQLCRECQAFMAHTMPKLKAFSMSSAYNAYRAVYAVAHGL
HQLLGCASGACSRGRVYPWQLLEQIHKVHFLLHKDTVAFNDNRDPLSSYN
IIAWDWNGPKWTFTVLGSSTWSPVQLNINETKIQWHGKDNQVPKSVCSSD
CLEGHQRVVTGFHHCCFECVPCGAGTFLNKSDLYRCQPCGKEEWAPEGSQ
TCFPRTVVFLEWHEAPTIAVALLAALGFLSTLAILVIFWRHFQTPIVRSAG
GPMCFLMLTLLLVAYMVVPVYVGPPKVSTCLCRQALFPLCFTICISCIAV
RSFQIVCAFKMASRFPRAYSYWVRYQGPYVSMAFITVLKMVIVVIGMLAT
GLSPTTRTDPDDPKITIVSCNPNYRNSLLFNTSLDLLLSVVGFSFAYMGK
ELPTNYNEAKFITLSMTFYFTSSVSLCTFMSAYSGVLVTIVDLLVTVLNL
LAISLGYFGPKCYMILFYPERNTPAYFNSMIQGYTMRRD

G16gust44 Protein Sequence:

MARSLTWRCCPWCLTEDEKAAARVDQEINRILLEQKKQDRGELKLLLLGPGESGKSTFIKQMRIIHGAGYSEEERKGFRPLVYQN
IFVSMRAMIEAMERLQIPFSRPESKHHASLVMSQDPYKVTTFEKRYAAAMQWLWRDAGIRACYERRREFHLLDSAVYYLSHLERI
TEEGYVPTAQDVLRSRMPTTGINEYCFSVQKTNLRIVDVGGQKSERKKWIHCFENVIALIYLASLSEYDQCLEENNQENRMKESL
ALFGTILELPWFKSTSVILFLNKTDILEEKIPTSHLATYFPSFQGPKQDAEAAKRFILDMYTRMYTGCVDGPEGSNLKKEDKEIY
SHMTCATDTQNVKFVPDAVTDIIIKENLKDCGLF

Schematics of the sweet, umami, and sweet-umami chimeric receptors

Figure 6

T1R sequences:
hT1R1 cDNA
```
ATGCTGCTCTGCACGGCTCGCCTGGTCGGCCTGCAGCTTCTCATTTCCTGCTGCTGGGCCTTTGCCTGCCA
TAGCACGGAGTCTTCTCCTGACTTCACCCTCCCCGGAGATTACCTCCTGGCAGGCCTGTTCCCTCTCCATT
CTGGCTGTCTGCAGGTGAGGCACAGACCCGAGGTGACCCTGTGTGACAGGTCTTGTAGCTTCAATGAGCAT
GGCTACCACCTCTTCCAGGCTATGCGGCTTGGGGTTGAGGAGATAAACAACTCCACGGCCCTGCTGCCCAA
CATCACCCTGGGGTACCAGCTGTATGATGTGTGTTCTGACTCTGCCAATGTGTATGCCACGCTGAGAGTGC
TCTCCCTGCCAGGGCAACACCACATAGAGCTCCAAGGAGACCTTCTCCACTATTCCCCTACGGTGCTGGCA
GTGATTGGGCCTGACAGCACCAACCGTGCTGCCACCACAGCCGCCCTGCTGAGCCCTTTCCTGGTGCCCAT
GATTAGCTATGCGGCCAGCAGCGAGACGCTCAGCGTGAAGCGGCAGTATCCCTCTTTCCTGCGCACCATCC
CCAATGACAAGTACCAGGTGGAGACCATGGTGCTGCTGCTGCAGAAGTTCGGGTGGACCTGGATCTCTCTG
GTTGGCAGCAGTGACGACTATGGGCAGCTAGGGGTGCAGGCACTGGAGAACCAGGCCACTGGTCAGGGGAT
CTGCATTGCTTTCAAGGACATCATGCCCTTCTCTGCCCAGGTGGGCGATGAGAGGATGCAGTGCCTCATGC
GCCACCTGGCCCAGGCCGGGGCCACCGTCGTGGTTGTTTTTTCCAGCCGGCAGTTGGCCAGGGTGTTTTTC
GAGTCCGTGGTGCTGACCAACCTGACTGGCAAGGTGTGGGTCGCCTCAGAAGCCTGGGCCCTCTCCAGGCA
CATCACTGGGGTGCCCGGGATCCAGCGCATTGGGATGGTGCTGGGCGTGGCCATCCAGAAGAGGGCTGTCC
CTGGCCTGAAGGCGTTTGAAGAAGCCTATGCCCGGGCAGACAAGAAGGCCCCTAGGCCTTGCCACAAGGGC
TCCTGGTGCAGCAGCAATCAGCTCTGCAGAGAATGCCAAGCTTTCATGGCACACACGATGCCCAAGCTCAA
AGCCTTCTCCATGAGTTCTGCCTACAACGCATACCGGGCTGTGTATGCGGTGGCCCATGGCCTCCACCAGC
TCCTGGGCTGTGCCTCTGGAGCTTGTTCCAGGGGCCGAGTCTACCCCTGGCAGCTTTTGGAGCAGATCCAC
AAGGTGCATTTCCTTCTACACAAGGACACTGTGGCGTTTAATGACAACAGAGATCCCCTCAGTAGCTATAA
CATAATTGCCTGGGACTGGAATGGACCCAAGTGGACCTTCACGGTCCTCGGTTCCTCCACATGGTCTCCAG
TTCAGCTAAACATAAATGAGACCAAAATCCAGTGGCACGGAAAGGACAACCAGGTGCCTAAGTCTGTGTGT
TCCAGCGACTGTCTTGAAGGGCACCAGCGAGTGGTTACGGGTTTCCATCACTGCTGCTTTGAGTGTGTGCC
CTGTGGGGCTGGGACCTTCCTCAACAAGAGTGACCTCTACAGATGCCAGCCTTGTGGGAAAGAAGAGTGGG
CACCTGAGGGAAGCCAGACCTGCTTCCCGCGCACTGTGGTGTTTTTGGCTTTGCCTGAGCACACCTCTTGG
GTGCTGCTGGCAGCTAACACGCTGCTGCTGCTGCTGCTTGGGACTGCTGGCCTGTTTGCCTGGCACCT
AGACACCCCTGTGGTGAGGTCAGCAGGGGGCCGCCTGTGCTTTCTTATGCTGGGCTCCCTGGCAGCAGGTA
GTGGCAGCCTCTATGGCTTCTTTGGGGAACCCACAAGGCCTGCGTGCTTGCTACGCCAGGCCCTCTTTGCC
CTTGGTTTCACCATCTTCCTGTCCTGCCTGACAGTTCGCTCATTCCAACTAATCATCATCTTCAAGTTTTC
CACCAAGGTACCTACATTCTACCACGCCTGGGTCCAAAACCACGGTGCTGGCCTGTTTGTGATGATCAGCT
CAGCGGCCCAGCTGCTTATCTGTCTAACTTGGCTGGTGGTGTGGACCCCACTGCCTGCTAGGGAATACCAG
CGCTTCCCCCATCTGGTGATGCTTGAGTGCACAGAGACCAACTCCCTGGGCTTCATACTGGCCTTCCTCTA
CAATGGCCTCCTCTCCATCAGTGCCTTTGCCTGCAGCTACCTGGGTAAGGACTTGCCAGAGAACTACAACG
AGGCCAAATGTGTCACCTTCAGCCTGCTCTTCAACTTCGTGTCCTGGATCGCCTTCTTCACCACGGCCAGC
GTCTACGACGGCAAGTACCTGCCTGCGGCCAACATGATGGCTGGGCTGAGCAGCCTGAGCAGCGGCTTCGG
TGGGTATTTTCTGCCTAAGTGCTACGTGATCCTCTGCCGCCCAGACCTCAACAGCACAGAGCACTTCCAGG
CCTCCATTCAGGACTACACGAGGCGCTGCGGCTCCACCTGA
```
(SEQ ID NO:6)

hT1R1 protein
```
MLLCTARLVGLQLLISCCWAFACHSTESSPDFTLPGDYLLAGLFPLHSGCLQVRHRPEVTLCDRSCSFNEH
GYHLFQAMRLGVEEINNSTALLPNITLGYQLYDVCSDSANVYATLRVLSLPGQHHIELQGDLLHYSPTVLA
VIGPDSTNRAATTAALLSPFLVPMISYAASSETLSVKRQYPSFLRTIPNDKYQVETMVLLLQKFGWTWISL
VGSSDDYGQLGVQALENQATGQGICIAFKDIMPFSAQVGDERMQCLMRHLAQAGATVVVVFSSRQLARVFF
ESVVLTNLTGKVWVASEAWALSRHITGVPGIQRIGMVLGVAIQKRAVPGLKAFEEAYARADKKAPRPCHKG
SWCSSNQLCRECQAFMAHTMPKLKAFSMSSAYNAYRAVYAVAHGLHQLLGCASGACSRGRVYPWQLLEQIH
KVHFLLHKDTVAFNDNRDPLSSYNIIAWDWNGPKWTFTVLGSSTWSPVQLNINETKIQWHGKDNQVPKSVC
SSDCLEGHQRVVTGFHHCCFECVPCGAGTFLNKSDLYRCQPCGKEEWAPEGSQTCFPRTVVFLALREHTSW
VLLAANTLLLLLLLGTAGLFAWHLDTPVVRSAGGRLCFLMLGSLAAGSGSLYGFFGEPTRPACLLRQALFA
LGFTIFLSCLTVRSFQLIIIFKFSTKVPTFYHAWVQNHGAGLFVMISSAAQLLICLTWLVVWTPLPAREYQ
RFPHLVMLECTETNSLGFILAFLYNGLLSISAFACSYLGKDLPENYNEAKCVTFSLLFNFVSWIAFFTTAS
VYDGKYLPAANMMAGLSSLSSGFGGYFLPKCYVILCRPDLNSTEHFQASIQDYTRRCGST
```
(SEQ ID NO:7)

Figure 6 (continued)

rT1R1 cDNA
ATGCTCTTCTGGGCTGCTCACCTGCTGCTCAGCCTGCAGTTGGTCTACTGCTGGGCTTTCAGCTGCCAAA
GGACAGAGTCCTCTCCAGGCTTCAGCCTTCCTGGGGACTTCCTCCTTGCAGGTCTGTTCTCCCTCCATGGT
GACTGTCTGCAGGTGAGACACAGACCTCTGGTGACAAGTTGTGACAGGCCCGACAGCTTCAACGGCCATGG
CTACCACCTCTTCCAAGCCATGCGGTTCACTGTTGAGGAGATAAACAACTCCTCGGCCCTCCTTCCCAACA
TCACCCTGGGGTATGAGCTGTACGACGTGTGCTCAGAATCTGCCAATGTGTATGCCACCCTGAGGGTGCTT
GCCCTGCAAGGGCCCCGCCACATAGAGATACAGAAAGACCTTCGCAACCACTCCTCCAAGGTGGTGGCCTT
CATCGGGCCTGACAACACTGACCACGCTGTCACTACCGCTGCCTTGCTGGGTCCTTTCCTGATGCCCCTGG
TCAGCTATGAGGCAAGCAGCGTGGTACTCAGTGCCAAGCGCAAGTTCCCGTCTTTCCTTCGTACCGTCCCC
AGTGACCGGCACCAGGTGGAGGTCATGGTGCAGCTGCTGCAGAGTTTTGGGTGGGTGTGGATCTCGCTCAT
TGGCAGCTACGGTGATTACGGGCAGCTGGGTGTGCAGGCGCTGGAGGAGCTGGCCGTGCCCCGGGGCATCT
GCGTCGCCTTCAAGGACATCGTGCCTTTCTCTGCCCGGGTGGGTGACCCGAGGATGCAGAGCATGATGCAG
CATCTGGCTCAGGCCAGGACCACCGTGGTTGTGGTCTTCTCTAACCGGCACCTGGCTAGAGTGTTCTTCAG
GTCCGTGGTGCTGGCCAACCTGACTGGCAAAGTGTGGGTCGCCTCAGAAGACTGGGCCATCTCCACGTACA
TCACCAGCGTGACTGGGATCCAAGGCATTGGGACGGTGCTCGGTGTGGCCGTCCAGCAGAGACAAGTCCCT
GGGCTGAAGGAGTTTGAGGAGTCTTATGTCAGGGCTGTAACAGCTGCTCCCAGCGCTTGCCCGGAGGGGTC
CTGGTGCAGCACTAACCAGCTGTGCCGGGAGTGCCACACGTTCACGACTCGTAACATGCCCACGCTTGGAG
CCTTCTCCATGAGTGCCGCCTACAGAGTGTATGAGGCTGTGTACGCTGTGGCCCACGGCCTCCACCAGCTC
CTGGGATGTACTTCTGAGATCTGTTCCAGAGGCCCAGTCTACCCCTGGCAGCTTCTTCAGCAGATCTACAA
GGTGAATTTTCTTCTACATGAGAATACTGTGGCATTTGATGACAACGGGGACACTCTAGGTTACTACGACA
TCATCGCCTGGGACTGGAATGGACCTGAATGGACCTTTGAGATCATTGGCTCTGCCTCACTGTCTCCAGTT
CATCTGGACATAAATAAGACAAAAATCCAGTGGCACGGCAAGAACAATCAGGTGCCTGTGTCAGTGTGTAC
CACGGACTGTCTGGCAGGGCACCACAGGGTGGTTGTGGGTTCCCACCACTGCTGCTTTGAGTGTGTGCCCT
GCGAAGCTGGGACCTTTCTCAACATGAGTGAGCTTCACATCTGCCAGCCTTGTGGAACAGAAGAATGGGCA
CCCAAGGAGAGCACTACTTGCTTCCCACGCACGGTGGAGTTCTTGGCTTGGCATGAACCCATCTCTTTGGT
GCTAATAGCAGCTAACACGCTATTGCTGCTGCTGCTGGTTGGGACTGCTGGCCTGTTTGCCTGGCATTTTC
ACACACCTGTAGTGAGGTCAGCTGGGGGTAGGCTGTGCTTCCTCATGCTGGGTTCCCTGGTGGCCGGAAGT
TGCAGCTTCTATAGCTTCTTCGGGGAGCCCACGGTGCCCGCGTGCTTGCTGCGTCAGCCCCTCTTTTCTCT
CGGGTTTGCCATCTTCCTCTCCTGCCTGACAATCCGCTCCTTCCAACTGGTCATCATCTTCAAGTTTTCTA
CCAAGGTGCCCACATTCTACCGTACCTGGGCCCAAAACCATGGTGCAGGTCTATTCGTCATTGTCAGCTCC
ACGGTCCATTTGCTCATCTGTCTCACATGGCTTGTAATGTGGACCCCACGACCCACCAGGGAATACCAGCG
CTTCCCCCATCTGGTGATTCTCGAGTGCACAGAGGTCAACTCTGTAGGCTTCCTGTTGGCTTTCACCCACA
ACATTCTCCTCTCCATCAGTACCTTCGTCTGCAGCTACCTGGGTAAGGAACTGCCAGAGAACTATAATGAA
GCCAAATGTGTCACCTTCAGCCTGCTCCTCAACTTCGTATCCTGGATCGCCTTCTTCACCATGGCCAGCAT
TTACCAGGGCAGCTACCTGCCTGCGGTCAATGTGCTGGCAGGGCTGACCACACTGAGCGGCGGCTTCAGCG
GTTACTTCCTCCCCAAGTGCTATGTGATTCTCTGCCGTCCAGAACTCAACAATACAGAACACTTTCAGGCC
TCCATCCAGGACTACACGAGGCGCTGCGGCACTACCTGA
(SEQ ID NO:8)

rT1R1 protein
MLFWAAHLLLSLQLVYCWAFSCQRTESSPGFSLPGDFLLAGLFSLHGDCLQVRHRPLVTSCDRPDSFNGHG
YHLFQAMRFTVEEINNSSALLPNITLGYELYDVCSESANVYATLRVLALQGPRHIEIQKDLRNHSSKVVAF
IGPDNTDHAVTTAALLGPFLMPLVSYEASSVVLSAKRKFPSFLRTVPSDRHQVEVMVQLLQSFGWVWISLI
GSYGDYGQLGVQALEELAVPRGICVAFKDIVPFSARVGDPRMQSMMQHLAQARTTVVVFSNRHLARVFFR
SVVLANLTGKVWVASEDWAISTYITSVTGIQGIGTVLGVAVQQRQVPGLKEFEESYVRAVTAAPSACPEGS
WCSTNQLCRECHTFTTRNMPTLGAFSMSAAYRVYEAVYAVAHGLHQLLGCTSEICSRGPVYPWQLLQQIYK
VNFLLHENTVAFDDNGDTLGYYDIIAWDWNGPEWTFEIIGSASLSPVHLDINKTKIQWHGKNNQVPVSVCT
TDCLAGHHRVVVGSHHCCFECVPCEAGTFLNMSELHICQPCGTEEWAPKESTTCFPRTVEFLAWHEPISLV
LIAANTLLLLLLVGTAGLFAWHFHTPVVRSAGGRLCFLMGSLVAGSCSFYSFFGEPTVPACLLRQPLFSL
GFAIFLSCLTIRSFQLVIIFKPSTKVPTFYRTWAQNHGAGLFVIVSSTVHLLICLTWLVMWTPRPTREYQR
FPHLVILECTEVNSVGPLLAFTHNILLSISTFVCSYLGKELPENYNEAKCVTFSLLLNFVSWIAFFTMASI
YQGSYLPAVNVLAGLTTLSGGFSGYFLPKCYVILCRPELNNTEHFQASIQDYTRRCGTT
(SEQ ID NO:9)

hT1R2 cDNA
ATGGGGCCCAGGGCAAAGACCATCTGCTCCCTGTTCTTCCTCCTATGGGTCCTGGCTGAGCCGGCTGAGAA
CTCGGACTTCTACCTGCCTGGGGATTACCTCCTGGGTGGCCTCTTCTCCCTCCATGCCAACATGAAGGGCA

Figure 6 (continued)

```
TTGTTCACCTTAACTTCCTGCAGGTGCCCATGTGCAAGGAGTATGAAGTGAAGGTGATAGGCTACAACCTC
ATGCAGGCCATGCGCTTCGCGGTGGAGGAGATCAACAATGACAGCAGCCTGCTGCCTGGTGTGCTGCTGGG
CTATGAGATCGTGGATGTGTGCTACATCTCCAACAATGTCCAGCCGGTGCTCTACTTCCTGGCACACGAGG
ACAACCTCCTTCCCATCCAAGAGGACTACAGTAACTACATTTCCCGTGTGGTGGCTGTCATTGGCCCTGAC
AACTCCGAGTCTGTCATGACTGTGGCCAACTTCCTCTCCCTATTTCTCCTTCCACAGATCACCTACAGCGC
CATCAGCGATGAGCTGCGAGACAAGGTGCGCTTCCCGGCTTTGCTGCGTACCACACCCAGCGCCGACCACC
ACGTCGAGGCCATGGTGCAGCTGATGCTGCACTTCCGCTGGAACTGGATCATTGTGCTGGTGAGCAGCGAC
ACCTATGGCCGCGACAATGGCCAGCTGCTTGGCGAGCGGGTGGCCCGGCGCGACATCTGCATCGCCTTCCA
GGAGACGCTGCCCACACTGCAGCCCAACCAGAACATGACGTCAGAGGAGCGCCAGCGCCTGGTGACCATTG
TGGACAAGCTGCAGCAGAGCACAGCGCGCGTCGTGGTCGTGTTCTCGCCCGACCTGACCCTGTACCACTTC
TTCAATGAGGTGCTGCGCCAGAACTTCACGGGCGCCGTGTGGATCGCCTCCGAGTCCTGGGCCATCGACCC
GGTCCTGCACAACCTCACGGAGCTGGGCCACTTGGGCACCTTCCTGGGCATCACCATCCAGAGCGTGCCCA
TCCCGGGCTTCAGTGAGTTCCGCGAGTGGGGCCCACAGGCTGGGCCGCCACCCCTCAGCAGGACCAGCCAG
AGCTATACCTGCAACCAGGAGTGCGACAACTGCCTGAACGCCACCTTGTCCTTCAACACCATTCTCAGGCT
CTCTGGGGAGCGTGTCGTCTACAGCGTGTACTCTGCGGTCTATGCTGTGGCCCATGCCCTGCACAGCCTCC
TCGGCTGTGACAAAAGCACCTGCACCAAGAGGGTGGTCTACCCCTGGCAGCTGCTTGAGGAGATCTGGAAG
GTCAACTTCACTCTCCTGGACCACCAAATCTTCTTCGACCCGCAAGGGGACGTGGCTCTGCACTTGGAGAT
TGTCCAGTGGCAATGGGACCGGAGCCAGAATCCCTTCCAGAGCGTCGCCTCCTACTACCCCCTGCAGCGAC
AGCTGAAGAACATCCAAGACATCTCCTGGCACACCGTCAACAACACGATCCCTATGTCCATGTGTTCCAAG
AGGTGCCAGTCAGGGCAAAAGAAGAAGCCTGTGGGCATCCACGTCTGCTGCTTCGAGTGCATCGACTGCCT
TCCCGGCACCTTCCTCAACCACACTGAAGATGAATATGAATGCCAGGCCTGCCCGAATAACGAGTGGTCCT
ACCAGAGTGAGACCTCCTGCTTCAAGCGGCAGCTGGTCTTCCTGGAATGGCATGAGGCACCCACCATCGCT
GTGGCCCTGCTGGCCGCCCTGGGCTTCCTCAGCACCCTGGCCATCCTGGTGATATTCTGGAGGCACTTCCA
GACACCCATAGTTCGCTCGGCTGGGGGCCCCATGTGCTTCCTGATGCTGACACTGCTGCTGGTGGCATACA
TGGTGGTCCCGGTGTACGTGGGGCCGCCCAAGGTCTCCACCTGCCTCTGCCGCCAGGCCCTCTTTCCCCTC
TGCTTCACAATTTGCATCTCCTGTATCGCCGTGCGTTCTTTCCAGATCGTCTGCGCCTTCAAGATGGCCAG
CCGCTTCCCACGCGCCTACAGCTACTGGGTCCGCTACCAGGGCCCTACGTCTCTATGCATTTATCACGG
TACTCAAAATGGTCATTGTGGTAATTGGCATGCTGGCCACGGGCCTCAGTCCCACCACCGTACTGACCCCC
GATGACCCCAAGATCACAATTGTCTCCTGTAACCCCAACTACCGCAACAGCCTGCTGTTCAACACCAGCCT
GGACCTGCTGCTCTCAGTGGTGGGTTTCAGCTTCGCCTACATGGGCAAAGAGCTGCCCACCAACTACAACG
AGGCCAAGTTCATCACCCTCAGCATGACCTTCTATTTCACCTCATCCGTCTCCCTCTGCACCTTCATGTCT
GCCTACAGCGGGGTGCTGGTCACCATCCTGGACCTCTTGGTCACTGTGCTCAACCTCCTGGCCATCAGCCT
GGGCTACTTCGGCCCCAAGTGCTACATGATCCTCTTCTACCCGGAGCGCAACACGCCCGCCTACTTCAACA
GCATGATCCAGGGCTACACCATGAGGAGGGACTAG
(SEQ ID NO:10)
``` hT1R2 protein
```
MGPRAKTICSLFFLLWVLAEPAENSDFYLPGDYLLGGLFSLHANMKGIVHLNFLQVPMCKEYEVKVIGYNL
MQAMRFAVEEINNDSSLLPGVLLGYEIVDVCYISNNVQPVLYFLAHEDNLLPIQEDYSNYISRVVAVIGPD
NSESVMTVANFLSLFLLPQITYSAISDELRDKVRFPALLRTTPSADHHVEAMVQLMLHFRWNWIIVLVSSD
TYGRDNGQLLGERVARRDICIAFQETLPTLQPNQNMTSEERQRLVTIVDKLQQSTARVVVVFSPDLTLYHF
FNEVLRQNFTGAVWIASESWAIDPVLHNLTELGHLGTFLGITIQSVPIPGFSEFREWGPQAGPPPLSRTSQ
SYTCNQECDNCLNATLSFNTILRLSGERVVYSVYSAVYAVAHALHSLLGCDKSTCTKRVVYPWQLLEEIWK
VNFTLLDHQIFFDPQGDVALHLEIVQWQWDRSQNPFQSVASYYPLQRQLKNIQDISWHTVNNTIPMSMCSK
RCQSGQKKKPVGIHVCCFECIDCLPGTFLNHTEDEYECQACPNNEWSYQSETSCFKRQLVFLEWHEAPTIA
VALLAALGFLSTLAILVIFWRHFQTPIVRSAGGPMCFLMLTLLLVAYMVVPVYVGPPKVSTCLCRQALFPL
CFTICISCIAVRSFQIVCAFKMASRFPRAYSYWVRYQGPYVSMAFITVLKMVIVVIGMLATGLSPTTRTDP
DDPKITIVSCNPNYRNSLLFNTSLDLLLSVVGFSFAYMGKELPTNYNEAKFITLSMTFYFTSSVSLCTFMS
AYSGVLVTIVDLLVTVLNLLAISLGYFGPKCYMILFYPERNTPAYFNSMIQGYTMRRD
(SEQ ID NO:11)
``` rT1R2 cDNA
```
ATGGGTCCCCAGGCAAGGACACTCTGCTTGCTGTCTCTCCTGCTGCATGTTCTGCCTAAGCCAGGCAAGCT
GGTAGAGAACTCTGACTTCCACCTGGCCGGGGACTACCTCCTGGGTGGCCTCTTTACCCTCCATGCCAACG
TGAAGAGCATCTCCCACCTCAGCTACCTGCAGGTGCCCAAGTGCAATGAGTTCACCATGAAGGTGTTGGGC
TACAACCTCATGCAGGCCATGCGTTTCGCTGTGGAGGAGATCAACAACTGTAGCTCCCTGCTACCCGGCGT
GCTGCTCGGCTACGAGATGGTGGATGTCTGTTACCTCTCCAACAATATCCACCCTGGGCTCTACTTCCTGG
```

Figure 6 (continued)

```
CACAGGACGACGACCTCCTGCCCATCCTCAAAGACTACAGCCAGTACATGCCCCACGTGGTGGCTGTCATT
GGCCCCGACAACTCTGAGTCCGCCATTACCGTGTCCAACATTCTCTCTCATTTCCTCATCCCACAGATCAC
ATACAGCGCCATCTCCGACAAGCTGCGGGACAAGCGGCACTTCCCTAGCATGCTACGCACAGTGCCCAGCG
CCACCCACCACATCGAGGCCATGGTGCAGCTGATGGTTCACTTCCAATGGAACTGGATTGTGGTGCTGGTG
AGCGACGACGATTACGGCCGCGAGAACAGCCACCTGTTGAGCCAGCGTCTGACCAAAACGAGCGACATCTG
CATTGCCTTCCAGGAGGTTCTGCCCATACCTGAGTCCAGCCAGGTCATGAGGTCCGAGGAGCAGAGACAAC
TGGACAACATCCTGGACAAGCTGCGGCGGACCTCGGCGCGCGTCGTGGTGGTGTTCTCGCCCGAGCTGAGC
CTGTATAGCTTCTTTCACGAGGTGCTCCGCTGGAACTTCACGGGTTTTGTGTGGATCGCCTCTGAGTCCTG
GGCTATCGACCCAGTTCTGCATAACCTCACGGAGCTGCGCCACACGGGTACTTTTCTGGGCGTCACCATCC
AGAGGGTGTCCATCCCTGGCTTCAGTCAGTTCCGAGTGCGCCGTGACAAGCAGGGTATCCCGTGCCTAAC
ACGACCAACCTGCGGACGACCTGCAACCAGGACTGTGACGCCTGCTTGAACACCACCAAGTCCTTCAACAA
CATCCTTATACTTTCGGGGGAGCGCGTGGTCTACAGCGTGTACTCGGCAGTTTACGCGGTGGCCCATGCCC
TCCACAGACTCCTCGGCTGTAACCGGGTCCGCTGCACCAAGCAAAAGGTCTACCCGTGGCAGCTACTCAGG
GAGATCTGGCACGTCAACTTCACGCTCCTGGGTAACCGGCTGCTTCTTTGACCAACAAGGGGACATGCCGAT
GCTCTTGGACATCATCCAGTGGCAGTGGGACCTGAGCCAGAATCCCTTCCAAAGCATCGCCTCCTATTCTC
CCACCAGCAAGAGGCTAACCTACATTAACAATGTGTCCTGGTACACCCCCAACAACACGGTCCCTGTCTCC
ATGTGTTCCAAGAGCTGCCAGCCAGGGCAAATGAAAAAGTCTGTGGGCCTCCACCCTTGTTGCTTCGAGTG
CTTGGATTGTATGCCAGGCACCTACCTCAACCGCTCAGCAGATGAGTTTAACTGTCTGTCCTGCCCGGGTT
CCATGTGGTCCTACAAGAACGACATCACTTGCTTCCAGCGGCGGCCTACCTTCCTGGAGTGGCACGAAGTG
CCCACCATCGTGGTGGCCATACTGGCTGCCCTGGGCTTCTTCAGTACACTGGCCATTCTTTTCATCTTCTG
GAGACATTTCCAGACACCCATGGTGCGCTCGGCCGGTGGCCCCATGTGCTTCCTGATGCTCGTGCCCCTGC
TGCTGGCGTTTGGGATGGTGCCCGTGTATGTGGGCCCCCCACGGTCTTCTCATGCTTCTGCCGACAGGCT
TTCTTCACCGTCTGCTTCTCCATCTGCCTATCCTGCATCACCGTGCGCTCCTTCCAGATCGTGTGTGTCTT
CAAGATGGCCAGACGCCTGCCAAGTGCCTACAGTTTTTGGATGCGTTACCACGGCCCTATGTCTTCGTGG
CCTTCATCACGGCCATCAAGGTGGCCCTGGTGGTGGGCAACATGCTGGCCACCACCATCAACCCCATTGGC
CGGACCGACCCGGATGACCCCAACATCATGATCCTCTCGTGCCACCCTAACTACCGCAACGGGCTACTGTT
CAACACCAGCATGGACTTGCTGCTGTCTGTGCTGGGTTTCAGCTTCGCTTACATGGGCAAGGAGCTGCCCA
CCAACTACAACGAAGCCAAGTTCATCACTCTCAGCATGACCTTCTCCTTCACCTCCTCCATCTCCCTCTGC
ACCTTCATGTCTGTGCACGACGGCGTGCTGGTCACCATCATGGACCTCCTGGTCACTGTGCTCAACTTCCT
GGCCATCGGCTTGGGATACTTTGGCCCCAAGTGTTACATGATCCTTTTCTACCCGGAGCGCAACACCTCAG
CCTATTTCAATAGCATGATCCAGGGCTACACCATGAGGAAGAGC
(SEQ ID NO:12)

rT1R2 protein
MGPQARTLCLLSLLLHVLPKPGKLVENSDFHLAGDYLLGGLFTLHANVKSISHLSYLQVPKCNEFTMKVLG
YNLMQAMRFAVEEINNCSSLLPGVLLGYEMVDVCYLSNNIHPGLYFLAQDDDLLPILKDYSQYMPHVVAVI
GPDNSESAITVSNILSHFLIPQITYSAISDKLRDKRHFPSMLRTVPSATHHIEAMVQLMVHFQWNWIVVLV
SDDDYGRENSHLLSQRLTKTSDICIAFQEVLPIPESSQVMRSEEQRQLDNILDKLRRTSARVVVVFSPELS
LYSFFHEVLRWNFTGFVWIASESWAIDPVLHNLTELRHTGTFLGVTIQRVSIPGFSQFRVRRDKPGYFVPN
TTNLRTTCNQDCDACLNTTKSFNNILILSGERVVYSVYSAVYAVAHALHRLLGCNRVRCTKQKVYPWQLLR
EIWHVNFTLLGNRLFFDQQGDMPMLLDIIQWQWDLSQNPFQSIASYSPTSKRLTYINNVSWYTPNNTVPVS
MCSKSCQPGQMKKSVGLHPCCFECLDCMPGTYLNRSADEFNCLSCPGSMWSYKNDITCFQRRPTFLEWHEV
PTIVVAILAALGFFSTLAILFIFWRHFQTPMVRSAGGPMCFLMLVPLLLAFGMVPVYVGPPTVFSCFCRQA
FFTVCFSICLSCITVRSFQIVCVFKMARRLPSAYSFWMRYHGPYVFVAFITAIKVALVVGNMLATTINPIG
RTDPDDPNIMILSCHPNYRNGLLFNTSMDLLLSVLGFSFAYMGKELPTNYNEAKFITLSMTFSFTSSISLC
TFMSVHDGVLVTIMDLLVTVLNFLAIGLGYFGPKCYMILFYPERNTSAYFNSMIQGYTMRKS
(SEQ ID NO:13)

hT1R3 cDNA
ATGCTGGGCCCTGCTGTCCTGGGCCTCAGCCTCTGGGCTCTCCTGCACCCTGGGACGGGGGCCCCATTGTG
CCTGTCACAGCAACTTAGGATGAAGGGGACTACGTGCTGGGGGGCTGTTCCCCCTGGGCGAGGCCGAGG
AGGCTGGCCTCCGCAGCCGGACACGGCCGGCCCAGCAGCCCTGTGTGCACCAGGTTCTCCTCAAACGGCCTGCTC
TGGGCACTGGCCATGAAAATGGCCGTGGAGGAGATCAACAACAAGTCGGATCTGCTGCTCGCCGGGCTGCGCCT
GGGCTACGACCTCTTTGATACGTGCTCGGAGCCTGTGGTGGCCATGAAGCCCAGCCTCATGTTCCTGGCCA
AGGCAGGCAGCCGCGACATCGCCGCCTACTGCAACTACACGCAGTACCAGCCCCGTGTGCTGGCTGTCATC
GGGCCCCACTCGTCAGAGCTCGCCATGGTCACCGGCAAGTTCTTCAGCTTCTTCCTCATGCCCCAggtcag
CTACGGTGCTAGCATGGAGCTGCTGAGCGCCCGGGAGACCTTCCCCTCCTTCTTCCGCACCGTGCCCAGCG
```

Figure 6 (continued)

```
ACCGTGTGCAGCTGACGGCCGCCGCGGAGCTGCTGCAGGAGTTCGGCTGGAACTGGGTGGCCGCCCTGGGC
AGCGACGACGAGTACGGCCGGCAGGGCCTGAGCATCTTCTCGGCCCTGGCCGCGGGCACGCGGCATCTGCAT
CGCGCACGAGGGCCTGGTGCCGCTGCCCCGTGCCGATGACTCGCGGCTGGGGAAGGTGCAGGACGTCCTGC
ACCAGGTGAACCAGAGCAGCGTGCAGGTGGTGCTGCTGTTCGCCTCCGTGCACGCCGCCCACGCCCTCTTC
AACTACAGCATCAGCAGCAGGCTCTCGCCCAAGGTGTGGGTGGCCAGCGAGGCCTGGCTGACCTCTGACCT
GGTCATGGGGCTGCCCGGCATGGCCCAGATGGGCACGGTGCTTGGCTTCCTCCAGAGGGGTGCCCAGCTGC
ACGAGTTCCCCCAGTACGTGAAGACGCACCTGGCCCTGGCCACCGACCCGGCCTTCTGCTCTGCCCTGGGC
GAGAGGGAGCAGGGTCTGGAGGAGGACGTGGTGGGCCAGCGCTGCCCGCAGTGTGACTGCATCACGCTGCA
GAACGTGAGCGCAGGGCTAAATCACCACCAGACGTTCTCTGTCTACGCAGCTGTGTATAGCGTGGCCCAGG
CCCTGCACAACACTCTTCAGTGCAACGCCTCAGGCTGCCCCGCGCAGGACCCCGTGAAGCCCTGGCAGCTC
CTGGAGAACATGTACAACCTGACCTTCCACGTGGGCGGGCTGCCGCTGCGGTTCGACAGCAGCGGAAACGT
GGACATGGAGTACGACCTGAAGCTGTGGGTGTGGCAGGGCTCAGTGCCCAGGCTCCACGACGTGGGCAGGT
TCAACGGCAGCCTCAGGACAGAGCGCCTGAAGATCCGCTGGCACACGTCTGACAACCAGAAGCCCGTGTCC
CGGTGCTCGCGGCAGTGCCAGGAGGGCCAGGTGCGCCGGGTCAAGGGGTTCCACTCCTGCTGCTACGACTG
TGTGGACTGCGAGGCGGGCAGCTACCGGCAAAACCCAGACGACATCGCCTGCACCTTTTGTGGCCAGGATG
AGTGGTCCCCGGAGCGAAGCACACGCTGCTTCCGCCGCAGGTCTCGGTTCCTGGCATGGGGCGAGCCGGCT
GTGCTGCTGCTGCTCCTGCTGCTGAGCCTGGCGCTGGGCCTTGTGCTGGCTGCTTTGGGGCTGTTCGTTCA
CCATCGGGACAGCCCACTGGTTCAGGCCTCGGGGGGGCCCCTGGCCTGCTTTGGCCTGGTGTGCCTGGGCC
TGGTCTGCCTCAGCGTCCTCCTGTTCCCTGGCCAGCCCAGCCCTGCCCGATGCCTGGCCCAGCAGCCCTTG
TCCCACCTCCCGCTCACGGGCTGCCTGAGCACACTCTTCCTGCAGGCGGCCGAGATCTTCGTGGAGTCAGA
ACTGCCTCTGAGCTGGGCAGACCGGCTGAGTGGCTGCCTGCGGGGGCCCTGGGCCTGGCTGGTGGTGCTGC
TGGCCATGCTGGTGGAGGTCGCACTGTGCACCTGGTACCTGGTGGCCTTCCCGCCGGAGGTGGTGACGGAC
TGGCACATGCTGCCCACGGAGGCGCTGGTGCACTGCCGCACACGCTCCTGGGTCAGCTTCGGCCTAGCGCA
CGCCACCAATGCCACGCTGGCCTTTCTCTGCTTCCTGGGCACTTTCCTGGTGCGGAGCCAGCCGGGCCGCT
ACAACCGTGCCCGTGGCCTCACCTTTGCCATGCTGGCCTACTTCATCACCTGGGTCTCCTTTGTGCCCCTC
CTGGCCAATGTGCAGGTGGTCCTCAGGCCCGCCGTGCAGATGGGCGCCCTCCTGCTCTGTGTCCTGGGCAT
CCTGGCTGCCTTCCACCTGCCCAGGTGTTACCTGCTCATGCGGCAGCCAGGGCTCAACACCCCCGAGTTCT
TCCTGGGAGGGGGCCCTGGGGATGCCCAAGGCCAGAATGACGGGAACACAGGAAATCAGGGGAAACATGAG
TGA
(SEQ ID NO:14)

hT1R3 protein
MLGPAVLGLSLWALLHPGTGAPLCLSQQLRMKGDYVLGGLFPLGEAEEAGLRSRTRPSSPVCTRFSSNGLL
WALAMKMAVEEINNKSDLLPGLRLGYDLFDTCSEPVVAMKPSLMFLAKAGSRDIAAYCNYTQYQPRVLAVI
GPHSSELAMVTGKFFSFFLMPQVSYGASMELLSARETFPSFFRTVPSDRVQLTAAAELLQEFGWNWVAALG
SDDEYGRQGLSIFSALAAARGICIAHEGLVPLPRADDSRLGKVQDVLHQVNQSSVQVVLLFASVHAAHALF
NYSISSRLSPKVWVASEAWLTSDLVMGLPGMAQMGTVLGFLQRGAQLHEFPQYVKTHLALATDPAFCSALG
EREQGLEEDVVGQRCPQCDCITLQNVSAGLNHHQTFSVYAAVYSVAQALHNTLQCNASGCPAQDPVKPWQL
LENMYNLTFHVGGLPLRFDSSGNVDMEYDLKLWVWQGSVPRLHDVGRFNGSLRTERLKIRWHTSDNQKPVS
RCSRQCQEGQVRRVKGFHSCCYDCVDCEAGSYRQNPDDIACTFCGQDEWSPERSTRCFRRRSRFLAWGEPA
VLLLLLLLSLALGLVLAALGLFVHHRDSPLVQASGGPLACFGLVCLGLVCLSVLLFPGQPSPARCLAQQPL
SHLPLTGCLSTLFLQAAEIFVESELPLSWADRLSGCLRGPWAWLVVLLAMLVEVALCTWYLVAFPPEVVTD
WHMLPTEALVHCRTRSWVSFGLAHATNATLAFLCFLGTFLVRSQPGRYNRARGLTFAMLAYFITWVSFVPL
LANVQVVLRPAVQMGALLLCVLGILAAFHLPRCYLLMRQPGLNTPEFFLGGGPGDAQGQNDGNTGNQGKHE
(SEQ ID NO:15)

rT1R3 cDNA
ATGCCGGGTTTGGCTATCTTGGGCCTCAGTCTGGCTGCTTTCCTGGAGCTTGGGATGGGGTCCTCTTTGTG
TCTGTCACAGCAATTCAAGGCACAAGGGGACTATATATTGGGTGGACTATTTCCCCTGGGCACAACTGAGG
AGGCCACTCTCAACCAGAGAACACAGCCCAACGGCATCCTATGTACCAGGTTCTCGCCCCTTGGTTTGTTC
CTGGCCATGGCTATGAAGATGGCTGTAGAGGAGATCAACAATGGATCTGCCTTGCTCCCTGGGCTGCGACT
GGGCTATGACCTGTTTGACACATGCTCAGAGCCAGTGGTCACCATGAAGCCCAGCCTCATGTTCATGGCCA
AGGTGGAAGTCAAAGCATTGCTGCCTACTGCAACTACACACAGTACCAACCCCGTGTGCTGGCTGTCATT
GGTCCCCACTCATCAGAGCTTGCCCTCATTACAGGCAAGTTCTTCAGCTTCTTCCTCATGCCACAGGTCAG
CTATAGTGCCAGCATGGATCGGCTAAGTGACCGGGAAACATTTCCATCCTTCTTCCGCACAGTGCCCAGTG
ACCGGGTGCAGCTGCAGGCCGTTGTGACACTGTTGCAGAATTTCAGCTGGAACTGGGTGGCTGCCTTAGGT
AGTGATGATGACTATGGCCGGGAAGGTCTGAGCATCTTTTCTGGTCTGGCCAACTCACGAGGTATCTGCAT
```

Figure 6 (continued)

```
TGCACACGAGGGCCTGGTGCCACAACATGACACTAGTGGCCAACAATTGGGCAAGGTGGTGGATGTGCTAC
GCCAAGTGAACCAAAGCAAAGTACAGGTGGTGGTGCTGTTTGCATCTGCCCGTGCTGTCTACTCCCTTTTT
AGCTACAGCATCCTTCATGACCTCTCACCCAAGGTATGGGTGGCCAGTGAGTCCTGGCTGACCTCTGACCT
GGTCATGACACTTCCCAATATTGCCCGTGTGGGCACTGTTCTTGGGTTTCTGCAGCGCGGTGCCCTACTGC
CTGAATTTTCCCATTATGTGGAGACTCGCCTTGCCCTAGCTGCTGACCCAACATTCTGTGCCTCCCTGAAA
GCTGAGTTGGATCTGGAGGAGCGCGTGATGGGGCCACGCTGTTCACAATGTGACTACATCATGCTACAGAA
CCTGTCATCTGGGCTGATGCAGAACCTATCAGCTGGGCAGTTGCACCACCAAATATTTGCAACCTATGCAG
CTGTGTACAGTGTGGCTCAGGCCCTTCACAACACCCTGCAGTGCAATGTCTCACATTGCCACACATCAGAG
CCTGTTCAACCCTGGCAGCTCCTGGAGAACATGTACAATATGAGTTTCCGTGCTCGAGACTTGACACTGCA
GTTTGATGCCAAAGGGAGTGTAGACATGGAATATGACCTGAAGATGTGGGTGTGGCAGAGCCCTACACCTG
TACTACATACTGTAGGCACCTTCAACGGCACCCTTCAGCTGCAGCACTCGAAAATGTATTGGCCAGGCAAC
CAGGTGCCAGTCTCCCAGTGCTCCCGGCAGTGCAAAGATGGCCAGGTGCGCAGAGTAAAGGGCTTTCATTC
CTGCTGCTATGACTGTGTGGACTGCAAGGCAGGGAGCTACCGGAAGCATCCAGATGACTTCACCTGTACTC
CATGTGGCAAGGATCAGTGGTCCCCAGAAAAAAGCACAACCTGCTTACCTCGCAGGCCCAAGTTTCTGGCT
TGGGGGGAGCCAGCTGTGCTGTCACTTCTCCTGCTGCTTTGCCTGGTGCTGGGCCTGACACTGGCTGCCCT
GGGGCTCTTTGTCCACTACTGGGACAGCCCTCTTGTCAGGCCTCAGGTGGGTCACTGTTCTGCTTTGGCC
TGATCTGCCTAGGCCTCTTCTGCCTCAGTGTCCTTCTGTTCCCAGGACGACCACGCTCTGCCAGCTGCCTT
GCCCAACAACCAATGGCTCACCTCCCTCTCACAGGCTGCCTGAGCACACTCTTCCTGCAAGCAGCCGAGAT
CTTTGTGGAGTCTGAGCTGCCACTGAGTTGGGCAAACTGGCTCTGCAGCTACCTTCGGGGGCCCCTGGGCTT
GGCTGGTGGTACTGCTGGCCACTCTTGTGGAGGCTGCACTATGTGCCTGGTACTTGATGGCTTTCCCTCCA
GAGGTGGTGACAGATTGGCAGGTGCTGCCCACGGAGGTACTGGAACACTGCCGCATGCGTTCCTGGGTCAG
CCTGGGCTTGGTGCACATCACCAATGCAGTGTTAGCTTTCCTCTGCTTTCTGGGCACTTTCCTGGTACACA
GCCAGCCTGGTCGCTATAACCGTGCCCGTGGCCTCACCTTCGCCATGCTAGCTTATTTCATCATCTGGGTC
TCTTTTGTGCCCCTCCTGGCTAATGTGCAGGTGGCCTACCAGCCAGCTGTGCAGATGGGTGCTATCTTATT
CTGTGCCCTGGGCATCCTGGCCACCTTCCACCTGCCCAAATGCTATGTACTTCTGTGGCTGCCAGAGCTCA
ACACCCAGGAGTTCTTCCTGGGAAGGAGCCCCAAGGAAGCATCAGATGGGAATAGTGGTAGTAGTGAGGCA
ACTCGGGGACACAGTGAATGA
(SEQ ID NO:16)

rT1R3 protein
MPGLAILGLSLAAFLELGMGSSLCLSQQFKAQGDYILGGLFPLGTTEFATLNQRTQPNGILCTRFSPLGLF
LAMAMKMAVEEINNGSALLPGLRLGYDLFDTCSEPVVTMKPSLMFMAKVGSQSIAAYCNYTQYQPRVLAVI
GPHSSELALITCKFFSFFLMPQVSYSASMDRLSDRETFPSFFRTVPSDRVQLQAVVTLLQNFSWNWVAALG
SDDDYGREGLSIFSGLANSRGICIAHEGLVPQHDTSGQQLGKVVDVLRQVNQSKVQVVVLFASARAVYSLF
SYSILHDLSPKVWVASESWLTSDLVMTLPNIARVGTVLGFLQRGALLPEFSHYVETRLALAADPTFCASLK
AELDLEERVMGPRCSQCDYIMLQNLSSGLMQNLSAGQLHHQIFATYAAVYSVAQALHNTLQCNVSHCHTSE
PVQPWQLLENMYNMSFRARDLTLQFDAKGSVDMEYDLKMWVWQSPTPVLHTVGTFNGTLQLQHSKMYWPGN
QVPVSQCSRQCKDGQVRRVKGFHSCCYDCVDCKAGSYRKHPDDFTCTPCGKDQWSPEKSTTCLPRRPKFLA
WGEPAVLSLLLLLCLVLGLTLAALGLFVHYWDSPLVQASGGSLFCFGLICLGLPCLSVLLFPGRPRSASCL
AQQPMAHLPLTGCLSTLFLQAAEIFVESELPLSWANWLCSYLRGPWAWLVVLLATLVEAALCAWYLMAFPP
EVVTDWQVLPTEVLEHCRMRSWVSLGLVHITNAVLAFLCFLGTFLVQSQPGRYNRARGLTFAMLAYFIIWV
SFVPLLANVQVAYQPAVQMGAILFCALGILATFHLPKCYVLLWLPELNTQEFFLGRSPKEASDGNSGSSEA
TRGHSE
(SEQ ID NO:17)
```

Sweet-umami receptor responds to most sweeteners except for cyclamate

FIGURE 8

| Ligands | h2/h3 | h2-h1/h3 |
|---|---|---|
| Aspartame | 0.5 mM | 0.97 mM |
| D-Trp | 1 mM | 3.2 mM |
| Sucrose | 20 mM | >50 mM |
| Fructose | 20 mM | >50 mM |
| Cyclamate | 0.5 mM | N/A |

Cyclamate enhances aspartame response in hT1R2-1/h3 stable line

'807 enhances aspartame response

Aspartame (0.1 mM)    807 (6nM)    Aspartame (0.1mM) + 807(6nM)

hT1R1-2/rT1R3 Responds to Umami Ligands hT1R1-2/rT1R3 Activity is Enhanced by IMP

SEQUENCE LISTING

<160> NUMBER OF SEQ ID NOS: 17

<210> SEQ ID NO 1
<211> LENGTH: 2523
<212> TYPE: DNA
<213> ORGANISM: Homo sapiens

<400> SEQUENCE: 1

```
atggggccca gggcaaagac catctgctcc ctgttcttcc tcctatgggt cctggctgag      60
ccggctgaga actcggactt ctacctgcct ggggattacc tcctgggtgg cctcttctcc     120
ctccatgcca acatgaaggg cattgttcac cttaacttcc tgcaggtgcc catgtgcaag     180
gagtatgaag tgaaggtgat aggctacaac ctcatgcagg ccatgcgctt cgcggtggag     240
gagatcaaca atgacagcag cctgctgcct ggtgtgctgc tgggctatga gatcgtggat     300
gtgtgctaca tctccaacaa tgtccagccg gtgctctact tcctggcaca cgaggacaac     360
ctccttccca tccaagagga ctacagtaac tacatttccc gtgtggtggc tgtcattggc     420
cctgacaact ccgagtctgt catgactgtg gccaacttcc tctccctatt tctccttcca     480
cagatcacct acagcgccat cagcgatgag ctgcgagaca aggtgcgctt cccggctttg     540
ctgcgtacca cacccagcgc cgaccaccac gtcgaggcca tggtgcagct gatgctgcac     600
ttccgctgga actggatcat tgtgctggtg agcagcgaca cctatggccg cgacaatggc     660
cagctgcttg gcgagcgcgt ggcccggcgc gacatctgca tcgccttcca ggagacgctg     720
cccacactgc agcccaacca gaacatgacg tcagaggagc gccagcgcct ggtgaccatt     780
gtggacaagc tgcagcagag cacagcgcgc gtcgtggtcg tgttctcgcc cgacctgacc     840
ctgtaccact tcttcaatga ggtgctgcgc cagaacttca cgggcgccgt gtggatcgcc     900
tccgagtcct gggccatcga cccggtcctg cacaacctca ggagctgggc cacttgggc     960 accttcctgg gcatcaccat ccagagcgtg cccatcccgg gcttcagtga gttccgcgag    1020
tggggcccac aggctgggcc gccacccctc agcaggacca gccagagcta tacctgcaac    1080
caggagtgcg acaactgcct gaacgccacc ttgtccttca acaccattct caggctctct    1140
ggggagcgtg tcgtctacag cgtgtactct gcggtctatg cgtggccca tgccctgcac    1200 agcctcctcg gctgtgacaa aagcacctgc accaagaggg tggtctaccc ctggcagctg    1260
cttgaggaga tctggaaggt caacttcact ctcctggacc accaaatctt cttcgacccg    1320
caaggggacg tggctctgca cttggagatt gtccagtggc aatgggaccg gagccagaat    1380
cccttccaga gcgtcgcctc ctactacccc ctgcagcgac agctgaagaa catccaagac    1440
atctcctggc acaccgtcaa caacacgatc cctatgtcca tgtgttccaa gaggtgccag    1500
tcagggcaaa agaagaagcc tgtgggcatc cacgtctgct gcttcgagtg catcgactgc    1560
cttcccggca ccttcctcaa ccacactgaa gatgaatatg aatgccagcc ctgcccgaat    1620
aacgagtggt cctaccagag tgagacctcc tgcttcaagc ggcagctggt cttcctcgag    1680
ttgcgtgagc acacctcttg ggtgctgctg cagctaacg ctgctgct gctgctgctg    1740 cttgggactg ctggcctgtt tgcctggcac ctagacaccc ctgtggtgag gtcagcaggg    1800
ggccgcctgt gctttcttat gctgggctcc ctggcagcag gtagtggcag cctctatggc    1860
```

```
ttctttgggg aacccacaag gcctgcgtgc ttgctacgcc aggccctctt tgcccttggt   1920
ttcaccatct tcctgtcctg cctgacagtt cgctcattcc aactaatcat catcttcaag   1980
ttttccacca aggtacctac attctaccac gcctgggtcc aaaaccacgg tgctggcctg   2040
tttgtgatga tcagctcagc ggcccagctg cttatctgtc taacttggct ggtggtgtgg   2100
accccactgc ctgctaggga ataccagcgc ttcccccatc tggtgatgct tgagtgcaca   2160
gagaccaact ccctgggctt catactggcc ttcctctaca atggcctcct ctccatcagt   2220
gcctttgcct gcagctacct gggtaaggac ttgccagaga actacaacga ggccaaatgt   2280
gtcaccttca gcctgctctt caacttcgtg tcctggatcg ccttcttcac cacggccagc   2340
gtctacgacg gcaagtacct gcctgcggcc aacatgatgg ctgggctgag cagcctgagc   2400
agcggcttcg gtgggtattt tctgcctaag tgctacgtga tcctctgccg cccagacctc   2460
aacagcacag agcacttcca ggcctccatt caggactaca cgaggcgctg cggctccacc   2520
tga                                                                2523
```

<210> SEQ ID NO 2
<211> LENGTH: 840
<212> TYPE: PRT
<213> ORGANISM: Homo sapiens

<400> SEQUENCE: 2

```
Met Gly Pro Arg Ala Lys Thr Ile Cys Ser Leu Phe Phe Leu Leu Trp
  1               5                  10                  15

Val Leu Ala Glu Pro Ala Glu Asn Ser Asp Phe Tyr Leu Pro Gly Asp
             20                  25                  30

Tyr Leu Gly Gly Leu Phe Ser Leu His Ala Asn Met Lys Gly Ile
         35                  40                  45

Val His Leu Asn Phe Leu Gln Val Pro Met Cys Lys Glu Tyr Glu Val
     50                  55                  60

Lys Val Ile Gly Tyr Asn Leu Met Gln Ala Met Arg Phe Ala Val Glu
 65                  70                  75                  80

Glu Ile Asn Asn Asp Ser Ser Leu Leu Pro Gly Val Leu Leu Gly Tyr
                 85                  90                  95

Glu Ile Val Asp Val Cys Tyr Ile Ser Asn Asn Val Gln Pro Val Leu
            100                 105                 110

Tyr Phe Leu Ala His Glu Asp Asn Leu Leu Pro Ile Gln Glu Asp Tyr
        115                 120                 125

Ser Asn Tyr Ile Ser Arg Val Val Ala Val Ile Gly Pro Asp Asn Ser
    130                 135                 140

Glu Ser Val Met Thr Val Ala Asn Phe Leu Ser Leu Phe Leu Leu Pro
145                 150                 155                 160

Gln Ile Thr Tyr Ser Ala Ile Ser Asp Glu Leu Arg Asp Lys Val Arg
                165                 170                 175

Phe Pro Ala Leu Leu Arg Thr Thr Pro Ser Ala Asp His His Val Glu
            180                 185                 190

Ala Met Val Gln Leu Met Leu His Phe Arg Trp Asn Trp Ile Ile Val
        195                 200                 205

Leu Val Ser Ser Asp Thr Tyr Gly Arg Asp Asn Gly Gln Leu Leu Gly
    210                 215                 220

Glu Arg Val Ala Arg Arg Asp Ile Cys Ile Ala Phe Gln Glu Thr Leu
225                 230                 235                 240

Pro Thr Leu Gln Pro Asn Gln Asn Met Thr Ser Glu Glu Arg Gln Arg
                245                 250                 255
```

```
Leu Val Thr Ile Val Asp Lys Leu Gln Gln Ser Thr Ala Arg Val Val
            260                 265                 270

Val Val Phe Ser Pro Asp Leu Thr Leu Tyr His Phe Asn Glu Val
        275                 280                 285

Leu Arg Gln Asn Phe Thr Gly Ala Val Trp Ile Ala Ser Glu Ser Trp
    290                 295                 300

Ala Ile Asp Pro Val Leu His Asn Leu Thr Glu Leu Gly His Leu Gly
305                 310                 315                 320

Thr Phe Leu Gly Ile Thr Ile Gln Ser Val Pro Ile Pro Gly Phe Ser
                325                 330                 335

Glu Phe Arg Glu Trp Gly Pro Gln Ala Gly Pro Pro Leu Ser Arg
                340                 345                 350

Thr Ser Gln Ser Tyr Thr Cys Asn Gln Glu Cys Asp Asn Cys Leu Asn
        355                 360                 365

Ala Thr Leu Ser Phe Asn Thr Ile Leu Arg Leu Ser Gly Glu Arg Val
370                 375                 380

Val Tyr Ser Val Tyr Ser Ala Val Tyr Ala Val Ala His Ala Leu His
385                 390                 395                 400

Ser Leu Leu Gly Cys Asp Lys Ser Thr Cys Thr Lys Arg Val Val Tyr
                405                 410                 415

Pro Trp Gln Leu Leu Glu Glu Ile Trp Lys Val Asn Phe Thr Leu Leu
                420                 425                 430

Asp His Gln Ile Phe Phe Asp Pro Gln Gly Asp Val Ala Leu His Leu
        435                 440                 445

Glu Ile Val Gln Trp Gln Trp Asp Arg Ser Gln Asn Pro Phe Gln Ser
    450                 455                 460

Val Ala Ser Tyr Tyr Pro Leu Gln Arg Gln Leu Lys Asn Ile Gln Asp
465                 470                 475                 480

Ile Ser Trp His Thr Val Asn Asn Thr Ile Pro Met Ser Met Cys Ser
                485                 490                 495

Lys Arg Cys Gln Ser Gly Gln Lys Lys Lys Pro Val Gly Ile His Val
                500                 505                 510

Cys Cys Phe Glu Cys Ile Asp Cys Leu Pro Gly Thr Phe Leu Asn His
        515                 520                 525

Thr Glu Asp Glu Tyr Glu Cys Gln Ala Cys Pro Asn Asn Glu Trp Ser
        530                 535                 540

Tyr Gln Ser Glu Thr Ser Cys Phe Lys Arg Gln Leu Val Phe Leu Glu
545                 550                 555                 560

Leu Arg Glu His Thr Ser Trp Val Leu Leu Ala Ala Asn Thr Leu Leu
                565                 570                 575

Leu Leu Leu Leu Leu Gly Thr Ala Gly Leu Phe Ala Trp His Leu Asp
            580                 585                 590

Thr Pro Val Val Arg Ser Ala Gly Gly Arg Leu Cys Phe Leu Met Leu
            595                 600                 605

Gly Ser Leu Ala Ala Gly Ser Gly Ser Leu Tyr Gly Phe Phe Gly Glu
    610                 615                 620

Pro Thr Arg Pro Ala Cys Leu Leu Arg Gln Ala Leu Phe Ala Leu Gly
625                 630                 635                 640

Phe Thr Ile Phe Leu Ser Cys Leu Thr Val Arg Ser Phe Gln Leu Ile
                645                 650                 655

Ile Ile Phe Lys Phe Ser Thr Lys Val Pro Thr Phe Tyr His Ala Trp
            660                 665                 670

Val Gln Asn His Gly Ala Gly Leu Phe Val Met Ile Ser Ser Ala Ala
```

```
                    675                 680                 685
Gln Leu Leu Ile Cys Leu Thr Trp Leu Val Val Trp Thr Pro Leu Pro
    690                 695                 700
Ala Arg Glu Tyr Gln Arg Phe Pro His Leu Val Met Leu Glu Cys Thr
705                 710                 715                 720
Glu Thr Asn Ser Leu Gly Phe Ile Leu Ala Phe Leu Tyr Asn Gly Leu
                725                 730                 735
Leu Ser Ile Ser Ala Phe Ala Cys Ser Tyr Leu Gly Lys Asp Leu Pro
            740                 745                 750
Glu Asn Tyr Asn Glu Ala Lys Cys Val Thr Phe Ser Leu Leu Phe Asn
        755                 760                 765
Phe Val Ser Trp Ile Ala Phe Phe Thr Thr Ala Ser Val Tyr Asp Gly
    770                 775                 780
Lys Tyr Leu Pro Ala Ala Asn Met Met Ala Gly Leu Ser Ser Leu Ser
785                 790                 795                 800
Ser Gly Phe Gly Gly Tyr Phe Leu Pro Lys Cys Tyr Val Ile Leu Cys
                805                 810                 815
Arg Pro Asp Leu Asn Ser Thr Glu His Phe Gln Ala Ser Ile Gln Asp
            820                 825                 830
Tyr Thr Arg Arg Cys Gly Ser Thr
        835                 840

<210> SEQ ID NO 3
<211> LENGTH: 2523
<212> TYPE: DNA
<213> ORGANISM: Homo sapiens

<400> SEQUENCE: 3
atgctgctct gcacggctcg cctggtcggc ctgcagcttc tcatttcctg ctgctgggcc      60
tttgcctgcc atagcacgga gtcttctcct gacttcaccc tccccggaga ttacctcctg     120
gcaggcctgt ccctctcca ttctggctgt ctgcaggtga ggcacagacc cgaggtgacc     180
ctgtgtgaca ggtcttgtag cttcaatgag catggctacc acctcttcca ggctatgcgg     240
cttggggttg aggagataaa caactccacg gccctgctgc ccaacatcac cctggggtac     300
cagctgtatg atgtgtgttc tgactctgcc aatgtgtatg ccacgctgag agtgctctcc     360
ctgccagggc aacaccacat agagctccaa ggagaccttc tccactattc ccctacggtg     420
ctggcagtga ttgggcctga cagcaccaac cgtgctgcca ccagccgcc cctgctgagc     480 cctttcctgg tgcccatgat tagctatgcg gccagcagcg agacgctcag cgtgaagcgg     540
cagtatccct ctttcctgcg caccatcccc aatgacaagt accaggtgga gaccatggtg     600
ctgctgctgc agaagttcgg gtggacctgg atctctctgg ttggcagcag tgacgactat     660
gggcagctag gggtgcaggc actggagaac caggccactg gtcagggat ctgcattgct     720 ttcaaggaca tcatgccctt ctctgcccag gtgggcgatg agaggatgca gtgcctcatg     780
cgccacctgg cccaggccgg ggccaccgtc gtggttgttt tttccagccg gcagttggcc     840
agggtgtttt tcgagtccgt ggtgctgacc aacctgactg caaggtgtg ggtcgcctca     900 gaagcctggg ccctctccag gcacatcact ggggtgcccg ggatccagcg cattgggatg     960
gtgctgggcg tggccatcca agagggggct gtccctggcc tgaaggcgtt tgaagaagcc    1020
tatgcccggg cagacaagaa ggccccctagg ccttgccaca agggctcctg gtgcagcagc    1080
aatcagctct gcagagaatg ccaagctttc atggcacaca cgatgcccaa gctcaaagcc    1140
ttctccatga gttctgccta caacgcatac cgggctgtgt atgcggtggc ccatggcctc    1200
```

```
caccagctcc tgggctgtgc tctctggagct tgttccaggg gccgagtcta cccctggcag    1260
cttttggagc agatccacaa ggtgcatttc cttctacaca aggacactgt ggcgtttaat    1320
gacaacagag atcccctcag tagctataac ataattgcct gggactggaa tggacccaag    1380
tggaccttca cggtcctcgg ttcctccaca tggtctccag ttcagctaaa cataaatgag    1440
accaaaatcc agtggcacgg aaaggacaac caggtgccta agtctgtgtg ttccagcgac    1500
tgtcttgaag ggcaccagcg agtggttacg ggtttccatc actgctgctt tgagtgtgtg    1560
ccctgtgggg ctgggacctt cctcaacaag agtgacctct acagatgcca gccttgtggg    1620
aaagaagagt gggcacctga gggaagccag acctgcttcc cgcgcactgt ggtgtttctc    1680
gagtggcatg aggcacccac catcgctgtg ccctgctgg ccgccctggg cttcctcagc    1740
accctggcca tcctggtgat attctggagg cacttccaga cacccatagt tcgctcggct    1800
gggggcccca tgtgcttcct gatgctgaca ctgctgctgg tggcatacat ggtggtcccg    1860
gtgtacgtgg ggccgcccaa ggtctccacc tgcctctgcc gccaggccct ctttcccctc    1920
tgcttcacaa tttgcatctc ctgtatcgcc gtgcgttctt tccagatcgt ctgcgccttc    1980
aagatggcca ccgcttccc acgcgcctac agctactggg tccgctacca ggggccctac    2040
gtctctatgg catttatcac ggtactcaaa atggtcattg tggtaattgg catgctggcc    2100
acgggcctca gtcccaccac ccgtactgac cccgatgacc ccaagatcac aattgtctcc    2160
tgtaacccca actaccgcaa cagcctgctg ttcaacacca gcctggacct gctgctctca    2220
gtggtgggtt tcagcttcgc ctacatgggc aaagagctgc caccaactag caacgaggcc    2280
aagttcatca ccctcagcat gaccttctat ttcacctcat ccgtctccct ctgcaccttc    2340
atgtctgcct acagcggggt gctggtcacc atcgtggacc tcttggtcac tgtgctcaac    2400
ctcctggcca tcagcctggg ctacttcggc cccagtgctc acatgatcct cttctacccg    2460
gagcgcaaca cgcccgccta cttcaacagc atgatccagg gctacaccat gaggagggac    2520
tag                                                                  2523
```

<210> SEQ ID NO 4
<211> LENGTH: 840
<212> TYPE: PRT
<213> ORGANISM: Homo sapiens

<400> SEQUENCE: 4

```
Met Leu Leu Cys Thr Ala Arg Leu Val Gly Leu Gln Leu Leu Ile Ser
 1               5                  10                  15

Cys Cys Trp Ala Phe Ala Cys His Ser Thr Glu Ser Ser Pro Asp Phe
            20                  25                  30

Thr Leu Pro Gly Asp Tyr Leu Leu Ala Gly Leu Phe Pro Leu His Ser
        35                  40                  45

Gly Cys Leu Gln Val Arg His Arg Pro Glu Val Thr Leu Cys Asp Arg
    50                  55                  60

Ser Cys Ser Phe Asn Glu His Gly Tyr His Leu Phe Gln Ala Met Arg
65                  70                  75                  80

Leu Gly Val Glu Glu Ile Asn Asn Ser Thr Ala Leu Leu Pro Asn Ile
                85                  90                  95

Thr Leu Gly Tyr Gln Leu Tyr Asp Val Cys Ser Asp Ser Ala Asn Val
            100                 105                 110

Tyr Ala Thr Leu Arg Val Leu Ser Leu Pro Gly Gln His His Ile Glu
        115                 120                 125

Leu Gln Gly Asp Leu Leu His Tyr Ser Pro Thr Val Leu Ala Val Ile
    130                 135                 140
```

```
Gly Pro Asp Ser Thr Asn Arg Ala Ala Thr Ala Ala Leu Leu Ser
145                 150                 155                 160

Pro Phe Leu Val Pro Met Ile Ser Tyr Ala Ala Ser Ser Glu Thr Leu
                165                 170                 175

Ser Val Lys Arg Gln Tyr Pro Ser Phe Leu Arg Thr Ile Pro Asn Asp
            180                 185                 190

Lys Tyr Gln Val Glu Thr Met Val Leu Leu Gln Lys Phe Gly Trp
        195                 200                 205

Thr Trp Ile Ser Leu Val Gly Ser Ser Asp Tyr Gly Gln Leu Gly
    210                 215                 220

Val Gln Ala Leu Glu Asn Gln Ala Thr Gly Gln Gly Ile Cys Ile Ala
225                 230                 235                 240

Phe Lys Asp Ile Met Pro Phe Ser Ala Gln Val Gly Asp Glu Arg Met
                245                 250                 255

Gln Cys Leu Met Arg His Leu Ala Gln Ala Gly Ala Thr Val Val Val
                260                 265                 270

Val Phe Ser Ser Arg Gln Leu Ala Arg Val Phe Phe Glu Ser Val Val
            275                 280                 285

Leu Thr Asn Leu Thr Gly Lys Val Trp Val Ala Ser Glu Ala Trp Ala
290                 295                 300

Leu Ser Arg His Ile Thr Gly Val Pro Gly Ile Gln Arg Ile Gly Met
305                 310                 315                 320

Val Leu Gly Val Ala Ile Gln Lys Arg Ala Val Pro Gly Leu Lys Ala
                325                 330                 335

Phe Glu Glu Ala Tyr Ala Arg Ala Asp Lys Lys Ala Pro Arg Pro Cys
                340                 345                 350

His Lys Gly Ser Trp Cys Ser Ser Asn Gln Leu Cys Arg Glu Cys Gln
            355                 360                 365

Ala Phe Met Ala His Thr Met Pro Lys Leu Lys Ala Phe Ser Met Ser
    370                 375                 380

Ser Ala Tyr Asn Ala Tyr Arg Ala Val Tyr Ala Val Ala His Gly Leu
385                 390                 395                 400

His Gln Leu Leu Gly Cys Ala Ser Gly Ala Cys Ser Arg Gly Arg Val
                405                 410                 415

Tyr Pro Trp Gln Leu Leu Glu Gln Ile His Lys Val His Phe Leu Leu
                420                 425                 430

His Lys Asp Thr Val Ala Phe Asn Asp Asn Arg Asp Pro Leu Ser Ser
            435                 440                 445

Tyr Asn Ile Ile Ala Trp Asp Trp Asn Gly Pro Lys Trp Thr Phe Thr
        450                 455                 460

Val Leu Gly Ser Ser Thr Trp Ser Pro Val Gln Leu Asn Ile Asn Glu
465                 470                 475                 480

Thr Lys Ile Gln Trp His Gly Lys Asp Asn Gln Val Pro Lys Ser Val
                485                 490                 495

Cys Ser Ser Asp Cys Leu Glu Gly His Gln Arg Val Val Thr Gly Phe
            500                 505                 510

His His Cys Cys Phe Glu Cys Val Pro Cys Gly Ala Gly Thr Phe Leu
        515                 520                 525

Asn Lys Ser Asp Leu Tyr Arg Cys Gln Pro Cys Gly Lys Glu Glu Trp
    530                 535                 540

Ala Pro Glu Gly Ser Gln Thr Cys Phe Pro Arg Thr Val Val Phe Leu
545                 550                 555                 560

Glu Trp His Glu Ala Pro Thr Ile Ala Val Ala Leu Leu Ala Ala Leu
```

```
                565                 570                 575
Gly Phe Leu Ser Thr Leu Ala Ile Leu Val Ile Phe Trp Arg His Phe
            580                 585                 590

Gln Thr Pro Ile Val Arg Ser Ala Gly Gly Pro Met Cys Phe Leu Met
        595                 600                 605

Leu Thr Leu Leu Leu Val Ala Tyr Met Val Pro Val Tyr Val Gly
    610                 615                 620

Pro Pro Lys Val Ser Thr Cys Leu Cys Arg Gln Ala Leu Phe Pro Leu
625                 630                 635                 640

Cys Phe Thr Ile Cys Ile Ser Cys Ile Ala Val Arg Ser Phe Gln Ile
                645                 650                 655

Val Cys Ala Phe Lys Met Ala Ser Arg Phe Pro Arg Ala Tyr Ser Tyr
            660                 665                 670

Trp Val Arg Tyr Gln Gly Pro Tyr Val Ser Met Ala Phe Ile Thr Val
        675                 680                 685

Leu Lys Met Val Ile Val Ile Gly Met Leu Ala Thr Gly Leu Ser
    690                 695                 700

Pro Thr Thr Arg Thr Asp Pro Asp Pro Lys Ile Thr Ile Val Ser
705                 710                 715                 720

Cys Asn Pro Asn Tyr Arg Asn Ser Leu Leu Phe Asn Thr Ser Leu Asp
                725                 730                 735

Leu Leu Leu Ser Val Val Gly Phe Ser Phe Ala Tyr Met Gly Lys Glu
            740                 745                 750

Leu Pro Thr Asn Tyr Asn Glu Ala Lys Phe Ile Thr Leu Ser Met Thr
        755                 760                 765

Phe Tyr Phe Thr Ser Ser Val Ser Leu Cys Thr Phe Met Ser Ala Tyr
    770                 775                 780

Ser Gly Val Leu Val Thr Ile Val Asp Leu Leu Val Thr Val Leu Asn
785                 790                 795                 800

Leu Leu Ala Ile Ser Leu Gly Tyr Phe Gly Pro Lys Cys Tyr Met Ile
                805                 810                 815

Leu Phe Tyr Pro Glu Arg Asn Thr Pro Ala Tyr Phe Asn Ser Met Ile
            820                 825                 830

Gln Gly Tyr Thr Met Arg Arg Asp
        835                 840

<210> SEQ ID NO 5
<211> LENGTH: 374
<212> TYPE: PRT
<213> ORGANISM: Homo sapiens

<400> SEQUENCE: 5

Met Ala Arg Ser Leu Thr Trp Arg Cys Cys Pro Trp Cys Leu Thr Glu
  1               5                  10                  15

Asp Glu Lys Ala Ala Arg Val Asp Gln Glu Ile Asn Arg Ile Leu
             20                  25                  30

Leu Glu Gln Lys Lys Gln Asp Arg Gly Glu Leu Lys Leu Leu Leu
         35                  40                  45

Gly Pro Gly Glu Ser Gly Lys Ser Thr Phe Ile Lys Gln Met Arg Ile
     50                  55                  60

Ile His Gly Ala Gly Tyr Ser Glu Glu Arg Lys Gly Phe Arg Pro
 65                  70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
```

```
                      100                 105                 110
Ala Ser Leu Val Met Ser Gln Asp Pro Tyr Lys Val Thr Thr Phe Glu
            115                 120                 125

Lys Arg Tyr Ala Ala Met Gln Trp Leu Trp Arg Asp Ala Gly Ile
        130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
                195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
        290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Asn Leu Lys Lys Glu Asp
                325                 330                 335

Lys Glu Ile Tyr Ser His Met Thr Cys Ala Thr Asp Thr Gln Asn Val
                340                 345                 350

Lys Phe Val Phe Asp Ala Val Thr Asp Ile Ile Ile Lys Glu Asn Leu
            355                 360                 365

Lys Asp Cys Gly Leu Phe
370

<210> SEQ ID NO 6
<211> LENGTH: 2526
<212> TYPE: DNA
<213> ORGANISM: Homo sapiens

<400> SEQUENCE: 6
atgctgctct gcacggctcg cctggtcggc ctgcagcttc tcatttcctg ctgctgggcc      60
tttgcctgcc atagcacgga gtcttctcct gacttcaccc tccccggaga ttacctcctg     120
gcaggcctgt ccctctccaa ttctggctgt ctgcaggtga ggcacagacc cgaggtgacc     180
ctgtgtgaca ggtcttgtag cttcaatgag catggctacc acctcttcca ggctatgcgg     240
cttggggttg aggagataaa caactccacg gccctgctgc caacatcac cctggggtac      300 cagctgtatg atgtgtgttc tgactctgcc aatgtgtatg ccacgctgag agtgctctcc     360
ctgccagggc aacaccacat agagctccaa ggagaccttc tccactattc ccctacggtg     420
ctggcagtga ttgggcctga cagcaccaac cgtgctgcca ccacagccgc cctgctgagc     480
cctttcctgg tgcccatgat tagctatgcg gccagcagcg agacgctcag cgtgaagcgg     540
cagtatccct ctttcctgcg caccatcccc aatgacaagt accaggtgga gaccatggtg     600
```

```
ctgctgctgc agaagttcgg gtggacctgg atctctctgg ttggcagcag tgacgactat    660
gggcagctag gggtgcaggc actggagaac caggccactg gtcagggat ctgcattgct     720 ttcaaggaca tcatgccctt ctctgcccag gtgggcgatg agaggatgca gtgcctcatg    780
cgccacctgg cccaggccgg ggccaccgtc gtggttgttt tttccagccg gcagttggcc    840
agggtgtttt tcgagtccgt ggtgctgacc aacctgactg gcaaggtgtg gtcgcctca    900 gaagcctggg ccctctccag gcacatcact ggggtgcccg ggatccagcg cattgggatg    960
gtgctgggcg tggccatcca gaagagggct gtccctggcc tgaaggcgtt tgaagaagcc   1020
tatgcccggg cagacaagaa ggcccctagg ccttgccaca agggctcctg gtgcagcagc   1080
aatcagctct gcagagaatg ccaagctttc atggcacaca cgatgcccaa gctcaaagcc   1140
ttctccatga gttctgccta caacgcatac cgggctgtgt atgcggtggc ccatggcctc   1200
caccagctcc tgggctgtgc ctctggagct tgttccaggg gccgagtcta cccctggcag   1260
cttttggagc agatccacaa ggtgcatttc cttctacaca aggacactgt ggcgtttaat   1320
gacaacagag atccccctcag tagctataac ataattgcct gggactggaa tggacccaag   1380
tggaccttca cggtcctcgg ttcctccaca tggtctccag ttcagctaaa cataaatgag   1440
accaaaatcc agtggcacgg aaaggacaac caggtgccta agtctgtgtg ttccagcgac   1500
tgtcttgaag gcaccagcg agtggttacg ggtttccatc actgctgctt tgagtgtgtg   1560
ccctgtgggg ctgggacctt cctcaacaag agtgacctct acagatgcca gccttgtggg   1620
aaagaagagt gggcacctga gggaagccag acctgcttcc cgcgcactgt ggtgttttg   1680 gctttgcgtg agcacacctc ttgggtgctg ctggcagcta acacgctgct gctgctgctg   1740
ctgcttggga ctgctggcct gtttgcctgg cacctagaca cccctgtggt gaggtcagca   1800
gggggccgcc tgtgctttct tatgctgggc tccctggcag caggtagtgg cagcctctat   1860
ggcttctttg gggaacccac aaggcctgcg tgcttgctac gccaggccct ctttgccctt   1920
ggtttcacca tcttcctgtc ctgcctgaca gttcgctcat ccaactaat catcatcttc   1980 ttgttttcca ccaaggtacc tacattctac cacgcctggg tccaaaacca cggtgctggc   2040
ctgtttgtga tgatcagctc agcggcccag ctgcttatct gtctaacttg gctggtggtg   2100
tggaccccac tgcctgctag ggaataccag cgcttccccc atctggtgat gcttgagtgc   2160
acagagacca actccctggg cttcatactg gccttcctct acaatggcct cctctccatc   2220
agtgcctttg cctgcagcta cctgggtaag gacttgccag agaactacaa cgaggccaaa   2280
tgtgtcacct tcagcctgct cttcaacttc gtgtcctgga tcgccttctt caccacggcc   2340
agcgtctacg acggcaagta cctgcctgcg gccaacatga tggctgggct gagcagcctg   2400
agcagcggct tcggtgggta ttttctgcct aagtgctacg tgatcctctg ccgcccagac   2460
ctcaacagca cagagcactt ccaggcctcc attcaggact acacgaggcg ctgcggctcc   2520
acctga                                                               2526
```

<210> SEQ ID NO 7
<211> LENGTH: 841
<212> TYPE: PRT
<213> ORGANISM: Homo sapiens

<400> SEQUENCE: 7

Met Leu Leu Cys Thr Ala Arg Leu Val Gly Leu Gln Leu Leu Ile Ser
 1               5                  10                  15

Cys Cys Trp Ala Phe Ala Cys His Ser Thr Glu Ser Ser Pro Asp Phe
            20                  25                  30

```
Thr Leu Pro Gly Asp Tyr Leu Leu Ala Gly Leu Phe Pro Leu His Ser
         35                  40                  45

Gly Cys Leu Gln Val Arg His Arg Pro Glu Val Thr Leu Cys Asp Arg
 50                  55                  60

Ser Cys Ser Phe Asn Glu His Gly Tyr His Leu Phe Gln Ala Met Arg
 65                  70                  75                  80

Leu Gly Val Glu Glu Ile Asn Asn Ser Thr Ala Leu Leu Pro Asn Ile
                 85                  90                  95

Thr Leu Gly Tyr Gln Leu Tyr Asp Val Cys Ser Asp Ser Ala Asn Val
            100                 105                 110

Tyr Ala Thr Leu Arg Val Leu Ser Leu Pro Gly Gln His Ile Glu
        115                 120                 125

Leu Gln Gly Asp Leu Leu His Tyr Ser Pro Thr Val Leu Ala Val Ile
    130                 135                 140

Gly Pro Asp Ser Thr Asn Arg Ala Ala Thr Thr Ala Ala Leu Leu Ser
145                 150                 155                 160

Pro Phe Leu Val Pro Met Ile Ser Tyr Ala Ala Ser Ser Glu Thr Leu
                165                 170                 175

Ser Val Lys Arg Gln Tyr Pro Ser Phe Leu Arg Thr Ile Pro Asn Asp
            180                 185                 190

Lys Tyr Gln Val Glu Thr Met Val Leu Leu Leu Gln Lys Phe Gly Trp
        195                 200                 205

Thr Trp Ile Ser Leu Val Gly Ser Ser Asp Asp Tyr Gly Gln Leu Gly
    210                 215                 220

Val Gln Ala Leu Glu Asn Gln Ala Thr Gly Gln Gly Ile Cys Ile Ala
225                 230                 235                 240

Phe Lys Asp Ile Met Pro Phe Ser Ala Gln Val Gly Asp Glu Arg Met
                245                 250                 255

Gln Cys Leu Met Arg His Leu Ala Gln Ala Gly Ala Thr Val Val Val
            260                 265                 270

Val Phe Ser Ser Arg Gln Leu Ala Arg Val Phe Phe Glu Ser Val Val
        275                 280                 285

Leu Thr Asn Leu Thr Gly Lys Val Trp Val Ala Ser Glu Ala Trp Ala
    290                 295                 300

Leu Ser Arg His Ile Thr Gly Val Pro Gly Ile Gln Arg Ile Gly Met
305                 310                 315                 320

Val Leu Gly Val Ala Ile Gln Lys Arg Ala Val Pro Gly Leu Lys Ala
                325                 330                 335

Phe Glu Glu Ala Tyr Ala Arg Ala Asp Lys Lys Ala Pro Arg Pro Cys
            340                 345                 350

His Lys Gly Ser Trp Cys Ser Ser Asn Gln Leu Cys Arg Glu Cys Gln
        355                 360                 365

Ala Phe Met Ala His Thr Met Pro Lys Leu Lys Ala Phe Ser Met Ser
    370                 375                 380

Ser Ala Tyr Asn Ala Tyr Arg Ala Val Tyr Ala Val Ala His Gly Leu
385                 390                 395                 400

His Gln Leu Leu Gly Cys Ala Ser Gly Ala Cys Ser Arg Gly Arg Val
                405                 410                 415

Tyr Pro Trp Gln Leu Leu Glu Gln Ile His Lys Val His Phe Leu Leu
            420                 425                 430

His Lys Asp Thr Val Ala Phe Asn Asp Asn Arg Asp Pro Leu Ser Ser
        435                 440                 445

Tyr Asn Ile Ile Ala Trp Asp Trp Asn Gly Pro Lys Trp Thr Phe Thr
```

-continued

```
            450                 455                 460
Val Leu Gly Ser Ser Thr Trp Ser Pro Val Gln Leu Asn Ile Asn Glu
465                 470                 475                 480

Thr Lys Ile Gln Trp His Gly Lys Asp Asn Gln Val Pro Lys Ser Val
                485                 490                 495

Cys Ser Ser Asp Cys Leu Glu Gly His Gln Arg Val Val Thr Gly Phe
                500                 505                 510

His His Cys Cys Phe Glu Cys Val Pro Cys Gly Ala Gly Thr Phe Leu
                515                 520                 525

Asn Lys Ser Asp Leu Tyr Arg Cys Gln Pro Cys Gly Lys Glu Glu Trp
                530                 535                 540

Ala Pro Glu Gly Ser Gln Thr Cys Phe Pro Arg Thr Val Val Phe Leu
545                 550                 555                 560

Ala Leu Arg Glu His Thr Ser Trp Val Leu Leu Ala Ala Asn Thr Leu
                565                 570                 575

Leu Leu Leu Leu Leu Leu Gly Thr Ala Gly Leu Phe Ala Trp His Leu
                580                 585                 590

Asp Thr Pro Val Val Arg Ser Ala Gly Gly Arg Leu Cys Phe Leu Met
                595                 600                 605

Leu Gly Ser Leu Ala Ala Gly Ser Gly Ser Leu Tyr Gly Phe Phe Gly
610                 615                 620

Glu Pro Thr Arg Pro Ala Cys Leu Leu Arg Gln Ala Leu Phe Ala Leu
625                 630                 635                 640

Gly Phe Thr Ile Phe Leu Ser Cys Leu Thr Val Arg Ser Phe Gln Leu
                645                 650                 655

Ile Ile Ile Phe Lys Phe Ser Thr Lys Val Pro Thr Phe Tyr His Ala
                660                 665                 670

Trp Val Gln Asn His Gly Ala Gly Leu Phe Val Met Ile Ser Ser Ala
                675                 680                 685

Ala Gln Leu Leu Ile Cys Leu Thr Trp Leu Val Val Trp Thr Pro Leu
                690                 695                 700

Pro Ala Arg Glu Tyr Gln Arg Phe Pro His Leu Val Met Leu Glu Cys
705                 710                 715                 720

Thr Glu Thr Asn Ser Leu Gly Phe Ile Leu Ala Phe Leu Tyr Asn Gly
                725                 730                 735

Leu Leu Ser Ile Ser Ala Phe Ala Cys Ser Tyr Leu Gly Lys Asp Leu
                740                 745                 750

Pro Glu Asn Tyr Asn Glu Ala Lys Cys Val Thr Phe Ser Leu Leu Phe
                755                 760                 765

Asn Phe Val Ser Trp Ile Ala Phe Phe Thr Thr Ala Ser Val Tyr Asp
                770                 775                 780

Gly Lys Tyr Leu Pro Ala Ala Asn Met Met Ala Gly Leu Ser Ser Leu
785                 790                 795                 800

Ser Ser Gly Phe Gly Gly Tyr Phe Leu Pro Lys Cys Tyr Val Ile Leu
                805                 810                 815

Cys Arg Pro Asp Leu Asn Ser Thr Glu His Phe Gln Ala Ser Ile Gln
                820                 825                 830

Asp Tyr Thr Arg Arg Cys Gly Ser Thr
                835                 840

<210> SEQ ID NO 8
<211> LENGTH: 2523
<212> TYPE: DNA
<213> ORGANISM: Rattus sp.
```

<400> SEQUENCE: 8

```
atgctcttct gggctgctca cctgctgctc agcctgcagt tggtctactg ctgggctttc      60
agctgccaaa ggacagagtc ctctccaggc ttcagccttc ctggggactt cctccttgca     120
ggtctgttct ccctccatgg tgactgtctg caggtgagac acagacctct ggtgacaagt     180
tgtgacaggc ccgacagctt caacggccat ggctaccacc tcttccaagc catgcggttc     240
actgttgagg agataaacaa ctcctcggcc ctgcttccca acatcaccct ggggtatgag     300
ctgtacgacg tgtgctcaga atctgccaat gtgtatgcca ccctgagggt gcttgccctg     360
caagggcccc gccacataga gatacagaaa gaccttcgca accactcctc caaggtggtg     420
gccttcatcg ggcctgacaa cactgaccac gctgtcacta ccgctgcctt gctgggtcct     480
ttcctgatgc ccctggtcag ctatgaggca agcagcgtgg tactcagtgc caagcgcaag     540
ttcccgtctt ccttcgtac cgtccccagt gaccggcacc aggtggaggt catggtgcag     600
ctgctgcaga gttttgggtg ggtgtggatc tcgctcattg gcagctacgg tgattacggg     660
cagctgggtg tgcaggcgct ggaggagctg gccgtgcccc ggggcatctg cgtcgccttc     720
aaggacatcg tgcctttctc tgcccgggtg ggtgacccga ggatgcagag catgatgcag     780
catctggctc aggccaggac caccgtggtt gtggtcttct ctaaccggca cctggctaga     840
gtgttcttca ggtccgtggt gctggccaac ctgactggca aagtgtgggt cgcctcagaa     900
gactgggcca tctccacgta catcaccagc gtgactggga tccaaggcat gggacggtg     960
ctcggtgtgg ccgtccagca gagacaagtc cctgggctga aggagtttga ggagtcttat    1020
gtcagggctg taacagctgc tcccagcgct tgcccggagg ggtcctggtg cagcactaac    1080
cagctgtgcc gggagtgcca cacgttcacg actcgtaaca tgcccacgct ggagccttc    1140
tccatgagtg ccgcctacag agtgtatgag ctgtgtacg ctgtggccca cggcctccac    1200
cagctcctgg gatgtacttc tgagatctgt tccagaggcc cagtctaccc ctggcagctt    1260
cttcagcaga tctacaaggt gaattttctt ctacatgaga atactgtggc atttgatgac    1320
aacggggaca ctctaggtta ctacgacatc atcgcctggg actggaatgg acctgaatgg    1380
acctttgaga tcattggctc tgcctcactg tctccagttc atctggacat aaataagaca    1440
aaaatccagt ggcacgggaa gaacaatcag gtgcctgtgt cagtgtgtac cacggactgt    1500
ctggcagggc accacagggt ggttgtgggt tccaccact gctgctttga gtgtgtgccc    1560
tgcgaagctg ggacctttct caacatgagt gagcttcaca tctgccagcc ttgtggaaca    1620
gaagaatggg cacccaagga gagcactact tgcttccac gcacggtgga gttcttggct    1680
tggcatgaac ccatctcttt ggtgctaata gcagctaaca cgctattgct gctgctgctg    1740
gttgggactg ctggcctgtt tgcctggcat tttcacacac ctgtagtgag gtcagctggg    1800
ggtaggctgt gcttcctcat gctgggttcc ctggtggccg gaagttgcag cttctatagc    1860
ttcttcgggg agcccacggt gccgcgtgc ttgctgcgtc agcccctctt ttctctcggg    1920
tttgccatct tcctctcctg cctgacaatc cgctccttcc aactggtcat catcttcaag    1980
ttttctacca aggtgcccac attctaccgt acctgggccc aaaaccatgg tgcaggtcta    2040
ttcgtcattg tcagctccac ggtccatttg ctcatctgtc tcacatggct tgtaatgtgg    2100
accccacgac ccaccaggga ataccagcgc ttccccatc tggtgattct cgagtgcaca    2160
gaggtcaact ctgtaggctt cctgttggct ttcacccaca acattctcct ctccatcagt    2220
accttcgtct gcagctacct gggtaaggaa ctgccagaga actataatga agccaaatgt    2280
gtcaccttca gcctgctcct caacttcgta tcctggatcg ccttcttcac catggccagc    2340
```

```
atttaccagg gcagctacct gcctgcggtc aatgtgctgg cagggctgac cacactgagc    2400
ggcggcttca gcggttactt cctccccaag tgctatgtga ttctctgccg tccagaactc    2460
aacaatacag aacactttca ggcctccatc caggactaca cgaggcgctg cggcactacc    2520
tga                                                                  2523
```

<210> SEQ ID NO 9
<211> LENGTH: 840
<212> TYPE: PRT
<213> ORGANISM: Rattus sp.

<400> SEQUENCE: 9

```
Met Leu Phe Trp Ala Ala His Leu Leu Ser Leu Gln Leu Val Tyr
 1               5                  10                  15

Cys Trp Ala Phe Ser Cys Gln Arg Thr Glu Ser Ser Pro Gly Phe Ser
            20                  25                  30

Leu Pro Gly Asp Phe Leu Leu Ala Gly Leu Phe Ser Leu His Gly Asp
        35                  40                  45

Cys Leu Gln Val Arg His Arg Pro Leu Val Thr Ser Cys Asp Arg Pro
    50                  55                  60

Asp Ser Phe Asn Gly His Gly Tyr His Leu Phe Gln Ala Met Arg Phe
65                  70                  75                  80

Thr Val Glu Glu Ile Asn Asn Ser Ser Ala Leu Leu Pro Asn Ile Thr
                85                  90                  95

Leu Gly Tyr Glu Leu Tyr Asp Val Cys Ser Glu Ser Ala Asn Val Tyr
            100                 105                 110

Ala Thr Leu Arg Val Leu Ala Leu Gln Gly Pro Arg His Ile Glu Ile
        115                 120                 125

Gln Lys Asp Leu Arg Asn His Ser Ser Lys Val Ala Phe Ile Gly
    130                 135                 140

Pro Asp Asn Thr Asp His Ala Val Thr Ala Ala Leu Leu Gly Pro
145                 150                 155                 160

Phe Leu Met Pro Leu Val Ser Tyr Glu Ala Ser Ser Val Val Leu Ser
                165                 170                 175

Ala Lys Arg Lys Phe Pro Ser Phe Leu Arg Thr Val Pro Ser Asp Arg
            180                 185                 190

His Gln Val Glu Val Met Val Gln Leu Leu Gln Ser Phe Gly Trp Val
        195                 200                 205

Trp Ile Ser Leu Ile Gly Ser Tyr Gly Asp Tyr Gly Gln Leu Gly Val
    210                 215                 220

Gln Ala Leu Glu Glu Leu Ala Val Pro Arg Gly Ile Cys Val Ala Phe
225                 230                 235                 240

Lys Asp Ile Val Pro Phe Ser Ala Arg Val Gly Asp Pro Arg Met Gln
                245                 250                 255

Ser Met Met Gln His Leu Ala Gln Ala Arg Thr Thr Val Val Val
            260                 265                 270

Phe Ser Asn Arg His Leu Ala Arg Val Phe Phe Arg Ser Val Val Leu
        275                 280                 285

Ala Asn Leu Thr Gly Lys Val Trp Val Ala Ser Glu Asp Trp Ala Ile
    290                 295                 300

Ser Thr Tyr Ile Thr Ser Val Thr Gly Ile Gln Gly Ile Gly Thr Val
305                 310                 315                 320

Leu Gly Val Ala Val Gln Gln Arg Gln Val Pro Gly Leu Lys Glu Phe
                325                 330                 335

Glu Glu Ser Tyr Val Arg Ala Val Thr Ala Ala Pro Ser Ala Cys Pro
```

```
            340             345             350
Glu Gly Ser Trp Cys Ser Thr Asn Gln Leu Cys Arg Glu Cys His Thr
        355                 360                 365

Phe Thr Thr Arg Asn Met Pro Thr Leu Gly Ala Phe Ser Met Ser Ala
    370                 375                 380

Ala Tyr Arg Val Tyr Glu Ala Val Tyr Ala Val Ala His Gly Leu His
385                 390                 395                 400

Gln Leu Leu Gly Cys Thr Ser Glu Ile Cys Ser Arg Gly Pro Val Tyr
                405                 410                 415

Pro Trp Gln Leu Leu Gln Gln Ile Tyr Lys Val Asn Phe Leu Leu His
            420                 425                 430

Glu Asn Thr Val Ala Phe Asp Asp Asn Gly Asp Thr Leu Gly Tyr Tyr
        435                 440                 445

Asp Ile Ile Ala Trp Asp Trp Asn Gly Pro Glu Trp Thr Phe Glu Ile
    450                 455                 460

Ile Gly Ser Ala Ser Leu Ser Pro Val His Leu Asp Ile Asn Lys Thr
465                 470                 475                 480

Lys Ile Gln Trp His Gly Lys Asn Asn Gln Val Pro Val Ser Val Cys
                485                 490                 495

Thr Thr Asp Cys Leu Ala Gly His His Arg Val Val Gly Ser His
            500                 505                 510

His Cys Cys Phe Glu Cys Val Pro Cys Glu Ala Gly Thr Phe Leu Asn
    515                 520                 525

Met Ser Glu Leu His Ile Cys Gln Pro Cys Gly Thr Glu Glu Trp Ala
    530                 535                 540

Pro Lys Glu Ser Thr Thr Cys Phe Pro Arg Thr Val Glu Phe Leu Ala
545                 550                 555                 560

Trp His Glu Pro Ile Ser Leu Val Leu Ile Ala Ala Asn Thr Leu Leu
                565                 570                 575

Leu Leu Leu Leu Val Gly Thr Ala Gly Leu Phe Ala Trp His Phe His
            580                 585                 590

Thr Pro Val Val Arg Ser Ala Gly Gly Arg Leu Cys Phe Leu Met Leu
        595                 600                 605

Gly Ser Leu Val Ala Gly Ser Cys Ser Phe Tyr Ser Phe Phe Gly Glu
    610                 615                 620

Pro Thr Val Pro Ala Cys Leu Leu Arg Gln Pro Leu Phe Ser Leu Gly
625                 630                 635                 640

Phe Ala Ile Phe Leu Ser Cys Leu Thr Ile Arg Ser Phe Gln Leu Val
                645                 650                 655

Ile Ile Phe Lys Phe Ser Thr Lys Val Pro Thr Phe Tyr Arg Thr Trp
            660                 665                 670

Ala Gln Asn His Gly Ala Gly Leu Phe Val Ile Val Ser Ser Thr Val
        675                 680                 685

His Leu Leu Ile Cys Leu Thr Trp Leu Val Met Trp Thr Pro Arg Pro
    690                 695                 700

Thr Arg Glu Tyr Gln Arg Phe Pro His Leu Val Ile Leu Glu Cys Thr
705                 710                 715                 720

Glu Val Asn Ser Val Gly Phe Leu Leu Ala Phe Thr His Asn Ile Leu
                725                 730                 735

Leu Ser Ile Ser Thr Phe Val Cys Ser Tyr Leu Gly Lys Glu Leu Pro
            740                 745                 750

Glu Asn Tyr Asn Glu Ala Lys Cys Val Thr Phe Ser Leu Leu Leu Asn
        755                 760                 765
```

-continued

```
              Phe Val Ser Trp Ile Ala Phe Phe Thr Met Ala Ser Ile Tyr Gln Gly
                      770                 775                 780

Ser Tyr Leu Pro Ala Val Asn Val Leu Ala Gly Leu Thr Thr Leu Ser
              785                 790                 795                 800

Gly Gly Phe Ser Gly Tyr Phe Leu Pro Lys Cys Tyr Val Ile Leu Cys
                              805                 810                 815

Arg Pro Glu Leu Asn Asn Thr Glu His Phe Gln Ala Ser Ile Gln Asp
                          820                 825                 830

Tyr Thr Arg Arg Cys Gly Thr Thr
                          835                 840

<210> SEQ ID NO 10
<211> LENGTH: 2520
<212> TYPE: DNA
<213> ORGANISM: Homo sapiens

<400> SEQUENCE: 10 atgggccca gggcaaagac catctgctcc ctgttcttcc tcctatgggt cctggctgag      60
ccggctgaga actcggactt ctacctgcct ggggattacc tcctgggtgg cctcttctcc    120
ctccatgcca acatgaaggg cattgttcac cttaacttcc tgcaggtgcc catgtgcaag    180
gagtatgaag tgaaggtgat aggctacaac ctcatgcagg ccatgcgctt cgcggtggag    240
gagatcaaca atgacagcag cctgctgcct ggtgtgctgc tgggctatga gatcgtggat    300
gtgtgctaca tctccaacaa tgtccagccg gtgctctact tcctggcaca cgaggacaac    360
ctccttccca tccaagagga ctacagtaac tacatttccc gtgtggtggc tgtcattggc    420
cctgacaact ccgagtctgt catgactgtg ccaacttcc tctccctatt tctccttcca    480
cagatcacct cagcgccat cagcgatgag ctgcgagaca aggtgcgctt ccggctttg    540 ctgcgtacca cccagcgc cgaccaccac gtcgaggcca tggtgcagct gatgctgcac    600
ttccgctgga actggatcat tgtgctggtg agcagcgaca cctatggccg cgacaatggc    660
cagctgcttg gcgagcgcgt ggcccggcgc gacatctgca tcgccttcca ggagacgctg    720
cccacactgc agcccaacca gaacatgacg tcagaggagc gccagcgcct ggtgaccatt    780
gtggacaagc tgcagcagag cacagcgcgc gtcgtggtcg tgttctcgcc cgacctgacc    840
ctgtaccact tcttcaatga ggtgctgcgc agaacttca cggcgccgt gtggatcgcc    900 tccgagtcct gggccatcga cccggtcctg cacaacctca cggagctggg ccacttgggc    960
accttcctgg gcatcaccat ccagagcgtg cccatcccgg cttcagtga gttccgcgag   1020 tggggcccac aggctgggcc gccaccctc agcaggacca gccagagcta cctgcaac    1080 caggagtgcg acaactgcct gaacgccacc ttgtccttca caccattct caggctctct   1140 ggggagcgtg tcgtctacag cgtgtactct gcggtctatg ctgtgcccca tgccctgcac   1200
agcctcctcg gctgtgacaa agcacctgc accaagaggg tggtctaccc ctggcagctg   1260
cttgaggaga tctggaaggt caacttcact ctcctggacc accaaatctt cttcgacccg   1320
caaggggacg tggctctgca cttggagatt gtccagtggc aatgggaccg gagccagaat   1380
cccttccaga gcgtcgcctc ctactacccc ctgcagcgac agctgaagaa catccaagac   1440
atctcctggc acaccgtcaa caacacgatc cctatgtcca tgtgttccaa gaggtgccag   1500
tcagggcaaa agaagaagcc tgtgggcatc acgtctgct gcttcgagtg catcgactgc   1560
cttcccggca ccttcctcaa ccacactgaa gatgaatatg aatgccagc tgccgcgaat   1620 aacgagtggt cctaccagag tgagacctcc tgcttcaagc ggcagctggt cttcctggaa   1680
tggcatgagg cacccaccat cgctgtggcc ctgctggccg ccctgggctt cctcagcacc   1740
```

```
ctggccatcc tggtgatatt ctggaggcac ttccagacac ccatagttcg ctcggctggg    1800
ggccccatgt gcttcctgat gctgacactg ctgctggtgg catacatggt ggtcccggtc    1860
tacgtggggc cgcccaaggt ctccacctgc ctctgccgcc aggccctctt tcccctctgc    1920
ttcacaattt gcatctcctg tatcgccgtg cgttctttcc agatcgtctg cgccttcaag    1980
atggccagcc gcttcccacg cgcctacagc tactgggtcc gctaccaggg ccctacgtc    2040 tctatggcat ttatcacggt actcaaaatg gtcattgtgg taattggcat gctggccacg    2100
ggcctcagtc ccaccacccg tactgacccc gatgacccca agatcacaat tgtctcctgt    2160
aaccccaact accgcaacag cctgctgttc aacaccagcc tggacctgct gctctcagtg    2220
gtgggtttca gcttcgccta catgggcaaa gagctgccca ccaactacaa cgaggccaag    2280
ttcatcaccc tcagcatgac cttctatttc acctcatccg tctccctctg caccttcatg    2340
tctgcctaca gcggggtgct ggtcaccatc gtggacctct tggtcactgt gctcaacctc    2400
ctggccatca gcctgggcta cttcggcccc aagtgctaca tgatcctctt ctacccggag    2460
cgcaacacgc ccgcctactt caacagcatg atccagggct acaccatgag gagggactag    2520
```

<210> SEQ ID NO 11
<211> LENGTH: 839
<212> TYPE: PRT
<213> ORGANISM: Homo sapiens

<400> SEQUENCE: 11

```
Met Gly Pro Arg Ala Lys Thr Ile Cys Ser Leu Phe Phe Leu Leu Trp
  1               5                  10                  15

Val Leu Ala Glu Pro Ala Glu Asn Ser Asp Phe Tyr Leu Pro Gly Asp
             20                  25                  30

Tyr Leu Gly Gly Leu Phe Ser Leu His Ala Asn Met Lys Gly Ile
         35                  40                  45

Val His Leu Asn Phe Leu Gln Val Pro Met Cys Lys Glu Tyr Glu Val
     50                  55                  60

Lys Val Ile Gly Tyr Asn Leu Met Gln Ala Met Arg Phe Ala Val Glu
 65                  70                  75                  80

Glu Ile Asn Asn Asp Ser Ser Leu Leu Pro Gly Val Leu Leu Gly Tyr
                 85                  90                  95

Glu Ile Val Asp Val Cys Tyr Ile Ser Asn Asn Val Gln Pro Val Leu
            100                 105                 110

Tyr Phe Leu Ala His Glu Asp Asn Leu Leu Pro Ile Gln Gly Asp Tyr
        115                 120                 125

Ser Asn Tyr Ile Ser Arg Val Val Ala Val Ile Gly Pro Asp Asn Ser
    130                 135                 140

Glu Ser Val Met Thr Val Ala Asn Phe Leu Ser Leu Phe Leu Leu Pro
145                 150                 155                 160

Gln Ile Thr Tyr Ser Ala Ile Ser Asp Glu Leu Arg Asp Lys Val Arg
                165                 170                 175

Phe Pro Ala Leu Leu Arg Thr Thr Pro Ser Ala Asp His His Val Glu
            180                 185                 190

Ala Met Val Gln Leu Met Leu His Phe Arg Trp Asn Trp Ile Ile Val
        195                 200                 205

Leu Val Ser Ser Asp Thr Tyr Gly Arg Asp Asn Gly Gln Leu Leu Gly
    210                 215                 220

Glu Arg Val Ala Arg Arg Asp Ile Cys Ile Ala Phe Gln Glu Thr Leu
225                 230                 235                 240
```

-continued

```
Pro Thr Leu Gln Pro Asn Gln Asn Met Thr Ser Glu Glu Arg Gln Arg
                245                 250                 255

Leu Val Thr Ile Val Asp Lys Leu Gln Gln Ser Thr Ala Arg Val Val
            260                 265                 270

Val Val Phe Ser Pro Asp Leu Thr Leu Tyr His Phe Phe Asn Glu Val
        275                 280                 285

Leu Arg Gln Asn Phe Thr Gly Ala Val Trp Ile Ala Ser Glu Ser Trp
    290                 295                 300

Ala Ile Asp Pro Val Leu His Asn Leu Thr Glu Leu Gly His Leu Gly
305                 310                 315                 320

Thr Phe Leu Gly Ile Thr Ile Gln Ser Val Pro Ile Pro Gly Phe Ser
                325                 330                 335

Glu Phe Arg Glu Trp Gly Pro Gln Ala Gly Pro Pro Leu Ser Arg
            340                 345                 350

Thr Ser Gln Ser Tyr Thr Cys Asn Gln Glu Cys Asp Asn Cys Leu Asn
        355                 360                 365

Ala Thr Leu Ser Phe Asn Thr Ile Leu Arg Leu Ser Gly Glu Arg Val
    370                 375                 380

Val Tyr Ser Val Tyr Ser Ala Val Tyr Ala Val Ala His Ala Leu His
385                 390                 395                 400

Ser Leu Leu Gly Cys Asp Lys Ser Thr Cys Thr Lys Arg Val Val Tyr
                405                 410                 415

Pro Trp Gln Leu Leu Glu Glu Ile Trp Lys Val Asn Phe Thr Leu Leu
            420                 425                 430

Asp His Gln Ile Phe Phe Asp Pro Gln Gly Asp Val Ala Leu His Leu
        435                 440                 445

Glu Ile Val Gln Trp Gln Trp Asp Arg Ser Gln Asn Pro Phe Gln Ser
    450                 455                 460

Val Ala Ser Tyr Tyr Pro Leu Gln Arg Gln Leu Lys Asn Ile Gln Asp
465                 470                 475                 480

Ile Ser Trp His Thr Val Asn Asn Thr Ile Pro Met Ser Met Cys Ser
                485                 490                 495

Lys Arg Cys Gln Ser Gly Gln Lys Lys Lys Pro Val Gly Ile His Val
            500                 505                 510

Cys Cys Phe Glu Cys Ile Asp Cys Leu Pro Gly Thr Phe Leu Asn His
        515                 520                 525

Thr Glu Asp Glu Tyr Glu Cys Gln Ala Cys Pro Asn Asn Glu Trp Ser
    530                 535                 540

Tyr Gln Ser Glu Thr Ser Cys Phe Lys Arg Gln Leu Val Phe Leu Glu
545                 550                 555                 560

Trp His Glu Ala Pro Thr Ile Ala Val Ala Leu Leu Ala Ala Leu Gly
                565                 570                 575

Phe Leu Ser Thr Leu Ala Ile Leu Val Ile Phe Trp Arg His Phe Gln
            580                 585                 590

Thr Pro Ile Val Arg Ser Ala Gly Gly Pro Met Cys Phe Leu Met Leu
        595                 600                 605

Thr Leu Leu Leu Val Ala Tyr Met Val Val Pro Val Tyr Val Gly Pro
    610                 615                 620

Pro Lys Val Ser Thr Cys Leu Cys Arg Gln Ala Leu Phe Pro Leu Cys
625                 630                 635                 640

Phe Thr Ile Cys Ile Ser Cys Ile Ala Val Arg Ser Phe Gln Ile Val
                645                 650                 655

Cys Ala Phe Lys Met Ala Ser Arg Phe Pro Arg Ala Tyr Ser Tyr Trp
            660                 665                 670
```

```
Val Arg Tyr Gln Gly Pro Tyr Val Ser Met Ala Phe Ile Thr Val Leu
            675                 680                 685

Lys Met Val Ile Val Val Ile Gly Met Leu Ala Thr Gly Leu Ser Pro
690                 695                 700

Thr Thr Arg Thr Asp Pro Asp Asp Pro Lys Ile Thr Ile Val Ser Cys
705                 710                 715                 720

Asn Pro Asn Tyr Arg Asn Ser Leu Leu Phe Asn Thr Ser Leu Asp Leu
            725                 730                 735

Leu Leu Ser Val Val Gly Phe Ser Phe Ala Tyr Met Gly Lys Glu Leu
            740                 745                 750

Pro Thr Asn Tyr Asn Glu Ala Lys Phe Ile Thr Leu Ser Met Thr Phe
            755                 760                 765

Tyr Phe Thr Ser Ser Val Ser Leu Cys Thr Phe Met Ser Ala Tyr Ser
            770                 775                 780

Gly Val Leu Val Thr Ile Val Asp Leu Leu Val Thr Val Leu Asn Leu
785                 790                 795                 800

Leu Ala Ile Ser Leu Gly Tyr Phe Gly Pro Lys Cys Tyr Met Ile Leu
                805                 810                 815

Phe Tyr Pro Glu Arg Asn Thr Pro Ala Tyr Phe Asn Ser Met Ile Gln
            820                 825                 830

Gly Tyr Thr Met Arg Arg Asp
        835
```

<210> SEQ ID NO 12
<211> LENGTH: 2529
<212> TYPE: DNA
<213> ORGANISM: Rattus sp.

<400> SEQUENCE: 12

```
atgggtcccc aggcaaggac actctgcttg ctgtctctcc tgctgcatgt tctgcctaag      60
ccaggcaagc tggtagagaa ctctgacttc cacctggccg ggactacct cctgggtggc     120
ctctttaccc tccatgccaa cgtgaagagc atctcccacc tcagctacct gcaggtgccc     180
aagtgcaatg agttcaccat gaaggtgttg gctacaacc tcatgcaggc catgcgtttc     240
gctgtggagg agatcaacaa ctgtagctcc ctgctacccg cgtgctgct cggctacgag     300
atggtggatg tctgttacct ctccaacaat atccaccctg gctctactt cctggcacag     360
gacgacgacc tcctgcccat cctcaaagac tacagccagt acatgcccca cgtggtggct     420
gtcattggcc ccgacaactc tgagtccgcc attaccgtgt ccaacattct ctctcatttc     480
ctcatcccac agatcacata cagcgccatc tccgacaagc tgcgggacaa cggcacttc     540
cctagcatgc tacgcacagt gcccagcgcc acccaccaca tcgaggccat ggtgcagctg     600
atggttcact ccaatggaa ctggattgtg tgctggtga cgacgacga ttacggccgc     660
gagaacagcc acctgttgag ccagcgtctg accaaaacga cgacatctg cattgccttc     720
caggaggttc tgcccatacc tgagtccagc caggtcatga ggtccgagga gcagagacaa     780
ctggacaaca tcctggacaa gctgcggcgg acctcggcgc gcgtcgtggt ggtgttctcg     840
cccgagctga gcctgtatag cttctttcac gaggtgctcc gctggaactt cacgggtttt     900
gtgtggatcg cctctgagtc ctgggctatc gacccagttc tgcataacct cacggagctg     960
cgccacacgg gtactttct gggcgtcacc atccagaggg tgtccatccc tggcttcagt    1020
cagttccgag tgcgccgtga caagccaggg tatcccgtgc ctaacacgac caacctgcgg    1080
acgacctgca accaggactg tgacgcctgc ttgaacacca ccagtccctt caacaacatc    1140
```

-continued

```
cttatacttt cggggagcg cgtggtctac agcgtgtact cggcagttta cgcggtggcc    1200
catgccctcc acagactcct cggctgtaac cgggtccgct gcaccaagca aaaggtctac    1260
ccgtggcagc tactcaggga gatctggcac gtcaacttca cgctcctggg taaccggctc    1320
ttctttgacc aacaagggga catgccgatg ctcttggaca tcatccagtg gcagtgggac    1380
ctgagccaga tcccttcca aagcatcgcc tcctattctc ccaccagcaa gaggctaacc    1440
tacattaaca atgtgtcctg gtacaccccc aacaacacgg tccctgtctc catgtgttcc    1500
aagagctgcc agccagggca aatgaaaaag tctgtgggcc tccacccttg ttgcttcgag    1560
tgcttggatt gtatgccagg cacctacctc aaccgctcag cagatgagtt taactgtctg    1620
tcctgcccgg gttccatgtg gtcctacaag aacgacatca cttgcttcca gcggcggcct    1680
accttcctgg agtggcacga agtgccacc atcgtggtgg ccatactggc tgccctgggc    1740
ttcttcagta cactggccat tcttttcatc ttctggagac atttccagac acccatggtg    1800
cgctcggccg gtgcccccat gtgcttcctg atgctcgtgc cctgctgct ggcgtttggg    1860 atggtgcccg tgtatgtggg gcccccacg gtcttctcat gcttctgccg acaggctttc    1920
ttcaccgtct gcttctccat ctgcctatcc tgcatcaccg tgcgctcctt ccagatcgtg    1980
tgtgtcttca agatggccag acgcctgcca agtgcctaca gttttttggat gcgttaccac    2040 gggccctatg tcttcgtggc cttcatcacg gccatcaagg tggccctggt ggtgggcaac    2100
atgctggcca ccaccatcaa ccccattggc cggaccgacc cggatgaccc caacatcatg    2160
atcctctcgt gccacccctaa ctaccgcaac gggctactgt tcaacaccag catggacttg    2220
ctgctgtctg tgctgggttt cagcttcgct tacatgggca aggagctgcc caccaactac    2280
aacgaagcca agttcatcac tctcagcatg accttctcct tcacctcctc catctccctc    2340
tgcaccttca tgtctgtgca cgacggcgtg ctggtcacca tcatggacct cctggtcact    2400
gtgctcaact tcctggccat cggcttggga tactttggcc ccaagtgtta catgatcctt    2460
ttctacccgg agcgcaacac ctcagcctat ttcaatagca tgatccaggg ctacaccatg    2520
aggaagagc                                                           2529
```

<210> SEQ ID NO 13
<211> LENGTH: 843
<212> TYPE: PRT
<213> ORGANISM: Rattus sp.

<400> SEQUENCE: 13

```
Met Gly Pro Gln Ala Arg Thr Leu Cys Leu Leu Ser Leu Leu Leu His
  1               5                  10                  15

Val Leu Pro Lys Pro Gly Lys Leu Val Glu Asn Ser Asp Phe His Leu
                 20                  25                  30

Ala Gly Asp Tyr Leu Leu Gly Gly Leu Phe Thr Leu His Ala Asn Val
             35                  40                  45

Lys Ser Ile Ser His Leu Ser Tyr Leu Gln Val Pro Lys Cys Asn Glu
         50                  55                  60

Phe Thr Met Lys Val Leu Gly Tyr Asn Leu Met Gln Ala Met Arg Phe
     65                  70                  75                  80

Ala Val Glu Glu Ile Asn Asn Cys Ser Ser Leu Leu Pro Gly Val Leu
                 85                  90                  95

Leu Gly Tyr Glu Met Val Asp Val Cys Tyr Leu Ser Asn Asn Ile His
                100                 105                 110

Pro Gly Leu Tyr Phe Leu Ala Gln Asp Asp Asp Leu Leu Pro Ile Leu
            115                 120                 125
```

-continued

```
Lys Asp Tyr Ser Gln Tyr Met Pro His Val Val Ala Val Ile Gly Pro
130                 135                 140

Asp Asn Ser Glu Ser Ala Ile Thr Val Ser Asn Ile Leu Ser His Phe
145                 150                 155                 160

Leu Ile Pro Gln Ile Thr Tyr Ser Ala Ile Ser Asp Lys Leu Arg Asp
                165                 170                 175

Lys Arg His Phe Pro Ser Met Leu Arg Thr Val Pro Ser Ala Thr His
            180                 185                 190

His Ile Glu Ala Met Val Gln Leu Met Val His Phe Gln Trp Asn Trp
        195                 200                 205

Ile Val Val Leu Val Ser Asp Asp Tyr Gly Arg Glu Asn Ser His
210                 215                 220

Leu Leu Ser Gln Arg Leu Thr Lys Thr Ser Asp Ile Cys Ile Ala Phe
225                 230                 235                 240

Gln Glu Val Leu Pro Ile Pro Glu Ser Ser Gln Val Met Arg Ser Glu
                245                 250                 255

Glu Gln Arg Gln Leu Asp Asn Ile Leu Asp Lys Leu Arg Arg Thr Ser
            260                 265                 270

Ala Arg Val Val Val Phe Ser Pro Glu Leu Ser Leu Tyr Ser Phe
        275                 280                 285

Phe His Glu Val Leu Arg Trp Asn Phe Thr Gly Phe Val Trp Ile Ala
290                 295                 300

Ser Glu Ser Trp Ala Ile Asp Pro Val Leu His Asn Leu Thr Glu Leu
305                 310                 315                 320

Arg His Thr Gly Thr Phe Leu Gly Val Thr Ile Gln Arg Val Ser Ile
                325                 330                 335

Pro Gly Phe Ser Gln Phe Arg Val Arg Arg Asp Lys Pro Gly Tyr Pro
            340                 345                 350

Val Pro Asn Thr Thr Asn Leu Arg Thr Thr Cys Asn Gln Asp Cys Asp
        355                 360                 365

Ala Cys Leu Asn Thr Thr Lys Ser Phe Asn Asn Ile Leu Ile Leu Ser
370                 375                 380

Gly Glu Arg Val Val Tyr Ser Val Tyr Ser Ala Val Tyr Ala Val Ala
385                 390                 395                 400

His Ala Leu His Arg Leu Leu Gly Cys Asn Arg Val Arg Cys Thr Lys
                405                 410                 415

Gln Lys Val Tyr Pro Trp Gln Leu Leu Arg Glu Ile Trp His Val Asn
            420                 425                 430

Phe Thr Leu Leu Gly Asn Arg Leu Phe Phe Asp Gln Gln Gly Asp Met
        435                 440                 445

Pro Met Leu Leu Asp Ile Ile Gln Trp Gln Trp Asp Leu Ser Gln Asn
450                 455                 460

Pro Phe Gln Ser Ile Ala Ser Tyr Ser Pro Thr Ser Lys Arg Leu Thr
465                 470                 475                 480

Tyr Ile Asn Asn Val Ser Trp Tyr Thr Pro Asn Asn Thr Val Pro Val
                485                 490                 495

Ser Met Cys Ser Lys Ser Cys Gln Pro Gly Gln Met Lys Lys Ser Val
            500                 505                 510

Gly Leu His Pro Cys Cys Phe Glu Cys Leu Asp Cys Met Pro Gly Thr
        515                 520                 525

Tyr Leu Asn Arg Ser Ala Asp Glu Phe Asn Cys Leu Ser Cys Pro Gly
530                 535                 540

Ser Met Trp Ser Tyr Lys Asn Asp Ile Thr Cys Phe Gln Arg Arg Pro
545                 550                 555                 560
```

```
Thr Phe Leu Glu Trp His Glu Val Pro Thr Ile Val Ala Ile Leu
                565                 570                 575
Ala Ala Leu Gly Phe Ser Thr Leu Ala Ile Leu Phe Ile Phe Trp
            580                 585                 590
Arg His Phe Gln Thr Pro Met Val Arg Ser Ala Gly Gly Pro Met Cys
        595                 600                 605
Phe Leu Met Leu Val Pro Leu Leu Leu Ala Phe Gly Met Val Pro Val
    610                 615                 620
Tyr Val Gly Pro Pro Thr Val Phe Ser Cys Phe Cys Arg Gln Ala Phe
625                 630                 635                 640
Phe Thr Val Cys Phe Ser Ile Cys Leu Ser Cys Ile Thr Val Arg Ser
                645                 650                 655
Phe Gln Ile Val Cys Val Phe Lys Met Ala Arg Arg Leu Pro Ser Ala
            660                 665                 670
Tyr Ser Phe Trp Met Arg Tyr His Gly Pro Tyr Val Phe Val Ala Phe
        675                 680                 685
Ile Thr Ala Ile Lys Val Ala Leu Val Val Gly Asn Met Leu Ala Thr
    690                 695                 700
Thr Ile Asn Pro Ile Gly Arg Thr Asp Pro Asp Pro Asn Ile Met
705                 710                 715                 720
Ile Leu Ser Cys His Pro Asn Tyr Arg Asn Gly Leu Leu Phe Asn Thr
                725                 730                 735
Ser Met Asp Leu Leu Ser Val Leu Gly Phe Ser Phe Ala Tyr Met
            740                 745                 750
Gly Lys Glu Leu Pro Thr Asn Tyr Asn Glu Ala Lys Phe Ile Thr Leu
        755                 760                 765
Ser Met Thr Phe Ser Phe Thr Ser Ile Ser Leu Cys Thr Phe Met
    770                 775                 780
Ser Val His Asp Gly Val Leu Val Thr Ile Met Asp Leu Leu Val Thr
785                 790                 795                 800
Val Leu Asn Phe Leu Ala Ile Gly Leu Gly Tyr Phe Gly Pro Lys Cys
                805                 810                 815
Tyr Met Ile Leu Phe Tyr Pro Glu Arg Asn Thr Ser Ala Tyr Phe Asn
            820                 825                 830
Ser Met Ile Gln Gly Tyr Thr Met Arg Lys Ser
        835                 840

<210> SEQ ID NO 14
<211> LENGTH: 2559
<212> TYPE: DNA
<213> ORGANISM: Homo sapiens

<400> SEQUENCE: 14
atgctgggcc ctgctgtcct gggcctcagc ctctgggctc tcctgcaccc tgggacgggg      60
gccccattgt gcctgtcaca gcaacttagg atgaaggggg actacgtgct gggggggctg     120
ttccccctgg gcgaggccga ggaggctggc ctccgcagcc ggacacggcc cagcagccct     180
gtgtgcacca ggttctcctc aaacggcctg ctctgggcac tggccatgaa atggccgtg      240 gaggagatca acaacaagtc ggatctgctg cccgggctgc gcctgggcta cgacctcttt     300
gatacgtgct cggagcctgt ggtggccatg aagcccagcc tcatgttcct ggccaaggca     360
ggcagccgcg acatcgccgc ctactgcaac tacacgcagt accagccccg tgtgctggct     420
gtcatcgggc ccactcgtc agagctcgcc atggtcaccg caagttctt cagcttcttc       480 ctcatgcccc aggtcagcta cggtgctagc atggagctgc tgagcgcccg ggagaccttc     540
```

```
ccctccttct tccgcaccgt gcccagcgac cgtgtgcagc tgacggccgc cgcggagctg      600
ctgcaggagt tcggctggaa ctgggtggcc gccctgggca gcgacgacga gtacggccgg      660
cagggcctga gcatcttctc ggccctggcc gcggcacgcg gcatctgcat cgcgcacgag      720
ggcctggtgc cgctgccccg tgccgatgac tcgcggctgg ggaaggtgca ggacgtcctg      780
caccaggtga accagagcag cgtgcaggtg gtgctgctgt tcgcctccgt gcacgccgcc      840
cacgccctct tcaactacag catcagcagc aggctctcgc ccaaggtgtg ggtggccagc      900
gaggcctggc tgacctctga cctggtcatg gggctgcccg catggcccca gatgggcacg      960
gtgcttggct tcctccagag gggtgcccag ctgcacgagt tccccagta cgtgaagacg      1020 cacctggccc tggccaccga cccggccttc tgctctgccc tgggcgagag ggagcagggt      1080
ctggaggagg acgtggtggg ccagcgctgc ccgcagtgtg actgcatcac gctgcagaac      1140
gtgagcgcag ggctaaatca ccaccagacg ttctctgtct acgcagctgt gtatagcgtg      1200
gcccaggccc tgcacaacac tcttcagtgc aacgcctcag gctgccccgc gcaggacccc      1260
gtgaagccct ggcagctcct ggagaacatg tacaacctga ccttccacgt gggcgggctg      1320
ccgctgcggt cgacagcag cggaaacgtg acatggagt acgacctgaa gctgtgggtg      1380
tggcagggct cagtgcccag gctccacgac gtgggcaggt tcaacggcag cctcaggaca      1440
gagcgcctga gatccgctg gcacacgtct gacaaccaga agcccgtgtc ccggtgctcg      1500
cggcagtgcc aggagggcca ggtgcgccgg gtcaaggggt tccactcctg ctgctacgac      1560
tgtgtggact gcgaggcggg cagctaccgg caaaacccag acgacatcgc ctgcaccttt      1620
tgtggccagg atgagtggtc cccggagcga agcacacgct gcttccgccg caggtctcgg      1680
ttcctggcat ggggcgagcc ggctgtgctg ctgctgctcc tgctgctgag cctggcgctg      1740
ggccttgtgc tggctgcttt ggggctgttc gttcaccatc gggacagccc actggttcag      1800
gcctcggggg ggcccctggc ctgctttggc ctggtgtgcc tgggcctggt ctgcctcagc      1860
gtcctcctgt tccctggcca gcccagccct gcccgatgcc tggcccagca gcccttgtcc      1920
cacctcccgc tcacgggctg cctgagcaca ctcttcctgc aggcggccga gatcttcgtg      1980
gagtcagaac tgcctctgag ctgggcagac cggctgagtg gctgcctgcg ggggccctgg      2040
gcctggctgg tggtgctgct ggccatgctg gtggaggtcg cactgtgcac ctggtacctg      2100
gtggccttcc cgccggaggt ggtgacggac tggcacatgc tgcccacgga ggcgctggtg      2160
cactgccgca cacgtcctg ggtcagcttc ggcctagcgc acgccaccaa tgccacgctg      2220 gccttctctct gcttcctggg cactttcctg gtgcggagcc agccgggccg ctacaaccgt      2280
gcccgtggcc tcacctttgc catgctggcc tacttcatca cctgggtctc ctttgtgccc      2340
ctcctggcca atgtgcaggt ggtcctcagg cccgccgtgc agatgggcgc cctcctgctc      2400
tgtgtcctgg gcatcctggc tgccttccac ctgcccaggt gttacctgct catgcggcag      2460
ccagggctca acacccccga gttcttcctg ggaggggcc ctggggatgc caaggccag      2520 aatgacggga acacaggaaa tcaggggaaa catgagtga                            2559
```

<210> SEQ ID NO 15
<211> LENGTH: 852
<212> TYPE: PRT
<213> ORGANISM: Homo sapiens

<400> SEQUENCE: 15

Met Leu Gly Pro Ala Val Leu Gly Leu Ser Leu Trp Ala Leu Leu His
1               5                   10                  15

-continued

```
Pro Gly Thr Gly Ala Pro Leu Cys Leu Ser Gln Gln Leu Arg Met Lys
            20                  25                  30
Gly Asp Tyr Val Leu Gly Gly Leu Phe Pro Leu Gly Glu Ala Glu Glu
                35                  40                  45
Ala Gly Leu Arg Ser Arg Thr Arg Pro Ser Ser Pro Val Cys Thr Arg
 50                  55                  60
Phe Ser Ser Asn Gly Leu Leu Trp Ala Leu Ala Met Lys Met Ala Val
 65                  70                  75                  80
Glu Glu Ile Asn Asn Lys Ser Asp Leu Leu Pro Gly Leu Arg Leu Gly
                    85                  90                  95
Tyr Asp Leu Phe Asp Thr Cys Ser Glu Pro Val Val Ala Met Lys Pro
                100                 105                 110
Ser Leu Met Phe Leu Ala Lys Ala Gly Ser Arg Asp Ile Ala Ala Tyr
            115                 120                 125
Cys Asn Tyr Thr Gln Tyr Gln Pro Arg Val Leu Ala Val Ile Gly Pro
130                 135                 140
His Ser Ser Glu Leu Ala Met Val Thr Gly Lys Phe Phe Ser Phe Phe
145                 150                 155                 160
Leu Met Pro Gln Val Ser Tyr Gly Ala Ser Met Glu Leu Leu Ser Ala
                165                 170                 175
Arg Glu Thr Phe Pro Ser Phe Phe Arg Thr Val Pro Ser Asp Arg Val
            180                 185                 190
Gln Leu Thr Ala Ala Ala Glu Leu Leu Gln Glu Phe Gly Trp Asn Trp
        195                 200                 205
Val Ala Leu Gly Ser Asp Asp Glu Tyr Gly Arg Gln Gly Leu Ser
210                 215                 220
Ile Phe Ser Ala Leu Ala Ala Ala Arg Gly Ile Cys Ile Ala His Glu
225                 230                 235                 240
Gly Leu Val Pro Leu Pro Arg Ala Asp Asp Ser Arg Leu Gly Lys Val
                245                 250                 255
Gln Asp Val Leu His Gln Val Asn Gln Ser Ser Val Gln Val Val Leu
            260                 265                 270
Leu Phe Ala Ser Val His Ala Ala His Ala Leu Phe Asn Tyr Ser Ile
        275                 280                 285
Ser Ser Arg Leu Ser Pro Lys Val Trp Val Ala Ser Glu Ala Trp Leu
290                 295                 300
Thr Ser Asp Leu Val Met Gly Leu Pro Gly Met Ala Gln Met Gly Thr
305                 310                 315                 320
Val Leu Gly Phe Leu Gln Arg Gly Ala Gln Leu His Glu Phe Pro Gln
                325                 330                 335
Tyr Val Lys Thr His Leu Ala Leu Ala Thr Asp Pro Ala Phe Cys Ser
            340                 345                 350
Ala Leu Gly Glu Arg Glu Gln Gly Leu Glu Glu Asp Val Val Gly Gln
        355                 360                 365
Arg Cys Pro Gln Cys Asp Cys Ile Thr Leu Gln Asn Val Ser Ala Gly
370                 375                 380
Leu Asn His His Gln Thr Phe Ser Val Tyr Ala Ala Val Tyr Ser Val
385                 390                 395                 400
Ala Gln Ala Leu His Asn Thr Leu Gln Cys Asn Ala Ser Gly Cys Pro
                405                 410                 415
Ala Gln Asp Pro Val Lys Pro Trp Gln Leu Leu Glu Asn Met Tyr Asn
            420                 425                 430
Leu Thr Phe His Val Gly Gly Leu Pro Leu Arg Phe Asp Ser Ser Gly
        435                 440                 445
```

Asn Val Asp Met Glu Tyr Asp Leu Lys Leu Trp Val Trp Gln Gly Ser
    450                 455                 460

Val Pro Arg Leu His Asp Val Gly Arg Phe Asn Gly Ser Leu Arg Thr
465                 470                 475                 480

Glu Arg Leu Lys Ile Arg Trp His Thr Ser Asp Asn Gln Lys Pro Val
                485                 490                 495

Ser Arg Cys Ser Arg Gln Cys Gln Glu Gly Gln Val Arg Arg Val Lys
            500                 505                 510

Gly Phe His Ser Cys Cys Tyr Asp Cys Val Asp Cys Glu Ala Gly Ser
            515                 520                 525

Tyr Arg Gln Asn Pro Asp Asp Ile Ala Cys Thr Phe Cys Gly Gln Asp
        530                 535                 540

Glu Trp Ser Pro Glu Arg Ser Thr Arg Cys Phe Arg Arg Ser Arg
545                 550                 555                 560

Phe Leu Ala Trp Gly Glu Pro Ala Val Leu Leu Leu Leu Leu Leu Leu
                565                 570                 575

Ser Leu Ala Leu Gly Leu Val Leu Ala Ala Leu Gly Leu Phe Val His
            580                 585                 590

His Arg Asp Ser Pro Leu Val Gln Ala Ser Gly Gly Pro Leu Ala Cys
        595                 600                 605

Phe Gly Leu Val Cys Leu Gly Leu Val Cys Leu Ser Val Leu Leu Phe
610                 615                 620

Pro Gly Gln Pro Ser Pro Ala Arg Cys Leu Ala Gln Gln Pro Leu Ser
625                 630                 635                 640

His Leu Pro Leu Thr Gly Cys Leu Ser Thr Leu Phe Leu Gln Ala Ala
                645                 650                 655

Glu Ile Phe Val Glu Ser Glu Leu Pro Leu Ser Trp Ala Asp Arg Leu
            660                 665                 670

Ser Gly Cys Leu Arg Gly Pro Trp Ala Trp Leu Val Val Leu Leu Ala
        675                 680                 685

Met Leu Val Glu Val Ala Leu Cys Thr Trp Tyr Leu Val Ala Phe Pro
690                 695                 700

Pro Glu Val Val Thr Asp Trp His Met Leu Pro Thr Glu Ala Leu Val
705                 710                 715                 720

His Cys Arg Thr Arg Ser Trp Val Ser Phe Gly Leu Ala His Ala Thr
                725                 730                 735

Asn Ala Thr Leu Ala Phe Leu Cys Phe Leu Gly Thr Phe Leu Val Arg
            740                 745                 750

Ser Gln Pro Gly Arg Tyr Asn Arg Ala Arg Gly Leu Thr Phe Ala Met
        755                 760                 765

Leu Ala Tyr Phe Ile Thr Trp Val Ser Phe Val Pro Leu Leu Ala Asn
        770                 775                 780

Val Gln Val Val Leu Arg Pro Ala Val Gln Met Gly Ala Leu Leu Leu
785                 790                 795                 800

Cys Val Leu Gly Ile Leu Ala Ala Phe His Leu Pro Arg Cys Tyr Leu
                805                 810                 815

Leu Met Arg Gln Pro Gly Leu Asn Thr Pro Glu Phe Phe Leu Gly Gly
            820                 825                 830

Gly Pro Gly Asp Ala Gln Gly Gln Asn Asp Gly Asn Thr Gly Asn Gln
        835                 840                 845

Gly Lys His Glu
    850

<210> SEQ ID NO 16
<211> LENGTH: 2577
<212> TYPE: DNA
<213> ORGANISM: Rattus sp.

<400> SEQUENCE: 16

| | | | | | |
|---|---|---|---|---|---|
| atgccggptt | tggctatctt | gggcctcagt | ctggctgctt | cctggagct | tgggatgggg | 60 |
| tcctctttgt | gtctgtcaca | gcaattcaag | gcacaagggg | actatatatt | gggtggacta | 120 |
| tttcccctgg | gcacaactga | ggaggccact | ctcaaccaga | gaacacagcc | caacggcatc | 180 |
| ctatgtacca | ggttctcgcc | ccttggtttg | ttcctggcca | tggctatgaa | gatggctgta | 240 |
| gaggagatca | acaatggatc | tgccttgctc | cctgggctgc | gactgggcta | tgacctgttt | 300 |
| gacacatgct | cagagccagt | ggtcaccatg | aagcccagcc | tcatgttcat | ggccaaggtg | 360 |
| ggaagtcaaa | gcattgctgc | ctactgcaac | tacacacagt | accaaccccg | tgtgctggct | 420 |
| gtcattggtc | cccactcatc | agagcttgcc | ctcattacag | gcaagttctt | cagcttcttc | 480 |
| ctcatgccac | aggtcagcta | tagtgccagc | atggatcggc | taagtgaccg | ggaaacattt | 540 |
| ccatccttct | ccgcacagt | gcccagtgac | cgggtgcagc | tgcaggccgt | tgtgacactg | 600 |
| ttgcagaatt | tcagctggaa | ctgggtggct | gccttaggta | gtgatgatga | ctatggccgg | 660 |
| gaaggtctga | gcatcttttc | tggtctggcc | aactcacgag | gtatctgcat | tgcacacgag | 720 |
| ggcctggtgc | acaacatga | cactagtggc | caacaattgg | gcaaggtggt | ggatgtgcta | 780 |
| cgccaagtga | accaaagcaa | agtacaggtg | gtggtgctgt | ttgcatctgc | ccgtgctgtc | 840 |
| tactcccttt | ttagctacag | catccttcat | gacctctcac | ccaaggtatg | ggtggccagt | 900 |
| gagtcctggc | tgacctctga | cctggtcatg | acacttccca | atattgcccg | tgtgggcact | 960 |
| gttcttgggt | tctgcagcg | cggtgcccta | ctgcctgaat | tttcccatta | tgtggagact | 1020 |
| cgccttgccc | tagctgctga | cccaacattc | tgtgcctccc | tgaaagctga | gttggatctg | 1080 |
| gaggagcgcg | tgatggggcc | acgctgttca | caatgtgact | acatcatgct | acagaacctg | 1140 |
| tcatctgggc | tgatgcagaa | cctatcagct | gggcagttgc | accaccaaat | atttgcaacc | 1200 |
| tatgcagctg | tgtacagtgt | ggctcaggcc | cttcacaaca | ccctgcagtg | caatgtctca | 1260 |
| cattgccaca | catcagagcc | tgttcaaccc | tggcagctcc | tggagaacat | gtacaatatg | 1320 |
| agtttccgtg | ctcgagactt | gacactgcag | tttgatgcca | agggagtgt | agacatggaa | 1380 |
| tatgacctga | agatgtgggt | gtggcagagc | cctacacctg | tactacatac | tgtaggcacc | 1440 |
| ttcaacggca | cccttcagct | gcagcactcg | aaaatgtatt | ggccaggcaa | ccaggtgcca | 1500 |
| gtctcccagt | gctcccggca | gtgcaaagat | ggccaggtgc | gcagagtaaa | gggctttcat | 1560 |
| tcctgctgct | atgactgtgt | ggactgcaag | gcagggagct | accggaagca | tccagatgac | 1620 |
| ttcacctgta | ctccatgtgg | caaggatcag | tggtccccag | aaaaaagcac | aacctgctta | 1680 |
| cctcgcaggc | ccaagtttct | ggcttggggg | gagccagctg | tgctgtcact | tctcctgctg | 1740 |
| cttttgcctgg | tgctgggcct | gacactggct | gccctggggc | tctttgtcca | ctactgggac | 1800 |
| agccctcttg | ttcaggcctc | aggtgggtca | ctgttctgct | ttggcctgat | ctgcctaggc | 1860 |
| ctcttctgcc | tcagtgtcct | tctgttccca | ggacgaccac | gctctgccag | ctgccttgcc | 1920 |
| caacaaccaa | tggctcacct | ccctctcaca | ggctgcctga | gcacactctt | cctgcaagca | 1980 |
| gccgagatct | ttgtggagtc | tgagctgcca | ctgagttggg | caaactggct | ctgcagctac | 2040 |
| cttcggggcc | cctggccttg | gctggtggta | ctgctggcca | ctcttgtgga | ggctgcacta | 2100 |
| tgtgcctggt | acttgatggc | tttcccctcca | gaggtggtga | cagattggca | ggtgctgccc | 2160 |
| acggaggtac | tggaacactg | ccgcatgcgt | tcctgggtca | gcctgggctt | ggtgcacatc | 2220 |

-continued

```
accaatgcag tgttagcttt cctctgcttt ctgggcactt tcctggtaca gagccagcct    2280
ggtcgctata accgtgcccg tggcctcacc ttcgccatgc tagcttattt catcatctgg    2340
gtctcttttg tgcccctcct ggctaatgtg caggtggcct accagccagc tgtgcagatg    2400
ggtgctatct tattctgtgc cctgggcatc ctggccacct tccacctgcc caaatgctat    2460
gtacttctgt ggctgccaga gctcaacacc caggagttct tcctgggaag gagccccaag    2520
gaagcatcag atgggaatag tggtagtagt gaggcaactc ggggacacag tgaatga       2577

<210> SEQ ID NO 17
<211> LENGTH: 858
<212> TYPE: PRT
<213> ORGANISM: Rattus sp.

<400> SEQUENCE: 17
```

| Met | Pro | Gly | Leu | Ala | Ile | Leu | Gly | Leu | Ser | Leu | Ala | Ala | Phe | Leu | Glu |
|---|---|---|---|---|---|---|---|---|---|---|---|---|---|---|---|
| 1 | | | | 5 | | | | | 10 | | | | | 15 | |

| Leu | Gly | Met | Gly | Ser | Ser | Leu | Cys | Leu | Ser | Gln | Gln | Phe | Lys | Ala | Gln |
|---|---|---|---|---|---|---|---|---|---|---|---|---|---|---|---|
| | | | 20 | | | | | 25 | | | | | 30 | | |

| Gly | Asp | Tyr | Ile | Leu | Gly | Gly | Leu | Phe | Pro | Leu | Gly | Thr | Thr | Glu | Glu |
|---|---|---|---|---|---|---|---|---|---|---|---|---|---|---|---|
| | | | 35 | | | | | 40 | | | | | 45 | | |

| Ala | Thr | Leu | Asn | Gln | Arg | Thr | Gln | Pro | Asn | Gly | Ile | Leu | Cys | Thr | Arg |
|---|---|---|---|---|---|---|---|---|---|---|---|---|---|---|---|
| | 50 | | | | | 55 | | | | | 60 | | | | |

| Phe | Ser | Pro | Leu | Gly | Leu | Phe | Leu | Ala | Met | Ala | Met | Lys | Met | Ala | Val |
|---|---|---|---|---|---|---|---|---|---|---|---|---|---|---|---|
| 65 | | | | | 70 | | | | | 75 | | | | | 80 |

| Glu | Glu | Ile | Asn | Asn | Gly | Ser | Ala | Leu | Leu | Pro | Gly | Leu | Arg | Leu | Gly |
|---|---|---|---|---|---|---|---|---|---|---|---|---|---|---|---|
| | | | | 85 | | | | | 90 | | | | | 95 | |

| Tyr | Asp | Leu | Phe | Asp | Thr | Cys | Ser | Glu | Pro | Val | Val | Thr | Met | Lys | Pro |
|---|---|---|---|---|---|---|---|---|---|---|---|---|---|---|---|
| | | | 100 | | | | | 105 | | | | | 110 | | |

| Ser | Leu | Met | Phe | Met | Ala | Lys | Val | Gly | Ser | Gln | Ser | Ile | Ala | Ala | Tyr |
|---|---|---|---|---|---|---|---|---|---|---|---|---|---|---|---|
| | | | 115 | | | | | 120 | | | | | 125 | | |

| Cys | Asn | Tyr | Thr | Gln | Tyr | Gln | Pro | Arg | Val | Leu | Ala | Val | Ile | Gly | Pro |
|---|---|---|---|---|---|---|---|---|---|---|---|---|---|---|---|
| | 130 | | | | | 135 | | | | | 140 | | | | |

| His | Ser | Ser | Glu | Leu | Ala | Leu | Ile | Thr | Gly | Lys | Phe | Phe | Ser | Phe | Phe |
|---|---|---|---|---|---|---|---|---|---|---|---|---|---|---|---|
| 145 | | | | | 150 | | | | | 155 | | | | | 160 |

| Leu | Met | Pro | Gln | Val | Ser | Tyr | Ser | Ala | Ser | Met | Asp | Arg | Leu | Ser | Asp |
|---|---|---|---|---|---|---|---|---|---|---|---|---|---|---|---|
| | | | | 165 | | | | | 170 | | | | | 175 | |

| Arg | Glu | Thr | Phe | Pro | Ser | Phe | Phe | Arg | Thr | Val | Pro | Ser | Asp | Arg | Val |
|---|---|---|---|---|---|---|---|---|---|---|---|---|---|---|---|
| | | | 180 | | | | | 185 | | | | | 190 | | |

| Gln | Leu | Gln | Ala | Val | Val | Thr | Leu | Leu | Gln | Asn | Phe | Ser | Trp | Asn | Trp |
|---|---|---|---|---|---|---|---|---|---|---|---|---|---|---|---|
| | | | 195 | | | | | 200 | | | | | 205 | | |

| Val | Ala | Ala | Leu | Gly | Ser | Asp | Asp | Asp | Tyr | Gly | Arg | Glu | Gly | Leu | Ser |
|---|---|---|---|---|---|---|---|---|---|---|---|---|---|---|---|
| | 210 | | | | | 215 | | | | | 220 | | | | |

| Ile | Phe | Ser | Gly | Leu | Ala | Asn | Ser | Arg | Gly | Ile | Cys | Ile | Ala | His | Glu |
|---|---|---|---|---|---|---|---|---|---|---|---|---|---|---|---|
| 225 | | | | | 230 | | | | | 235 | | | | | 240 |

| Gly | Leu | Val | Pro | Gln | His | Asp | Thr | Ser | Gly | Gln | Gln | Leu | Gly | Lys | Val |
|---|---|---|---|---|---|---|---|---|---|---|---|---|---|---|---|
| | | | | 245 | | | | | 250 | | | | | 255 | |

| Val | Asp | Val | Leu | Arg | Gln | Val | Asn | Gln | Ser | Lys | Val | Gln | Val | Val | Val |
|---|---|---|---|---|---|---|---|---|---|---|---|---|---|---|---|
| | | | 260 | | | | | 265 | | | | | 270 | | |

| Leu | Phe | Ala | Ser | Ala | Arg | Ala | Val | Tyr | Ser | Leu | Phe | Ser | Tyr | Ser | Ile |
|---|---|---|---|---|---|---|---|---|---|---|---|---|---|---|---|
| | | 275 | | | | | 280 | | | | | 285 | | | |

| Leu | His | Asp | Leu | Ser | Pro | Lys | Val | Trp | Val | Ala | Ser | Glu | Ser | Trp | Leu |
|---|---|---|---|---|---|---|---|---|---|---|---|---|---|---|---|
| | 290 | | | | | 295 | | | | | 300 | | | | |

| Thr | Ser | Asp | Leu | Val | Met | Thr | Leu | Pro | Asn | Ile | Ala | Arg | Val | Gly | Thr |
|---|---|---|---|---|---|---|---|---|---|---|---|---|---|---|---|
| 305 | | | | | 310 | | | | | 315 | | | | | 320 |

```
Val Leu Gly Phe Leu Gln Arg Gly Ala Leu Pro Glu Phe Ser His
            325                 330                 335

Tyr Val Glu Thr Arg Leu Ala Leu Ala Ala Asp Pro Thr Phe Cys Ala
            340                 345                 350

Ser Leu Lys Ala Glu Leu Asp Leu Glu Glu Arg Val Met Gly Pro Arg
            355                 360                 365

Cys Ser Gln Cys Asp Tyr Ile Met Leu Gln Asn Leu Ser Ser Gly Leu
            370                 375                 380

Met Gln Asn Leu Ser Ala Gly Gln Leu His His Gln Ile Phe Ala Thr
385                 390                 395                 400

Tyr Ala Ala Val Tyr Ser Val Ala Gln Ala Leu His Asn Thr Leu Gln
                405                 410                 415

Cys Asn Val Ser His Cys His Thr Ser Glu Pro Val Gln Pro Trp Gln
                420                 425                 430

Leu Leu Glu Asn Met Tyr Asn Met Ser Phe Arg Ala Arg Asp Leu Thr
            435                 440                 445

Leu Gln Phe Asp Ala Lys Gly Ser Val Asp Met Glu Tyr Asp Leu Lys
            450                 455                 460

Met Trp Val Trp Gln Ser Pro Thr Pro Val Leu His Thr Val Gly Thr
465                 470                 475                 480

Phe Asn Gly Thr Leu Gln Leu Gln His Ser Lys Met Tyr Trp Pro Gly
                485                 490                 495

Asn Gln Val Pro Val Ser Gln Cys Ser Arg Gln Cys Lys Asp Gly Gln
                500                 505                 510

Val Arg Arg Val Lys Gly Phe His Ser Cys Cys Tyr Asp Cys Val Asp
            515                 520                 525

Cys Lys Ala Gly Ser Tyr Arg Lys His Pro Asp Asp Phe Thr Cys Thr
            530                 535                 540

Pro Cys Gly Lys Asp Gln Trp Ser Pro Glu Lys Ser Thr Thr Cys Leu
545                 550                 555                 560

Pro Arg Arg Pro Lys Phe Leu Ala Trp Gly Glu Pro Ala Val Leu Ser
                565                 570                 575

Leu Leu Leu Leu Leu Cys Leu Val Leu Gly Leu Thr Leu Ala Ala Leu
                580                 585                 590

Gly Leu Phe Val His Tyr Trp Asp Ser Pro Leu Val Gln Ala Ser Gly
            595                 600                 605

Gly Ser Leu Phe Cys Phe Gly Leu Ile Cys Leu Gly Leu Phe Cys Leu
            610                 615                 620

Ser Val Leu Leu Phe Pro Gly Arg Pro Arg Ser Ala Ser Cys Leu Ala
625                 630                 635                 640

Gln Gln Pro Met Ala His Leu Pro Leu Thr Gly Cys Leu Ser Thr Leu
                645                 650                 655

Phe Leu Gln Ala Ala Glu Ile Phe Val Glu Ser Glu Leu Pro Leu Ser
            660                 665                 670

Trp Ala Asn Trp Leu Cys Ser Tyr Leu Arg Gly Pro Trp Ala Trp Leu
            675                 680                 685

Val Val Leu Leu Ala Thr Leu Val Glu Ala Ala Leu Cys Ala Trp Tyr
            690                 695                 700

Leu Met Ala Phe Pro Pro Glu Val Val Thr Asp Trp Gln Val Leu Pro
705                 710                 715                 720

Thr Glu Val Leu Glu His Cys Arg Met Arg Ser Trp Val Ser Leu Gly
                725                 730                 735

Leu Val His Ile Thr Asn Ala Val Leu Ala Phe Leu Cys Phe Leu Gly
```

-continued

```
                740                 745                 750
Thr Phe Leu Val Gln Ser Gln Pro Gly Arg Tyr Asn Arg Ala Arg Gly
        755                 760                 765

Leu Thr Phe Ala Met Leu Ala Tyr Phe Ile Ile Trp Val Ser Phe Val
    770                 775                 780

Pro Leu Leu Ala Asn Val Gln Val Ala Tyr Gln Pro Ala Val Gln Met
785                 790                 795                 800

Gly Ala Ile Leu Phe Cys Ala Leu Gly Ile Leu Ala Thr Phe His Leu
                805                 810                 815

Pro Lys Cys Tyr Val Leu Leu Trp Leu Pro Glu Leu Asn Thr Gln Glu
            820                 825                 830

Phe Phe Leu Gly Arg Ser Pro Lys Glu Ala Ser Asp Gly Asn Ser Gly
        835                 840                 845

Ser Ser Glu Ala Thr Arg Gly His Ser Glu
850                 855
```

US 8,247,184 B2

ASSAYS USING CHIMERIC T1R POLYPEPTIDES FOR IDENTIFYING PUTATIVE TASTE MODULATORY COMPOUNDS

RELATED APPLICATION

This application is a continuation of U.S. application Ser. No. 11/583,097 filed Oct. 19, 2006 now U.S. Pat. No. 7,906,627, which claims the benefit of priority to U.S. Provisional Application No. 60/728,324, filed Oct. 20, 2005, and is a CIP of U.S. application Ser. No. 10/569,870 filed Feb. 28, 2006 now abandoned, which is a 371 of PCT/US04/25459 filed Aug. 6, 2004, which claims benefit of U.S. Provisional Application No. 60/494,071 filed Aug. 6, 2003 and U.S. Provisional Application No. 60/552,064 filed Mar. 9, 2004. The applications are incorporated by reference in their entirety herein.

FIELD OF THE INVENTION

This invention relates to novel chimeric human and rodent taste receptor polypeptides, nucleic acid sequences encoding, cells that express these chimeric taste receptor polypeptides and their use in identifying taste modulators, particularly modulators of sweet and umami taste.

BACKGROUND OF THE INVENTION

The human T1R family taste receptors include hT1R1, 2, and 3. The T1Rs belong to class-C G protein coupled receptors, and each Class-C GPCR consists of a large N-terminal extracellular domain and a C-terminal 7-transmembrane domain. It is generally known that hT1R1 and hT1R3 form a heteromeric receptor that modulates umami taste transduction and which recognizes umami tastants, while hT1R2 and hT1R3 form a heteromeric receptor that modulates sweet taste transduction and which recognizes sweet tastants. Therefore it is known that the umami taste receptor (hT1R1/hT1R3) and the sweet taste receptor (hT1R2/hT1R3) share a common subunit hT1R3.

BRIEF DESCRIPTION AND OBJECTS OF THE INVENTION

It is an object of the invention to produce chimeric taste receptor polypeptides that respond to umami and/or sweet taste stimuli and/or which enhance umami or sweet taste elicited by other compounds.

It is another object of the invention to use such chimeric taste receptor polypeptides in assays for identifying compounds that themselves modulate sweet or umami taste and/or which enhance sweet or umami taste elicited by other compounds.

More specifically it is an object of the invention to create a DNA fusion encoding a chimeric taste receptor by combining portions of the T1R1 and T1R2 taste receptor genes and to co-express same with a T1R3 taste receptor of the same or different species to create a chimeric taste receptor that responds to sweet and/or umami taste stimuli or which enhances umami or sweet taste elicited by other compounds.

Even more specifically it is an object of the invention to produce a chimeric taste receptor by combining all or a portion of the extracellular domains of a T1R1 polypeptide or a DNA encoding, preferably hT1R1 or mT1R1 or rT1R1 and all or a portion of the transmembrane domain of a T1R2 polypeptide or a DNA encoding, preferably hT1R2, rT1R2 or mT1R2 or a portion thereof to create a umami-sweet chimeric taste receptor polypeptide or a DNA encoding.

Also more specifically it is an object of the invention to produce a chimeric taste receptor by combining all or a portion of the extracellular domains of a T1R2 polypeptide or a DNA encoding, preferably hT1R2, rT1R2 or mT1R2, and all or a portion of the transmembrane domains of a T1R1 polypeptide or a DNA encoding, preferably hT1R1, mT1R1 or rT1R1 to create a chimeric sweet-umami taste receptor polypeptide or a DNA encoding.

It is another object of the invention to provide the specific hT1R1-2 and hT1R2-1 nucleic acid sequences and polypeptide sequences contained in SEQ ID NO:1-4.

It is another object of the invention to express these nucleic acid sequences encoding chimeric taste receptors in suitable host cells, preferably HEK-293 cells, that additionally preferably express a G protein and a T1R3 nucleic acid sequence.

It is another object of the invention to use these cells in assays for identifying molecules that modulate sweet or umami taste, e.g., umami and sweet tasting ligands and umami and sweet enhancers.

BRIEF DESCRIPTION OF THE FIGURES

FIG. 1 contains the nucleic acid sequence of a chimeric sweet-umami taste receptor according to the invention designated hT1R2-1 comprising the extracellular domain of human T1R2 fused to the transmembrane of human T1R1 (SEQ ID NO:1)

FIG. 2 contains the polypeptide sequence of a chimeric sweet-umami taste receptor polypeptide according to the invention designated hT1R2-1 comprising the extracellular portion of human T1R2 and the transmembrane portion of human T1R1 (SEQ ID NO:2).

FIG. 3 contains the nucleic acid sequence of a chimeric taste receptor according to the invention designated hT1R1-2 containing the extracellular domains of hT1R1 and the transmembrane domains of hT1R2. (SEQ ID NO:3)

FIG. 4 contains the polypeptide sequence of a chimeric receptor according to the invention designated hT1R1-2 (SEQ ID NO:4) and contains the contains the protein sequence of a chimeric G protein G16gust44 used in the present invention containing the N-terminal portion of Galpha16 fused to the 44 carboxy terminal amino acids of gustducin (SEQ ID NO:5).

FIG. 6 contains the nucleic acid sequences and protein sequences for human and murine and rat T1R1, T1R2 and T1R3 (SEQ ID NO:6-17)

FIG. 8 contains experimental results comparing effective concentrations (EC50s) of different sweeteners activating the native hT1R2/hT1R3 receptor in comparison to chimeric hT1R2-1 (SEQ ID NO:2).

DETAILED DESCRIPTION OF THE INVENTION

Figure 5:
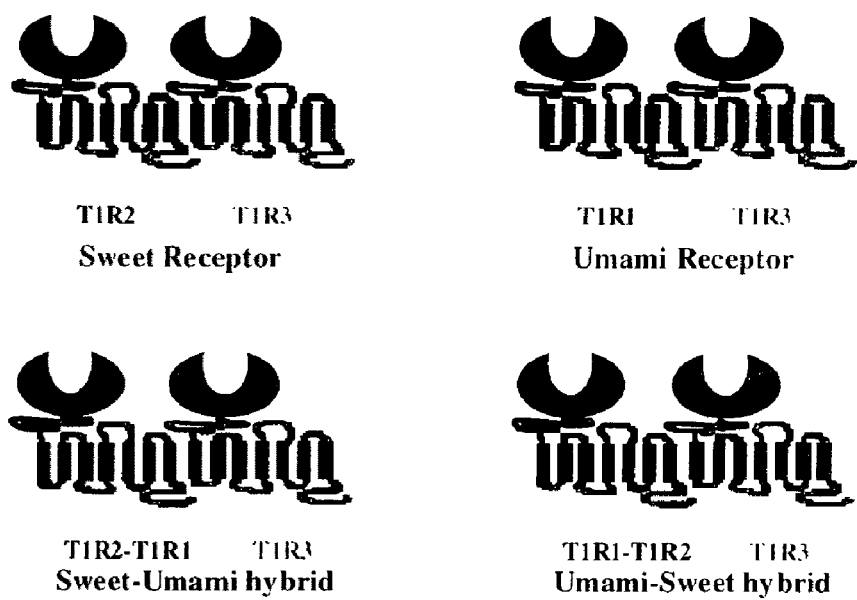
FIG. 5 contains schematics for native T1R2/T13, T1R1/T1R3, and chimeric sweet-umami hT1R2-1/T1R3 and chimeric umami-sweet hT1R1-2/T1R3.

Prior to specifically describing the invention, the following definitions are provided.

The term "T1R" family includes polymorphic variants, alleles, mutants, and homologs that: (1) have about 30-40% amino acid sequence identity, more specifically about 40, 50, 60, 70, 75, 80, 85, 90, 95, 96, 97, 98, or 99% amino acid sequence identity to the T1Rs disclosed infra, and in the Zuker (Id) (2001) and Adler (Id.) (2001) applications incorporated, by reference herein over a window of about 25 amino acids, optimally 50-100 amino acids; (2) specifically bind to antibodies raised against an immunogen comprising an amino acid sequence selected from the group consisting of the T1R sequences disclosed infra, and conservatively modified variants thereof; (3) specifically hybridize (with a size of at least about 100, optionally at least about 500-1000 nucleotides) under stringent hybridization conditions to a sequence selected from the group consisting of the T21 DNA sequences disclosed infra, and conservatively modified variants thereof; (4) comprise a sequence at least about 40% identical to an amino acid sequence selected from the group consisting of the T1R amino acid sequences disclosed infra or (5) are amplified by primers that specifically hybridize under stringent hybridization conditions to the described T1R sequences.

In particular, these "T1R's" include taste receptor GPCRs referred to as hT1R1, hT1R2, hT1R3, rT1R1, rT1R2, rT1R3, mT1R1, mT1R2, and mT1R3 having the nucleic acid sequences and amino acid sequences provided in this application, and variants, alleles, mutants, orthologs and chimeras thereof which specifically bind and/or respond to sweet or umami ligands including activators, inhibitors and enhancers. Preferably, the T1Rs herein are chimeric sequences derived from portions of a T1R1 polypeptide and a T1R2 polypeptide or their corresponding DNA coding sequences. As exemplified herein, preferred chimeric T1Rs according to the invention comprise the extracellular region of one T1R, i.e., T1R1 or T1R2 and the transmembrane region of another T1R, either T1R1 or T1R2.

Topologically, certain chemosensory GPCRs have an "N-terminal domain;" "extracellular domains," a "transmembrane domain" comprising seven transmembrane regions, and corresponding cytoplasmic and extracellular loops, "cytoplasmic regions," and a "C-terminal region" (see, e.g., Hoon et al, Cell, 96:541-51 (1999); Buck & Axel, Cell, 65:175-87 (1991)). These regions can be structurally identified using methods known to those of skill in the art, such as sequence analysis programs that identify hydrophobic and hydrophilic domains (see, e.g., Stryer, Biochemistry, (3rd ed. 1988); see also any of a number of Internet based sequence analysis programs, such as those found at dot.imgen.bcm.tmc.edu). These regions are useful for making chimeric proteins and for in vitro assays of the invention, e.g., ligand binding assays.

"Extracellular domains" therefore refers to the domains of T1R polypeptides that protrude from the cellular membrane and are exposed to the extracellular face of the cell. Such regions would include the "N-terminal domain" that is exposed to the extracellular face of the cell, as well as the extracellular loops of the transmembrane domain that are exposed to the extracellular face of the cell, i.e., the extracellular loops between transmembrane regions 2 and 3, transmembrane regions 4 and 5, and transmembrane regions 6 and 7. The "N-terminal domain" starts at the N-terminus and extends to a region close to the start of the transmembrane region. These extracellular regions are useful for in vitro ligand binding assays, both soluble and solid phase. In addition, transmembrane regions, described below, can also be involved in ligand binding, either in combination with the extracellular region or alone, and are therefore also useful for in vitro ligand binding assays. The extracellular regions or domains of human, rat and murine T1R1, T1R2 and T1R3 are contained in FIG. 6.

"Transmembrane domain," which comprises the seven transmembrane "regions," refers to the domain of T1R polypeptides that lies within the plasma membrane, and may also include the corresponding cytoplasmic (intracellular) and extracellular loops, also referred to as transmembrane "regions." The seven transmembrane regions and extracellular and cytoplasmic loops can be identified using standard methods, as described in Kyte & Doolittle, J. Mol. Biol., 157:105-32 (1982)), or in Stryer, supra. The transmembrane domains or regions of human, rat, and murine T1R1, T1R2 and T1R3 are also contained in FIG. 6.

"Cytoplasmic domains" refers to the domains of T1R proteins that face the inside of the cell, e.g., the "C-terminal domain" and the intracellular loops of the transmembrane domain, e.g., the intracellular loops between transmembrane regions 1 and 2, transmembrane regions 3 and 4, and transmembrane regions 5 and 6. "C-terminal domain" refers to the region that spans from the end of the last transmembrane region to the C-terminus of the protein, and which is normally located within the cytoplasm.

The term "7-transmembrane receptor" means a polypeptide belonging to a superfamily of transmembrane proteins that have seven regions that span the plasma membrane seven times (thus, the seven regions are called "transmembrane" or "TM" domains TM I to TM VII).

The term "ligand-binding region" refers to sequences derived from a chemosensory or taste receptor that substantially incorporates transmembrane domains II to VII (TM II to VII). The region may be capable of binding a ligand, and more particularly, a taste eliciting compound.

The term "plasma membrane translocation domain" or simply "translocation domain" means a polypeptide domain that when incorporated into the amino terminus of a polypeptide coding sequence, can with great efficiency "chaperone" or "translocate" the hybrid ("fusion") protein to the cell plasma membrane. An exemplary "translocation domain" is derived from the amino terminus of the human rhodopsin receptor polypeptide, a 7-transmembrane receptor. Another translocation domain is known is the bovine rhodopsin sequence and is also useful for facilitating translocation. Rhodopsin derived sequences are particularly efficient in translocating 7-transmembrane fusion proteins to the plasma membrane.

The phrase "functional effects" in the context of assays for testing compounds that modulate T1R family member mediated taste transduction includes the determination of any parameter that is indirectly or directly under the influence of the receptor, e.g., functional, physical and chemical effects. It includes ligand binding, changes in ion flux, membrane potential, current flow, transcription, G protein binding, GPCR phosphorylation or dephosphorylation, signal transduction, receptor-ligand interactions, second messenger concentrations (e.g., cAMP, cGMP, IP3, or intracellular $Ca^{2+}$), in vitro, in vivo, and ex vivo and also includes other physiologic effects such increases or decreases of neurotransmitter or hormone release.

By "determining the functional effect" is meant assays for a compound that increases or decreases a parameter that is indirectly or directly under the influence of a T1R family member, e.g., functional, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties, patch clamping, voltage-sensitive dyes, whole cell currents, radioisotope efflux, inducible markers, oocyte T1R gene expression; tissue culture cell T1R expression; transcriptional activation of T1R genes; ligand binding assays; voltage, membrane potential and conductance changes; ion flux assays; changes in intracellular second messengers such as cAMP, cGMP, and inositol triphosphate (IP3); changes in intracellular calcium levels; neurotransmitter release, and the like.

"Inhibitors," "activators," and "modulators" of T1R proteins receptors are used interchangeably to refer to inhibitory, activating, or modulating molecules identified using in vitro and in vivo assays for taste transduction, e.g., ligands, agonists, antagonists, and their homologs and mimetics. Inhibitors are compounds that, e.g., bind to, partially or totally block stimulation, decrease, prevent, delay activation, inactivate, desensitize, or down regulate taste transduction, e.g., antagonists. Activators are compounds that, e.g., bind to, stimulate, increase, open, activate, facilitate, enhance activation, sensitize, or up regulate taste transduction, e.g., agonists. Modulators include compounds that, e.g., alter the interaction of a receptor with extracellular proteins that bind activators or inhibitor; G Proteins; kinases (e.g., homologs of rhodopsin kinase and beta adrenergic receptor kinases that are involved in deactivation and desensitization of a receptor); and arrestins, which also deactivate and desensitize receptors. Modulators include genetically modified versions of T1R family members, e.g., with altered activity, as well as naturally occurring and synthetic ligands, antagonists, agonists, small chemical molecules and the like. In the present invention this includes in particular sweet ligands (agonists or antagonists), umami ligands (agonists and antagonists), sweet enhancers and umami enhancers and sweet taste or umami taste inhibitors.

Such assays for inhibitors and activators include, e.g., expressing T1R family members in cells or cell membranes, applying putative modulator compounds in the presence or absence of compounds that modulate, e.g., sweet and umami compounds, and then determining the functional effects on taste transduction, as described above. Samples or assays comprising T1R family members that are treated with a potential activator, inhibitor, or modulator are compared to control samples without the inhibitor, activator, or modulator to examine the extent of modulation. Control samples (untreated with modulators) are assigned a relative T1R activity value of 100%. Inhibition of a T1R is achieved when the T1R activity value relative to the control is about 80%, optionally 50% or 25-0%. Activation of a T1R is achieved when the T1R activity value relative to the control is 110%, optionally 150%, optionally 200-500%, or 1000-3000% higher. In the present invention these assays will use chimeric T1Rs that comprise all or a portion of the extracellular portion of T1R1 or T1R2 and all or a portion of the transmembrane domains of another T1R, i.e., T1R2 or T1R1.

The terms "purified," "substantially purified," and "isolated" as used herein refer to the state of being free of other, dissimilar compounds with which the compound of the invention is normally associated in its natural state. Preferably, "purified," "substantially purified," and "isolated" means that the composition comprises at least 0.5%, 1%, 5%, 10%, or 20%, and most preferably at least 50% or 75% of the mass, by weight, of a given sample. In one preferred embodiment, these terms refer to the compound of the invention comprising at least 95% of the mass, by weight, of a given sample. As used herein, the terms "purified," "substantially purified," and "isolated", when referring to a nucleic acid or protein, of nucleic acids or proteins, also refers to a state of purification or concentration different than that which occurs naturally in the mammalian, especially human, body. Any degree of purification or concentration greater than that which occurs naturally in the mammalian, especially human, body, including (1) the purification from other associated structures or compounds or (2) the association with structures or compounds to which it is not normally associated in the mammalian, especially human, body, are within the meaning of "isolated." The nucleic acid or protein or classes of nucleic acids or proteins, described herein, may be isolated, or otherwise associated with structures or compounds to which they are not normally associated in nature, according to a variety of methods and processes known to those of skill in the art.

As used herein, the term "isolated," when referring to a nucleic acid or polypeptide refers to a state of purification or concentration different than that which occurs naturally in the mammalian, especially human, body. Any degree of purification or concentration greater than that which occurs naturally in the body, including (1) the purification from other naturally-occurring associated structures or compounds, or (2) the association with structures or compounds to which it is not normally associated in the body are within the meaning of "isolated" as used herein. The nucleic acids or polypeptides described herein may be isolated or otherwise associated with structures or compounds to which they are not normally associated in nature, according to a variety of methods and processed known to those of skill in the art.

As used herein, the terms "amplifying" and "amplification" refer to the use of any suitable amplification methodology for generating or detecting recombinant or naturally expressed nucleic acid, as described in detail, below. For example, the invention provides methods and reagents (e.g., specific oligonucleotide primer pairs) for amplifying (e.g., by polymerase chain reaction, PCR) naturally expressed (e.g., genomic or mRNA) or recombinant (e.g., cDNA) nucleic acids of the invention (e.g., taste eliciting compound-binding sequences of the invention) in vivo or in vitro.

The term "expression vector" refers to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression "cassettes which contain only the minimum elements needed for transcription of the recombinant nucleic acid.

The term "library" means a preparation that is a mixture of different nucleic acid or poly-peptide molecules, such as the library of recombinant generated sensory, particularly taste receptor ligand-binding regions generated by amplification of nucleic acid with degenerate primer pairs, or an isolated collection of vectors that incorporate the amplified ligand-binding regions, or a mixture of cells each randomly transfected with at least one vector encoding an taste receptor.

The term "nucleic acid" or "nucleic acid sequence" refers to a deoxy-ribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating, e.g., sequences in which the third position of one or more selected codons is substituted with mixed-base and/or deoxyinosine residues (Batzer et al., Nucleic Acid Res., 19:5081 (1991); Ohtsuka et al., J. Biol. Chem., 260:2605-08 (1985); Rossolini et al., Mol. Cell. Probes, 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The "translocation domain," "ligand-binding region", and chimeric receptors compositions described herein also include "analogs," or "conservative variants" and "mimetics" ("peptidomimetics") with structures and activity that substantially correspond to the exemplary sequences. Thus, the terms "conservative variant" or "analog" or "mimetic" refer to a polypeptide which has a modified amino acid sequence, such that the change(s) do not substantially alter the polypeptide's (the conservative variant's) structure and/or activity, as defined herein. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or non-polar, etc.) such that the substitutions of even critical amino acids does not substantially alter structure and/or activity.

More particularly, "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein.

For instance, the codons GCA, GCC, GCG and GCU all encode the amino acid alanine. Thus, at every position where an alanine is specified by a codon, the codon can be altered to any of the corresponding codons described without altering the encoded polypeptide.

Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gln/asn; gly/asp; gly/ala or pro; his/asn or gln; ile/leu or val; leu/ile or val; lys/arg or gln or glu; met/leu or tyr or ile; phe/met or leu or tyr; ser/thr; thr/ser; trp/tyr; tyr/trp or phe; val/ile or leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (I); 5) Isoleucine (I), Leucine (L), Methionine (M), Valine (V); and 6) Phenylalanine (F), Tyrosine (Y), Tryptophan (W); (see also, e.g., Creighton, Proteins, W.H. Freeman and Company (1984); Schultz and Schimer, Principles of Protein Structure, Springer-Verlag (1979)). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations."

The terms "mimetic" and "peptidomimetic" refer to a synthetic chemical compound that has substantially the same structural and/or functional characteristics of the polypeptides, e.g., translocation domains, ligand-binding regions, or chimeric receptors of the invention. The mimetic can be either entirely composed of synthetic, non-natural analogs of amino acids, or may be a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity.

As with polypeptides of the invention which are conservative variants, routine experimentation will determine whether a mimetic is within the scope of the invention, i.e., that its structure and/or function is not substantially altered. Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$ for —C(=O)—NH—), aminomethylene (CH$_2$NH), ethylene, olefin (CH.dbd.CH), ether (CH$_2$O), thioether (CH$_2$—S), tetrazole (CN$_4$), thiazole, retroamide, thioamide, or ester (see, e.g., Spatola, Chemistry and Biochemistry of Amino Acids, Peptides and Proteins, Vol. 7, 267-357, Marcell Dekker, Peptide Backbone Modifications, NY (1983)). A polypeptide can also be characterized as a mimetic by containing all or some non-natural residues in place of naturally occurring amino acid residues; non-natural residues are well described in the scientific and patent literature.

A "label" or a "detectable moiety" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are optionally directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid sequences that direct transcription of a nucleic acid. As used herein, a promoter includes necessary nucleic acid sequences near the start site of transcription, such as, in the case of a polymerase 11 type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant means" also encompass the ligation of nucleic acids having various coding regions or domains or promoter sequences from different sources into an expression cassette or vector for expression of, e.g., inducible or constitutive expression of a fusion protein comprising a translocation domain of the invention and a nucleic acid sequence amplified using a primer of the invention.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Such hybridizations and wash steps can be carried out for, e.g., 1, 2, 5, 10, 15, 30, 60; or more minutes.

Nucleic acids that do not hybridize to each other under stringent conditions are still substantially related if the polypeptides which they encode are substantially related. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such hybridizations and wash steps can be carried out for, e.g., 1, 2, 5, 10, 15, 30, 60, or more minutes. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

An "anti-T1R" antibody is an antibody or antibody fragment that specifically binds a polypeptide encoded by a T1R gene, cDNA, or a subsequence thereof.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or, "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein.

For example, polyclonal antibodies raised to a T1R family member from specific species such as rat, mouse, or human can be selected to obtain only those polyclonal antibodies that are specifically immunoreactive with the T1R polypeptide or an immunogenic portion thereof and not with other proteins, except for orthologs or polymorphic variants and alleles of the T1R polypeptide. This selection may be achieved by subtracting out antibodies that cross-react with T1R molecules from other species or other T1R molecules. Antibodies can also be selected that recognize only T1R GPCR family members but not GPCRs from other families. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual, (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind" to a protein, as defined above.

The term "expression vector" refers to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression "cassettes" which contain only the minimum elements needed for transcription of the recombinant nucleic acid.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa, HEK-293, and the like, e.g., cultured cells, explants, and cells in vivo.

Based on the foregoing, the subject invention relates to the discovery that chimeric receptors comprising portions of a T1R1 and a T1R2 of the same or different species can be constructed which when co-expressed with an intact or modified T1R3 sequence of the same or different species respond specifically to umami and/or sweet tasting compounds and that the activation of these chimeric taste receptors is enhanced by sweet or umami enhancer compounds. Therefore, these chimeric receptors may be used in assays to screen for sweet and umami ligands (tastants), as well as to screen for compounds that enhance or inhibit the sweet or umami taste elicited by other sweet or umami tasting compounds.

As shown in FIGS. 1-4, in order to establish the efficacy of the subject chimeric receptors in cell-based assays for identifying taste modulatory compounds the present inventors constructed chimeric taste receptors comprising portions of hT1R2 and hT1R1 named hT1R2-1, consisting of the hT1R2 N-terminal extracellular domain and the hT1R1 C-terminal 7-transmembrane domain and hT1R1-2 containing the hT1R1 extracellular domains and the hT1R2 C-terminal 7-transmembrane domain. When these chimeric receptors were co-expressed with a human or rodent T1R3 sequence in a HEK-293 cell line that stably expressed this chimeric receptor as well as a promiscuous chimeric G protein G16-t25 or G16g44 respectively comprising the N-terminal portion of Galpha16 and the 25 or 44 carboxy-terminal amino acids of transducin or gustducin, that the resultant chimeric sweet-umami chimeric receptor or chimeric umami-sweet taste rector was functional and responded specifically to sweet and/or umami ligand compounds and enhancers.

Particularly it was shown that hT1R2-1 (SEQ ID NO:1 and 2) responded specifically to both sweeteners and umami compounds and that the activity of this receptor is enhanced by a sweet agonist cyclamate and is activated by umami compounds designated '807 and '336 which also function as enhancers at lower concentrations. Also, it was shown that this chimeric receptor did not respond to IMP or MSG and also that IMP had no enhancer effect on the response elicited by other umami compounds. This suggests that the extracellular region of hT1R1 is not required for all umami compounds to interact with the umami receptor but that it does impact and is necessary for MSG and IMP interactions. Also, the results which show that cyclamate a sweet agonist of the native receptor behaves like an enhancer indicate that the compound may be interacting with a different portion of the taste receptor than when it interacts with the native sweet receptor.

Particularly, it was shown that hT1R1-2 (SEQ ID NO:3 and 4) responded to the umami compounds including L-glutamate, L-aspartate and L-AP4 and that the activity of this chimeric taste receptor is enhanced by the 5' nucleotides IMP and GMP. As noted, these results suggest that the extracellular portion of hT1R1 is involved in recognizing some umami ligands and their enhancers. By contrast, none of the tested sweet compounds which included carbohydrates, sweet amino acids and synthetic sweeteners activated hT1R1-2 (SEQ ID NO:3 and 4)

More specifically, the inventors generated stable HEK-293 cell lines that constitutively express hT1R2-1 or hT1R1-2 and a T1R3 sequence, i.e. hT1R3 or rT1R3, and a chimeric G protein G16-g44 which consists of the N-terminal portion of Galpha16 fused to the last 44 amino acids of gustducin or G16-t25 which consists of the N-terminal portion of Galpha16 and the last 25 codons replaced with codons encoding the C-terminal tail (last 25 amino acid residues) of transducin. Thus in the resultant chimeric G protein the last 25 amino acids of Galpha16 are replaced with the last 25 amino acid residues of the transducin protein sequence or the last 44 amino acids are derived from gustducin.

Figure 13:
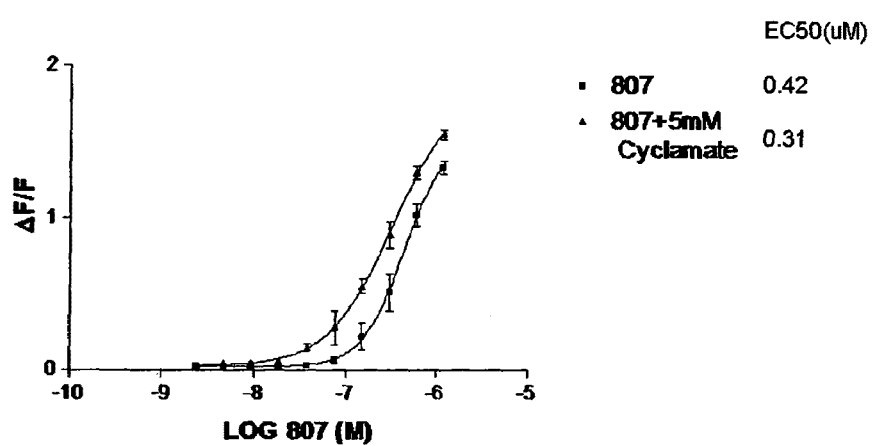
FIG. 13 contains an experiment showing that cyclamate enhances the response elicited by a proprietary umami agonist compound (designated '807) in a stable HEK-293 cell line that expresses the subject chimeric receptor hT1R2-1 and an unmodified hT1R3 sequence and that the umami compound '807 activates the chimeric hT1R2-1 taste receptor.

Using the stable HEK-293 cell line which expressed hT1R2-1 the inventors tested the effect of sweeteners including sucrose, fructose, D-tryptophan, aspartame, cyclamate, saccharin and dulcin. (FIG. 7) Except for cyclamate, all these sweeteners activated the hT1R2-1/hT1R3 chimeric receptor, indicating that the hT1R2 C-terminal 7-transmembrane domain is not required for the interaction of the sweet taste receptor (hT1R2/hT1R3) with these sweeteners. As shown in FIGS. 9-12 cyclamate enhanced the activation of this chimeric receptor by aspartame, D-tryptophan, sucrose, and fructose. As shown in FIG. 13, the proprietary umami ligand '807 induced the activity of this chimeric receptor, and this activity was further enhanced by cyclamate.

In additional experiments, the inventors also tested the effect of various umami tasting compounds and enhancers on this stable cell line including monosodium L-glutamate (MSG), IMP, '807 and '336 on the chimeric HT1R2-1 receptor. It was found that MSG or IMP had no effect on the chimeric sweet-umami taste receptor. Also, IMP had no enhancement effect on the activities of the receptor expressed in the stable cell line, indicating that the hT1R1 N-terminal extracellular domain is apparently required for MSG/IMP interaction with the umami taste receptor (hT1R1/hT1R3). It was also observed using the same stable HEK-293 cell line that two proprietary umami ligands, identified as '807 and '336 strongly activated the chimeric receptor. These results would suggest that the hT1R1 N-terminal domain is apparently not required for these compounds to interact with and activate the umami taste receptor.

The inventors tested the effect of cyclamate as an enhancer because cyclamate is a sweetener the inventors previously demonstrated to interact with the hT1R3 C-terminal 7-transmembrane domain. As mentioned, cyclamate which was previously found to be an agonist of the sweet taste receptor (hT1R2/hT1R3) and an enhancer of the umami taste receptor (hT1R1/hT1R3). Therefore, the inventors conducted experiments elucidating the effect of cyclamate on the response of the subject chimeric hT1R2-1 receptor to natural and synthetic sweet ligands including aspartame, D-tryptophan, sucrose, fructose, and on the effect of '807 and vice versa as well as the effect of '807 on aspartame response.

Particularly as shown in the FIGS. 9-12 it was observed that cyclamate enhanced the response of hT1R2-1 to various sweeteners (aspartame, D-tryptophan, sucrose, fructose) and it was observed that cyclamate alone did not activate the sweet-umami chimeric receptor (hT1R2-1/hT1R3), but enhanced its responses to the sweeteners and umami compounds '807 and '336 in the stable hT1R2-1/hT1R3 cell lines. These results suggest that cyclamate, an agonist of the sweet taste receptor (hT1R2/hT1R3), acts like an enhancer on the sweet-umami chimeric receptor (hT1R2-1/hT1R3).

As mentioned, '807 and '336 were shown to interact with the hT1R1 C-terminal transmembrane domain. Besides activating the sweet-umami chimeric receptor, 807 and 336 also was observed to enhance the chimeric sweet-umami taste receptor activities at lower concentrations.

As noted above, experiments were also conducted using HEK-293 cell lines that expressed the chimeric hT1R1-2 receptor, a chimeric G16gust44 protein, and a rat T1R3 sequence which revealed that this chimeric taste receptor responded to umami tasting compounds and that the activity thereof is enhanced by IMP and GMP.

Therefore, based on the foregoing, chimeric-sweet-umami chimeric receptor or chimeric umami-sweet taste receptors according to the invention and stable or transient cell lines which express these chimeric taste receptor can be used to identify sweet taste enhancers, umami taste enhancers, sweeteners, and umami tasting molecules. Also, these chimeric taste receptors and cell lines which express these chimeric taste receptors can be used in mapping and functional studies to determine at what residues sweet and umami ligands interact with their respective taste receptors. Also, these molecules can be used to elucidate the mechanism of the sweet and umami receptors' activation and enhancement of activation.

As discussed in further detail below, these hybrid receptors can be used in any of the screening assays disclosed in Applicants' earlier T1R related applications including U.S. Ser.

No. 09/897,427 filed on Jul. 3, 2001 and U.S. Ser. No. 10/179,373 filed on Jun. 26, 2002. These patent applications and the references cited therein are incorporated by reference in their entirety herein. Additionally, as discussed below, these hybrid receptors can be expressed using any of the expression vectors, and cells disclosed herein. However, preferred cells for expression include cells typically used in GPCR assays such as HEK-293, CHO, COS, MDK, BHK, monkey L and (frog) oocytes.

In functional cell based assays such as those discussed below the chimeric receptor will preferably be expressed in association with a suitable G protein such as a promiscuous G protein such as Galpha15, Galpha16, transducin, gustducin, a Gq protein, a Gi protein or a chimeric G protein such as a chimeric protein derived from Galpha16 and gustducin. Exemplified herein are chimeric G proteins derived from G16 and transducin or gustducin.

Also, it should be understood that while the application exemplifies specific sweet-umami and chimeric umami-sweet nucleic acid and protein sequences that the invention further contemplates variants thereof, e.g., nucleic acid sequences and polypeptides that poses at least 80% sequence identity therewith, more preferably at least 90% sequence identity therewith, and more typically from 95, 96, 97, 98, 0r 99% sequence identity therewith. Similarly, these chimeric sequences may be expressed in association with wild-type or variant T1R3 sequences, i.e., variants which possess at least 80% sequence identity to human or rodent T1R3, more typically at least 90% sequence identity therewith, and even more typically at lest 95, 96, 97, 98 or 99% sequence identity therewith.

The taste modulatory effect of umami and sweet ligands and enhancers identified using the subject chimeric taste receptors will preferably be confirmed in human or animal taste tests. For example it will be confirmed that they modulate sweet or umami taste alone or in association with other compounds (sweet compound or umami tasting compound). These compounds may be used as flavor additives in various compositions including foods, beverages, medicaments and cosmetics.

Preferably, these assays will utilize a test cell that expresses a DNA encoding an hT1R having one of the amino acid sequences identified infra. However, it is anticipated that fragments, orthologs, variants or chimeras of these receptor polypeptides which retain the functional properties of these chimeric sweet-umami or umami-sweet taste receptors, i.e., respond to some sweet or umami compounds or enhancers thereof compounds, will also be useful in these assays. Examples of such variants include splice variants, single nucleotide polymorphisms, allelic variants, and mutations produced by recombinant or chemical means, or naturally occurring. Means for isolation and expression of T1Rs, which are used in the assays of the present invention and assays which are contemplated for use in the present invention to identify compounds that inhibit activation of these receptors, are set forth below.

Isolation and Expression of T1Rs

Isolation and expression of the T1Rs, or fragments or variants thereof, of the invention can be effected by well-established cloning procedures using probes or primers constructed based on the T1R nucleic acids sequences disclosed in the application. Related T1R sequences may also be identified from human or other species genomic databases using the sequences disclosed herein and known computer-based search technologies, e.g., BLAST sequence searching. In a particular embodiment, the pseudogenes disclosed herein can be used to identify functional alleles or related genes.

Expression vectors can then be used to infect or transfect host cells for the functional expression of these sequences. These genes and vectors can be made and expressed in vitro or in vivo. One of skill will recognize that desired phenotypes for altering and controlling nucleic acid expression can be obtained by modulating the expression or activity of the genes and nucleic acids (e.g., promoters, enhancers and the like) within the vectors of the invention. Any of the known methods described for increasing or decreasing expression or activity can be used. The invention can be practiced in conjunction with any method or protocol known in the art, which are well described in the scientific and patent literature.

Alternatively, these nucleic acids can be synthesized in vitro by well-known chemical synthesis techniques, as described in, e.g., Carruthers, Cold Spring Harbor Symp. Quant. Biol. 47:411-18 (1982); Adams, Am. Chem. Soc., 105:661 (1983); Belousov, Nucleic Acids Res. 25:3440-3444 (1997); Frenkel, Free Radic. Biol. Med. 19:373-380 (1995); Blommers, Biochemistry 33:7886-7896 (1994); Narang, Meth. Enzymol. 68:90 (1979); Brown, Meth. Enzymol. 68:109 (1979); Beaucage, Tetra. Lett. 22:1859 (1981); U.S. Pat. No. 4,458,066. Double-stranded DNA fragments may then be obtained either by synthesizing the complementary strand and annealing the strands together under appropriate conditions, or by adding the complementary strand using DNA polymerase with an appropriate primer sequence.

Techniques for the manipulation of nucleic acids, such as, for example, for generating mutations in sequences, subcloning, labeling probes, sequencing, hybridization and the like are well described in the scientific and patent literature. See, e.g., Sambrook, ed., Molecular Cloning: A Laboratory Manual (2nd ed.), Vols. 1-3, Cold Spring Harbor Laboratory (1989); Ausubel, ed., Current Protocols in Molecular Biology, John Wiley & Sons, Inc., New York (1997); Tijssen, ed., Laboratory Techniques in Biochemistry and Molecular Biology: Hybridization With Nucleic Acid Probes, Part I, Theory and Nucleic Acid Preparation, Elsevier, N.Y. (1993).

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g., fluid or gel precipitin reactions, immunodiffusion, immunoelectrophoresis, radioimmunoassays (RIAs), enzyme-linked immunosorbent assays (ELISAs), immuno-fluorescent assays, Southern analysis, Northern analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography.

Oligonucleotide primers may be used to amplify nucleic acids encoding a T1R ligand-binding region. The nucleic acids described herein can also be cloned or measured quantitatively using amplification techniques. Amplification methods are also well known in the art, and include, e.g., polymerase chain reaction (PCR) (Innis ed., PCR Protocols, a Guide to Methods and Applications, Academic Press, N.Y. (1990); Innis ed., PCR Strategies, Academic Press, Inc., N.Y. (1995)); ligase chain reaction (LCR) (Wu, Genomics, 4:560 (1989); Landegren, Science, 241:1077 (1988); Barringer, Gene, 89:117 (1990)); transcription amplification (Kwoh, PNAS, 86:1173 (1989)); self-sustained sequence replication (Guatelli, PNAS, 87:1874 (1990)); Q Beta replicase amplification (Smith, J. Clin. Microbiol., 35:1477-91 (1997)); automated Q-beta replicase amplification assay (Burg, Mol. Cell. Probes, 10:257-71 (1996)); and other RNA polymerase mediated techniques (e.g., NASBA, Cangene, Mississauga, Ontario). See also, Berger, Methods Enzymol., 152:307-16 (1987); Sambrook; Ausubel; U.S. Pat. Nos. 4,683,195 and 4,683,202; Sooknanan, Biotechnology, 13:563-64 (1995).

Once amplified, the nucleic acids, either individually or as libraries, may be cloned according to methods known in the art, if desired, into any of a variety of vectors using routine molecular biological methods; methods for cloning in vitro amplified nucleic acids are described, e.g., U.S. Pat. No. 5,426,039. To facilitate cloning of amplified sequences, restriction enzyme sites can be "built into" the PCR primer pair. For example, Pst I and Bsp E1 sites were designed into the exemplary primer pairs of the invention. These particular restriction sites have a sequence that, when ligated, are "in-frame" with respect to the 7-membrane receptor "donor" coding sequence into which they are spliced (the ligand-binding region coding sequence is internal to the 7-membrane polypeptide, thus, if it is desired that the construct be translated downstream of a restriction enzyme splice site, out of frame results should be avoided; this may not be necessary if the inserted ligand-binding region comprises substantially most of the transmembrane VII region). The primers can be designed to retain the original sequence of the "donor" 7-membrane receptor. Alternatively, the primers can encode amino acid residues that are conservative substitutions (e.g., hydrophobic for hydrophobic residue, see above discussion) or functionally benign substitutions (e.g., do not prevent plasma membrane insertion, cause cleavage by peptidase, cause abnormal folding of receptor, and the like).

The primer pairs may be designed to selectively amplify ligand-binding regions of T1R proteins. These binding regions may vary for different ligands; thus, what may be a minimal binding region for one ligand, may be too limiting for a second potential ligand. Thus, binding regions of different sizes comprising different domain structures may be amplified; for example, transmembrane (TM) domains II through VII, III through VII, III through VI or II through VI, or variations thereof (e.g., only a subsequence of a particular domain, mixing the order of the domains, and the like), of a 7-transmembrane T1R.

As domain structures and sequence of many 7-membrane T1R proteins are known, the skilled artisan can readily select domain-flanking and internal domain sequences as model sequences to design degenerate amplification primer pairs. For example, a nucleic acid sequence encoding domain regions II through VII can be generated by PCR amplification using a primer pair. To amplify a nucleic acid comprising transmembrane domain I (TM I) sequence, a degenerate primer can be designed from a nucleic acid that encodes the amino acid sequence of the T1R family consensus sequence 1 described above. Such a degenerate primer can be used to generate a binding region incorporating TM I through TM III, TM I through TM IV, TM I through TM V, TM I through TM VI or TM I through TM VII). Other degenerate primers can be designed based on the other T1R family consensus sequences provided herein. Such a degenerate primer can be used to generate a binding region incorporating TM III through TM IV, TM III through TM V, TM III through TM VI or TM III through TM VII.

Paradigms to design degenerate primer pairs are well known in the art. For example, a COnsensus-DEgenerate Hybrid Oligonucleotide Primer (CODEHOP) strategy computer program is accessible as http://blocks.fhcrc.org/code-hop.html, and is directly linked from the BlockMaker multiple sequence alignment site for hybrid primer prediction beginning with a set of related protein sequences, as known taste receptor ligand-binding regions (see, e.g., Rose, Nucleic Acids Res., 26:1628-35 (1998); Singh, Biotechniques, 24:318-19 (1998)).

Means to synthesize oligonucleotide primer pairs are well known in the art. "Natural" base pairs or synthetic base pairs can be used. For example, use of artificial nucleobases offers a versatile approach to manipulate primer sequence and generate a more complex mixture of amplification products. Various families of artificial nucleobases are capable of assuming multiple hydrogen bonding orientations through internal bond rotations to provide a means for degenerate molecular recognition. Incorporation of these analogs into a single position of a PCR primer allows for generation of a complex library of amplification products. See, e.g., Hoops, Nucleic Acids Res., 25:4866-71 (1997). Nonpolar molecules can also be used to mimic the shape of natural DNA bases. A non-hydrogen-bonding shape mimic for adenine can replicate efficiently and selectively against a nonpolar shape mimic for thymine (see, e.g., Morales, Nat. Struct. Biol., 5:950-54 (1998)). For example, two degenerate bases can be the pyrimidine base 6H, 8H-3,4-dihydropyrimido[4,5-c][1,2]oxazin-7-one or the purine base N6-methoxy-2,6-diaminopurine (see, e.g., Hill, PNAS, 95:4258-63 (1998)). Exemplary degenerate primers of the invention incorporate the nucleobase analog 5'-Dimethoxytrityl-N-benzoyl-2'-deoxy-Cytidine,3'-[(2-cyanoethyl)-(N,N-diisopropyl)]-phosphoramid-ite (the term "P" in the sequences, see above). This pyrimidine analog hydrogen bonds with purines, including A and G residues.

Polymorphic variants, alleles, and interspecies homologs that are substantially identical to a taste receptor disclosed herein can be isolated using the nucleic acid probes described above. Alternatively, expression libraries can be used to clone T1R polypeptides and polymorphic variants, alleles, and interspecies homologs thereof, by detecting expressed homologs immunologically with antisera or purified antibodies made against a T1R polypeptide, which also recognize and selectively bind to the T1R homolog.

Nucleic acids that encode ligand-binding regions of taste receptors may be generated by amplification (e.g., PCR) of appropriate nucleic acid sequences using appropriate (perfect or degenerate) primer pairs. The amplified nucleic acid can be genomic DNA from any cell or tissue or mRNA or cDNA derived from taste receptor-expressing cells.

In one embodiment, hybrid protein-coding sequences comprising nucleic acids encoding chimeric or native T1Rs fused to a translocation sequences may be constructed. Also provided are hybrid T1Rs comprising the translocation motifs and taste eliciting compound-binding regions of other families of chemosensory receptors, particularly taste receptors. These nucleic acid sequences can be operably linked to transcriptional or translational control elements, e.g., transcription and translation initiation sequences, promoters and enhancers, transcription and translation terminators, polyadenylation sequences, and other sequences useful for transcribing DNA into RNA. In construction of recombinant expression cassettes, vectors, and transgenics, a promoter fragment can be employed to direct expression of the desired nucleic acid in all desired cells or tissues.

In another embodiment, fusion proteins may include C-terminal or N-terminal translocation sequences. Further, fusion proteins can comprise additional elements, e.g., for protein detection, purification, or other applications. Detection and purification facilitating domains include, e.g., metal chelating peptides such as polyhistidine tracts, histidine-tryptophan modules, or other domains that allow purification on immobilized metals; maltose binding protein; protein A domains that allow purification on immobilized immunoglobulin; or the domain utilized in the FLAGS extension/affinity purification system (Immunex Corp, Seattle Wash.).

The inclusion of a cleavable linker sequences such as Factor Xa (see, e.g., Ottavi, Biochimie, 80:289-93 (1998)), subtilisin protease recognition motif (see, e.g., Polyak, Protein Eng., 10:615-19 (1997)); enterokinase (Invitrogen, San Diego, Calif.), and the like, between the translocation domain (for efficient plasma membrane expression) and the rest of the newly translated polypeptide may be useful to facilitate purification. For example, one construct can include a polypeptide encoding a nucleic acid sequence linked to six histidine residues followed by a thioredoxin, an enterokinase cleavage site (see, e.g., Williams, Biochemistry, 34:1787-97 (1995)), and an C-terminal translocation domain. The histidine residues facilitate detection and purification while the enterokinase cleavage site provides a means for purifying the desired protein(s) from the remainder of the fusion protein. Technology pertaining to vectors encoding fusion proteins and application of fusion proteins are well described in the scientific and patent literature (see, e.g., Kroll, DNA Cell. Biol. 12:441-53 (1993)).

Expression vectors, either as individual expression vectors or as libraries of expression vectors, comprising the ligand-binding region encoding sequences may be introduced into a genome or into the cytoplasm or a nucleus of a cell and expressed by a variety of conventional techniques, well described in the scientific and patent literature. See, e.g., Roberts, Nature, 328:731 (1987); Berger supra; Schneider, Protein Expr. Purif., 6435:10 (1995); Sambrook; Tijssen; Ausubel. Product information from manufacturers of biological reagents and experimental equipment also provide information regarding known biological methods. The vectors can be isolated from natural sources, obtained from such sources as ATCC or GenBank libraries, or prepared by synthetic or recombinant methods.

The nucleic acids can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required. For example, the marker may encode antibiotic resistance (e.g., chloramphenicol, kanamycin, G418, bleomycin, hygromycin) or herbicide resistance (e.g., chlorosulfuron or Basta) to permit selection of those cells transformed with the desired DNA sequences (see, e.g., Blondelet-Rouault, Gene, 190:315-17 (1997); Aubrecht, J. Pharmacol. Exp. Ther., 281:992-97 (1997)). Because selectable marker genes conferring resistance to substrates like neomycin or hygromycin can only be utilized in tissue culture, chemoresistance genes are also used as selectable markers in vitro and in vivo.

A chimeric nucleic acid sequence may encode a T1R ligand-binding region within any 7-transmembrane polypeptide. Because 7-transmembrane receptor polypeptides have similar primary sequences and secondary and tertiary structures, structural domains (e.g., extracellular domain, TM domains, cytoplasmic domain, etc.) can be readily identified by sequence analysis. For example, homology modeling, Fourier analysis and helical periodicity detection can identify and characterize the seven domains with a 7-transmembrane receptor sequence. Fast Fourier Transform (FFT) algorithms can be used to assess the dominant periods that characterize profiles of the hydrophobicity and variability of analyzed sequences. Periodicity detection enhancement and alpha helical periodicity index can be done as by, e.g., Donnelly, Protein Sci., 2:55-70 (1993). Other alignment and modeling algorithms are well known in the art (see, e.g., Peitsch, Receptors Channels, 4:161-64 (1996); Kyte & Doolittle, J. Md. Biol., 157:105-32 (1982); and Cronet, Protein Eng., 6:59-64 (1993).

The present invention also includes not only the nucleic acid molecules and polypeptides having the specified native and chimeric T1R nucleic and amino acid sequences, but also fragments thereof, particularly fragments of, e.g., 40, 60, 80, 100, 150, 200, or 250 nucleotides, or more, as well as polypeptide fragments of, e.g., 10, 20, 30, 50, 70, 100, or 150 amino acids, or more. Optionally, the nucleic acid fragments can encode an antigenic polypeptide that is capable of binding to an antibody raised against a T1R family member. Further, a protein fragment of the invention can optionally be an antigenic fragment that is capable of binding to an antibody raised against a T1R family member.

Also contemplated are chimeric proteins, comprising at least 10, 20, 30, 50, 70, 100, or 150 amino acids, or more, of one of at least one of the T1R polypeptides described herein, coupled to additional amino acids representing all or part of another GPCR, preferably a member of the 7 transmembrane superfamily. These chimeras can be made from the instant receptors and another GPCR, or they can be made by combining two or more of the present receptors. In one embodiment, one portion of the chimera corresponds to, or is derived from the transmembrane domain of a T1R polypeptide of the invention. In another embodiment, one portion of the chimera corresponds to, or is derived from the one or more of the transmembrane regions of a T1R polypeptide described herein, and the remaining portion or portions can come from another GPCR. Chimeric receptors are well known in the art, and the techniques for creating them and the selection and boundaries of domains or fragments of G Protein-Coupled Receptors for incorporation therein are also well known. Thus, this knowledge of those skilled in the art can readily be used to create such chimeric receptors. The use of such chimeric receptors can provide, for example, a taste selectivity characteristic of one of the receptors specifically disclosed herein, coupled with the signal transduction characteristics of another receptor, such as a well known receptor used in prior art assay systems.

For example, a region such as a ligand-binding region, an extracellular domain, a transmembrane domain, a transmembrane domain, a cytoplasmic domain, an N-terminal domain, a C-terminal domain, or any combination thereof, can be covalently linked to a heterologous protein. For instance, a T1R transmembrane region can be linked to a heterologous GPCR transmembrane domain, or a heterologous GPCR extracellular domain can be linked to a T1R transmembrane region. Other heterologous proteins of choice can include, e.g., green fluorescent protein, .beta.-galactosidase polypeptides, glutamate receptor, and the rhodopsin polypeptides, e.g., N-terminal fragments of rhodopsin e.g., bovine rhodopsin.

It is also within the scope of the invention to use different host cells for expressing the T1Rs, fragments, or variants of the invention. To obtain high levels of expression of a cloned gene or nucleic acid, such as cDNAs encoding the T1Rs, fragments, or variants of the invention, one of skill typically subclones the nucleic acid sequence of interest into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. Preferably, eukaryotic expression systems are used to express the subject hT1R receptor.

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al.) It is only necessary that the particular genetic engineering procedure used be capable of successfully introducing at lest one nucleic acid molecule into the host cell capable of expressing the T1R, fragment, or variant of interest.

After the expression vector is introduced into the cells, the transfected cells are cultured under conditions favoring expression of the receptor, fragment, or variant of interest, which is then recovered from the culture using standard techniques. Examples of such techniques are well known in the art. See, e.g., WO 00/06593, which is incorporated by reference in a manner consistent with this disclosure.

Assays for Detection of Compounds that Modulate the Activity of a T1R According to the Invention Methods and compositions for determining whether a test compound specifically binds to a T1R polypeptide of the invention, both in vitro and in vivo are described below. Many aspects of cell physiology can be monitored to assess the effect of ligand-binding to a naturally occurring or chimeric T1Rs. These assays may be performed on intact cells expressing a T1R polypeptide, on permeabilized cells, or on membrane fractions produced by standard methods.

Taste receptors bind taste eliciting compounds and initiate the transduction of chemical stimuli into electrical signals. An activated or inhibited G protein will in turn alter the properties of target enzymes, channels, and other effector proteins. Some examples are the activation of cGMP phosphodiesterase by transducin in the visual system, adenylate cyclase by the stimulatory G protein, phospholipase C by Gq and other cognate G proteins, and modulation of diverse channels by Gi and other G proteins. Downstream consequences can also be examined such as generation of diacyl glycerol and IP3 by phospholipase C, and in turn, for calcium mobilization by IP3.

The subject chimeric T1R polypeptides of the assay will typically be selected from a polypeptide having a sequence contained in SEQ ID NOS.:2 and 4 or fragments or conservatively modified variants thereof.

Alternatively, the chimeric T1R proteins or polypeptides of the assay can be derived from a eukaryotic host cell, and can include an amino acid sequence having amino acid sequence identity to SEQ ID NO:s.:2 or 4 or conservatively modified variants thereof. Generally, the amino acid sequence identity will be at least 30% preferably 30-40%, more specifically 50-60, 70%, 75%, 80%, 85%, 90%, 95%, 96%, 97%, 98%, or 99%. Optionally, the T1R proteins or polypeptides of the assays can comprise a region of a T1R polypeptide, such as an extracellular domain, transmembrane region, cytoplasmic domain, ligand-binding domain, and the like. Optionally, the T1R polypeptide, or a portion thereof, can be covalently linked to a heterologous protein to create a chimeric protein used in the assays described herein.

Modulators of T1R activity may be tested using T1R proteins or polypeptides as described above, either recombinant or naturally occurring. The T1R proteins or polypeptides can be isolated, expressed in a cell, expressed in a membrane derived from a cell, expressed in tissue or in an animal, either recombinant or naturally occurring. For example, tongue slices, dissociated cells from a tongue, transformed cells, or membranes can be used. Modulation can be tested using one of the in vitro or in vivo assays described herein.

Detection of Modulators

Compositions and methods for determining whether a test compound specifically binds to a T1R receptor of the invention, both in vitro and in vivo, are described below. Many aspects of cell physiology can be monitored to assess the effect of ligand binding to a T1R polypeptide of the invention. These assays may be performed on intact cells expressing a chemosensory receptor, on permeabilized cells, or on membrane fractions produced by standard methods or in vitro using de novo synthesized proteins.

In vivo, taste receptors bind to taste modulatory compounds and initiate the transduction of chemical stimuli into electrical signals. An activated or inhibited G protein will in turn alter the properties of target enzymes, channels, and other effector proteins. Some examples are the activation of cGMP phosphodiesterase by transducin in the visual system, adenylate cyclase by the stimulatory G protein, phospholipase C by Gq and other cognate G proteins, and modulation of diverse channels by Gi and other G proteins. Downstream consequences can also be examined such as generation of diacyl glycerol and IP3 by phospholipase C, and in turn, for calcium mobilization by IP3.

Alternatively, the T1R proteins or polypeptides of the assay can be derived from a eukaryotic host cell and can include an amino acid subsequence having amino acid sequence identity to the T1R polypeptides disclosed herein, or fragments or conservatively modified variants thereof. Generally, the amino acid sequence identity will be at least 35 to 50%, or optionally 75%, 85%, 90%, 95%, 96%, 97%, 98%, or 99%. Optionally, the T1R proteins or polypeptides of the assays can comprise a domain of a T1R protein, such as an extracellular domain, transmembrane region, transmembrane domain, cytoplasmic domain, ligand-binding domain, and the like. Further, as described above, the T1R protein or a domain thereof can be covalently linked to a heterologous protein to create a chimeric protein used in the assays described herein.

Modulators of T1R receptor activity are tested using T1R proteins or polypeptides as described above, either recombinant or naturally occurring. The T1R proteins or polypeptides can be isolated, expressed in a cell, expressed in a membrane derived from a cell, expressed in tissue or in an animal, either recombinant or naturally occurring. For example, tongue slices, dissociated cells from a tongue, transformed cells, or membranes can be used. Modulation can be tested using one of the in vitro or in vivo assays described herein.

1. In Vitro Binding Assays

Taste transduction can also be examined in vitro with soluble or solid state reactions, using the T1R polypeptides of the invention. In a particular embodiment, T1R ligand-binding domains can be used in vitro in soluble or solid state reactions to assay for ligand binding.

It is possible that the ligand-binding domain may be formed by the N-terminal domain together with additional portions of the extracellular domain, such as the extracellular loops of the transmembrane domain.

In vitro binding assays have been used with other GPCRs, such as the metabotropic glutamate receptors (see, e.g., Han and Hampson, J. Biol. Chem. 274:10008-10013 (1999)). These assays might involve displacing a radioactively or fluorescently labeled ligand, measuring changes in intrinsic fluorescence or changes in proteolytic susceptibility, etc.

Ligand binding to a T1R polypeptide according to the invention can be tested in solution, in a bilayer membrane, optionally attached to a solid phase, in a lipid monolayer, or in vesicles. Binding of a modulator can be tested using, e.g., changes in spectroscopic characteristics (e.g., fluorescence, absorbance, refractive index) hydrodynamic (e.g., shape), chromatographic, or solubility properties.

In a preferred embodiment of the invention, a $[^{35}S]$GTPγS binding assay is used. As described above, upon activation of a GPCR, the Gα subunit of the G protein complex is stimulated to exchange bound GDP for GTP. Ligand-mediated stimulation of G protein exchange activity can be measured in a biochemical assay measuring the binding of added radioactively labeled $[^{35}S]$GTPγS to the G protein in the presence of a putative ligand. Typically, membranes containing the chemosensory receptor of interest are mixed with a G protein. Potential inhibitors and/or activators and $[^{35}S]$GTPγS are added to the assay, and binding of $[^{35}S]$GTPγS to the G protein is measured. Binding can be measured by liquid scintillation counting or by any other means known in the art, including scintillation proximity assays (SPA). In other assays formats, fluorescently labeled GTPγS can be utilized.

2. Fluorescence Polarization Assays

In another embodiment, Fluorescence Polarization ("FP") based assays may be used to detect and monitor ligand binding. Fluorescence polarization is a versatile laboratory technique for measuring equilibrium binding, nucleic acid hybridization, and enzymatic activity. Fluorescence polarization assays are homogeneous in that they do not require a separation step such as centrifugation, filtration, chromatography, precipitation, or electrophoresis. These assays are done in real time, directly in solution and do not require an immobilized phase. Polarization values can be measured repeatedly and after the addition of reagents since measuring the polarization is rapid and does not destroy the sample. Generally, this technique can be used to measure polarization values of fluorophores from low picomolar to micromolar levels. This section describes how fluorescence polarization can be used in a simple and quantitative way to measure the binding of ligands to the T1R polypeptides of the invention.

When a fluorescently labeled molecule is excited with plane polarized light, it emits light that has a degree of polarization that is inversely proportional to its molecular rotation. Large fluorescently labeled molecules remain relatively stationary during the excited state (4 nanoseconds in the case of fluorescein) and the polarization of the light remains relatively constant between excitation and emission. Small fluorescently labeled molecules rotate rapidly during the excited state and the polarization changes significantly between excitation and emission. Therefore, small molecules have low polarization values and large molecules have high polarization values. For example, a single-stranded fluorescein-labeled oligonucleotide has a relatively low polarization value but when it is hybridized to a complementary strand, it has a higher polarization value. When using FP to detect and monitor taste eliciting compound-binding which may activate or inhibit the chemosensory receptors of the invention, fluorescence-labeled taste eliciting compounds or auto-fluorescent taste eliciting compounds may be used.

Fluorescence polarization (P) is defined as:

$$P = \frac{[Int_{par} - Int_{perp}]}{[Int_{par} + Int_{perp}]}$$

Where $Int_{par}$ is the intensity of the emission light parallel to the excitation light plane and $Int_{perp}$ is the intensity of the emission light perpendicular to the excitation light plane. P, being a ratio of light intensities, is a dimensionless number. For example, the Beacon™ and Beacon 2000™. System may be used in connection with these assays. Such systems typically express polarization in millipolarization units (1 Polarization Unit=1000 mP Units).

The relationship between molecular rotation and size is described by the Perrin equation and the reader is referred to Jolley, M. E. (1991) in Journal of Analytical Toxicology, pp. 236-240 incorporated by reference, which gives a thorough explanation of this equation. Summarily, the Perrin equation states that polarization is directly proportional to the rotational relaxation time, the time that it takes a molecule to rotate through an angle of approximately 68.5°. Rotational relaxation time is related to viscosity (eta.), absolute temperature (T), molecular volume (V), and the gas constant (R) by the following equation: 2(Rotational Relaxation Time)=3 V RT.

The rotational relaxation time is small (~ nanosecond) for small molecules (e.g. fluorescein) and large (~100 nanoseconds) for large molecules (e.g. immunoglobulins). If viscosity and temperature are held constant, rotational relaxation time, and therefore polarization, is directly related to the molecular volume. Changes in molecular volume may be due to interactions with other molecules, dissociation, polymerization, degradation, hybridization, or conformational changes of the fluorescently labeled molecule. For example, fluorescence polarization has been used to measure enzymatic cleavage of large fluorescein labeled polymers by proteases, DNases, and RNases. It also has been used to measure equilibrium binding for protein/protein interactions, antibody/antigen binding, and protein/DNA binding.

A. Solid State and Soluble High Throughput Assays

In yet another embodiment, the invention provides soluble assays using a T1R polypeptide; or a cell or tissue expressing a T1R polypeptide. In another embodiment, the invention provides solid phase based in vitro assays in a high throughput format, where the T1R polypeptide, or cell or tissue expressing the T1R polypeptide is attached to a solid phase substrate or a taste stimulating compound and contacted with a T1R receptor, and binding detected using an appropriate tag or antibody raised against the T1R receptor.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 1000 to about 1500 different compounds. It is also possible to assay multiple compounds in each plate well. It is possible to assay several different plates per day; assay screens for up to about 6,000-20,000 different compounds is possible using the integrated systems of the invention. More recently, microfluidic approaches to reagent manipulation have been developed.

The molecule of interest can be bound to the solid state component, directly or indirectly, via covalent or non-covalent linkage, e.g., via a tag. The tag can be any of a variety of components. In general, a molecule which binds the tag (a tag binder) is fixed to a solid support, and the tagged molecule of interest (e.g., the taste transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available and appropriate tag binders (see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, The Adhesion Molecule Facts Book I (1993)). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, J. Am. Chem. Soc., 85:2149-2154 (1963) (describing solid phase synthesis of, e.g., peptides); Geysen et al., J. Immun. Meth., 102:259-274 (1987) (describing synthesis of solid phase components on pins); Frank & Doring, Tetrahedron, 44:60316040 (1988) (describing synthesis of various peptide sequences on cellulose disks); Fodor et al., Science, 251:767-777 (1991); Sheldon et al., Clinical Chemistry, 39(4):718-719 (1993); and Kozal et al., Nature Medicine, 2(7):753759 (1996) (all describing arrays of biopolymers fixed to solid substrates). Non-chemical approaches for fixing tag binders to substrates include other common methods, such as heat, cross-linking by UV radiation, and the like.

3. Cell-Based Assays

In one preferred embodiment, a T1R protein is expressed in a eukaryotic cell either in unmodified forms or as chimeric, variant or truncated receptors with or preferably without a heterologous, chaperone sequence that facilitates its maturation and targeting through the secretory pathway. Such T1R polypeptides can be expressed in any eukaryotic cell, such as HEK-293 cells. Preferably, the cells comprise a functional G protein, e.g., $G_{\alpha 15}$, or a chimeric $G_{\alpha 16}$, gustducin or transducin or a chimeric G protein such as G16gust44 that is capable of coupling the chimeric receptor to an intracellular signaling pathway or to a signaling protein such as phospholipase C. Activation of T1R receptors in such cells can be detected using any standard method, such as by detecting changes in intracellular calcium by detecting FURA-2 dependent fluorescence in the cell. Such an assay is the basis of the experimental findings presented in this application.

Activated GPCR receptors often are substrates for kinases that phosphorylate the C-terminal tail of the receptor (and possibly other sites as well). Thus, activators will promote the transfer of $^{32}P$ from radiolabeled ATP to the receptor, which can be assayed with a scintillation counter. The phosphorylation of the C-terminal tail will promote the binding of arrestin-like proteins and will interfere with the binding of G proteins. For a general review of GPCR signal transduction and methods of assaying signal transduction, see, e.g., Methods in Enzymology, vols. 237 and 238 (1994) and volume 96 (1983); Bourne et al., Nature, 10:349:117-27 (1991); Bourne et al., Nature, 348:125-32 (1990); Pitcher et al., Annu. Rev. Biochem., 67:653-92 (1998).

T1R modulation may be assayed by comparing the response of chimeric T1R polypeptides according to the invention treated with a putative T1R modulator to the response of an untreated control sample or a sample containing a known "positive" control. Such putative T1R modulators can include molecules that either inhibit or activate T1R polypeptide activity. In one embodiment, control samples treated with a compound that activates the T1R are assigned a relative T1R activity value of 100. Inhibition of a T1R polypeptide is achieved when the T1R activity value relative to the control sample is about 90%, optionally 50%, optionally 25-0%. Activation of a T1R polypeptide is achieved when the T1R activity value relative to the control is 110%, optionally 150%, 200-500%, or 1000-2000%.

Changes in ion flux may be assessed by determining changes in ionic polarization (i.e., electrical potential) of the cell or membrane expressing a T1R polypeptide. One means to determine changes in cellular polarization is by measuring changes in current (thereby measuring changes in polarization) with voltage-clamp and patch-clamp techniques (see, e.g., the "cell-attached" mode, the "inside-out" mode, and the "whole cell" mode, e.g., Ackerman et al., New Engl. J Med., 336:1575-1595 (1997)). Whole cell currents are conveniently determined using the standard. Other known assays include: radiolabeled ion flux assays and fluorescence assays using voltage-sensitive dyes (see, e.g., Vestergarrd-Bogind et al., J. Membrane Biol., 88:67-75 (1988); Gonzales & Tsien, Chem. Biol., 4:269-277 (1997); Daniel et al., J. Pharmacol. Meth., 25:185-193 (1991); Holevinsky et al., J. Membrane Biology, 137:59-70 (1994)).

The effects of the test compounds upon the function of the polypeptides can be measured by examining any of the parameters described above. Any suitable physiological change that affects GPCR activity can be used to assess the influence of a test compound on the polypeptides of this invention. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as Ca.2+, IP3, cGMP, or cAMP.

Preferred assays for GPCRs include cells that are loaded with ion or voltage sensitive dyes to report receptor activity. Assays for determining activity of such receptors can also use known agonists and antagonists for other G protein-coupled receptors as controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Among the ion-sensitive indicators and voltage probes that may be employed are those disclosed in the Molecular Probes 1997 Catalog. For G protein-coupled receptors, promiscuous G proteins such as $G_{\alpha15}$ and $G_{\alpha16}$ can be used in the assay of choice (Wilkie et al., Proc. Nat'l Acad. Sci., 88:10049-10053 (1991)). Alternatively, other G proteins such as gustducin, transducin and chimeric G proteins such as G$\alpha$16gust44 or G16g44 may be used.

Receptor activation initiates subsequent intracellular events, e.g., increases in second messengers. Activation of some G protein-coupled receptors stimulates the formation of inositol triphosphate (IP3) through phospholipase C-mediated hydrolysis of phosphatidylinositol (Berridge & Irvine, Nature, 312:315-21 (1984)). IP3 in turn stimulates the release of intracellular calcium ion stores. Thus, a change in cytoplasmic calcium ion levels, or a change in second messenger levels such as IP3 can be used to assess G protein-coupled receptor function. Cells expressing such G protein-coupled receptors may exhibit increased cytoplasmic calcium levels as a result of contribution from both calcium release from intracellular stores and extracellular calcium entry via plasma membrane ion channels.

In a preferred embodiment, T1R polypeptide activity is measured by expressing T1R gene in a heterologous cell with a promiscuous G protein that links the receptor to a phospholipase C signal transduction pathway (see Offermanns & Simon, J. Biol. Chem., 270:15175-15180 (1995)). Preferably, the cell line is HEK-293 (which does not normally express T1R genes) and the promiscuous G protein is $G_{\alpha15}$ (Offermanns & Simon, supra) or a chimeric G protein such as G$\alpha$16gust44. Modulation of taste transduction is assayed by measuring changes in intracellular $Ca^{2+}$ levels, which change in response to modulation of the T1R signal transduction pathway via administration of a molecule that associates with the T1R polypeptide. Changes in $Ca^{2+}$ levels are optionally measured using fluorescent $Ca^{2+}$ indicator dyes and fluorometric imaging.

In another embodiment, phosphatidyl inositol (PI) hydrolysis can be analyzed according to U.S. Pat. No. 5,436,128, herein incorporated by reference. Briefly, the assay involves labeling of cells with 3H-myoinositol for 48 or more hrs. The labeled cells are treated with a test compound for one hour. The treated cells are lysed and extracted in chloroform-methanol-water after which the inositol phosphates were separated by ion exchange chromatography and quantified by scintillation counting. Fold stimulation is determined by calculating the ratio of cpm in the presence of agonist, to cpm in the presence of buffer control. Likewise, fold inhibition is determined by calculating the ratio of cpm in the presence of antagonist, to cpm in the presence of buffer control (which may or may not contain an agonist).

Other receptor assays can involve determining the level of intracellular cyclic nucleotides, e.g., cAMP or cGMP. In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. In one embodiment, the changes in intracellular cAMP or cGMP can be measured using immunoassays. The method described in Offermanns & Simon, J. Bio. Chem., 270:15175-15180 (1995), may be used to determine the level of cAMP. Also, the method described in Felley-Bosco et al., Am. J. Resp. Cell and Mol. Biol., 11:159-164 (1994), may be used to determine the level of cGMP. Further, an assay kit for measuring cAMP and/or cGMP is described in U.S. Pat. No. 4,115,538, herein incorporated by reference.

In another embodiment, transcription levels can be measured to assess the effects of a test compound on signal transduction. A host cell containing T1R polypeptide of interest is contacted with a test compound for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays. Alternatively, transcription based assays using a reporter gene may be used as described in U.S. Pat. No. 5,436,128, herein incorporated by reference. The reporter genes can be, e.g., chloramphenicol acetyltransferase, luciferase, beta-galactosidase, beta-lactamase and alkaline phosphatase. Furthermore, the protein of interest can be used as an indirect reporter via attachment to a second reporter such as green fluorescent protein (see, e.g., Mistili & Spector, Nature Biotechnology, 15:961-964 (1997)).

The amount of transcription is then compared to the amount of transcription in either the same cell in the absence of the test compound, or it may be compared with the amount of transcription in a substantially identical cell that lacks the T1R polypeptide(s) of interest. A substantially identical cell may be derived from the same cells from which the recombinant cell was prepared but which had not been modified by introduction of heterologous DNA. Any difference in the amount of transcription indicates that the test compound has in some manner altered the activity of the T1R polypeptide of interest.

4. Transgenic Non-human Animals Expressing Chemosensory Receptors

Non-human animals expressing one or more taste receptor sequences of the invention can also be used for receptor assays. Such expression can be used to determine whether a test compound specifically binds to a mammalian taste transmembrane receptor complex in vivo by contacting a non-human animal stably or transiently transfected with nucleic acids encoding chemosensory receptors or ligand-binding regions thereof with a test compound and determining whether the animal reacts to the test compound by specifically binding to the receptor polypeptide complex.

Animals transfected or infected with the vectors of the invention are particularly useful for assays to identify and characterize taste stimuli that can bind to a specific or sets of receptors. Such vector-infected animals expressing human taste receptor sequences can be used for in vivo screening of taste stimuli and their effect on, e.g., cell physiology (e.g., on taste neurons), on the CNS, or behavior.

Means to infect/express the nucleic acids and vectors, either individually or as libraries, are well known in the art. A variety of individual cell, organ, or whole animal parameters can be measured by a variety of means. The T1R sequences of the invention can be for example expressed in animal taste tissues by delivery with an infecting agent, e.g., adenovirus expression vector.

The endogenous taste receptor genes can remain functional and wild-type (native) activity can still be present. In other situations, where it is desirable that all taste receptor activity is by the introduced exogenous hybrid receptor, use of a knockout line is preferred. Methods for the construction of non-human transgenic animals, particularly transgenic mice, and the selection and preparation of recombinant constructs for generating transformed cells are well known in the art.

Construction of a "knockout" cell and animal is based on the premise that the level of expression of a particular gene in a mammalian cell can be decreased or completely abrogated by introducing into the genome a new DNA sequence that serves to interrupt some portion of the DNA sequence of the gene to be suppressed. Also, "gene trap insertion" can be used to disrupt a host gene, and mouse embryonic stem (ES) cells can be used to produce knockout transgenic animals (see, e.g., Holzschu, Transgenic Res 6:97-106 (1997)). The insertion of the exogenous is typically by homologous recombination between complementary nucleic acid sequences. The exogenous sequence is some portion of the target gene to be modified, such as exonic, intronic or transcriptional regulatory sequences, or any genomic sequence which is able to affect the level of the target gene's expression; or a combination thereof. Gene targeting via homologous recombination in pluripotential embryonic stem cells allows one to modify precisely the genomic sequence of interest. Any technique can be used to create, screen for, propagate, a knockout animal, e.g., see Bijvoet, Hum. Mol. Genet. 7:53-62 (1998); Moreadith, J. Mol. Med. 75:208-216 (1997); Tojo, Cytotechnology 19:161-165 (1995); Mudgett, Methods Mol. Biol. 48:167-184 (1995); Longo, Transgenic Res. 6:321-328 (1997); U.S. Pat. Nos. 5,616,491; 5,464,764; 5,631,153; 5,487,992; 5,627,059; 5,272,071; WO 91/09955; WO 93/09222; WO 96/29411; WO 95/31560; WO 91/12650.

The nucleic acids of the invention can also be used as reagents to produce "knockout" human cells and their progeny. Likewise, the nucleic acids of the invention can also be used as reagents to produce "knock-ins" in mice. The human or rat T1R gene sequences can replace the orthologs T1R in the mouse genome. In this way, a mouse expressing a human or rat T1R is produced. This mouse can then be used to analyze the function of human or rat T1Rs, and to identify ligands for such T1Rs.

Modulators

The compounds tested as modulators of a T1R family member can be any small chemical compound, or a biological entity, such as a protein, sugar, nucleic acid or lipid. Alternatively, modulators can be genetically altered versions of a T1R family member. Typically, test compounds may be small chemical molecules and peptides. Essentially any chemical compound can be used as a potential modulator or ligand in the assays of the invention, although most often compounds can be dissolved in aqueous or organic (especially DMSO-based) solutions are used. The assays may be designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In one embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual consumer products.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res., 37:487-93 (1991) and Houghton et al., Nature, 354:84-88 (1991)). Other chemistries for generating chemical diversity libraries can also be used. Such chemistries include, but are not limited to: peptoids (e.g., WO 91/19735), encoded peptides (e.g., WO 93/20242), random bio-oligomers (e.g., WO 92/00091), benzodiazepines (e.g., U.S. Pat. No. 5,288,514), diversomers such as hydantoins, benzodiazepines and dipeptides (Hobbs et al., PNAS., 90:6909-13 (1993)), vinylogous polypeptides (Hagihara et al., J. Amer. Chem. Soc., 114:6568 (1992)), nonpeptidal peptidomimetics with glucose scaffolding (Hirschmann et al., J. Amer. Chem. Soc., 114:9217-18 (1992)), analogous organic syntheses of small compound libraries (Chen et al., J. Amer. Chem. Soc., 116:2661 (1994)), oligocarbamates (Cho et al., Science, 261:1303 (1993)), peptidyl phosphonates (Campbell et al., J. Org. Chem., 59:658 (1994)), nucleic acid libraries (Ausubel, Berger, and Sambrook, all supra), peptide nucleic acid libraries (U.S. Pat. No. 5,539,083), antibody libraries (Vaughn et al., Nature Biotechnology, 14(3):309-14 (1996) and PCT/US96/10287), carbohydrate libraries (Liang et al., Science, 274:1520-22 (1996) and U.S. Pat. No. 5,593,853), small organic molecule libraries (benzodiazepines, Baum, C&EN, January 18, page 33 (1993); thiazolidinones and metathiazanones, U.S. Pat. No. 5,549,974; pynrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS (Advanced Chem Tech, Louisville Ky.), Symphony (Rainin, Woburn, Mass.), 433A (Applied Biosystems, Foster City, Calif.), 9050 Plus (Millipore, Bedford, Mass.)). In addition, numerous combinatorial libraries are themselves commercially available (see, e.g., ComGenex, Princeton, N.J.; Tripos, Inc., St. Louis, Mo.; 3D Pharmaceuticals, Exton, Pa.; Martek Biosciences; Columbia, Md.; etc.).

In one aspect of the invention, the T1R modulators can be used in any food product, confectionery, pharmaceutical composition, or ingredient thereof to thereby modulate the taste of the product, composition, or ingredient in a desired manner. For instance, T1R modulators that elicit sweet or umami taste sensation can be added to provide an improved sweet or umami taste to a product or composition, while T1R modulators which enhance sweet or umami taste sensations can be added to enhance the sweet or umami taste of another compound in a composition such as a food or beverage product or composition. Also, the invention provides means of identifying sweet or umami compounds and enhancers found in foods, beverages and medicinals and producing taste improved foods, beverages and medicinals lacking or having a reduced quantity thereof.

Use of Compounds Identified by the Invention

Compounds identified according to the invention may be added to foods, beverages or medicinal compositions to modulate sweet or umami taste.

As noted previously, preferably, the taste modulatory properties of compounds identified in the subject cell-based assays will be confirmed in taste tests, e.g., human taste tests.

Kits

The subject chimeric T1R genes and their homologs are useful tools for identifying taste receptor cells, for forensics and paternity determinations, and for examining taste transduction. T1R family member-specific reagents that specifically hybridize to T1R nucleic acids, such as T1R probes and primers, and T1R specific reagents that specifically bind to a T1R protein, e.g., T1R antibodies are used to examine taste cell expression and taste transduction regulation.

Nucleic acid assays for the presence of DNA and RNA for a T1R family member in a sample include numerous techniques are known to those skilled in the art, such as southern analysis, northern analysis, dot blots, RNase protection, S1 analysis, amplification techniques such as PCR, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., Biotechniques, 4:230250 (1986); Haase et al., Methods in Virology, vol. VII, 189-226 (1984); and Names et al., eds., Nucleic Acid Hybridization: A Practical Approach (1987). In addition, a T1R protein can be detected with the various immunoassay techniques described above. The test sample is typically compared to both a positive control (e.g., a sample expressing a recombinant T1R protein) and a negative control.

The present invention also provides for kits for screening for modulators of T1R family members. Such kits can be prepared from readily available materials and reagents. For example, such kits can comprise any one or more of the following materials: T1R nucleic acids or proteins, reaction tubes, and instructions for testing T1R activity. Optionally, the kit contains a functional T1R polypeptide. A wide variety of kits and components can be prepared according to the present invention, depending upon the intended user of the kit and the particular needs of the user.

Having now generally described the invention, the same will be more readily understood by reference to the following examples, which are provided by way of illustration and are not intended as limiting. It is understood that various modifications and changes can be made to the herein disclosed exemplary embodiments without departing from the spirit and scope of the invention.

EXAMPLE 1

Nucleic acid sequences encoding the hybrid hT1R2-1 nucleic acid sequence contained in SEQ ID NO:1 and the chimeric umami-sweet hT1R1-2 nucleic acid sequence contained in SEQ ID NO. 3 were constructed. The first hT1R2-1 sequence contains the extracellular domains of hT1R2 and the transmembrane domains of hT1R1 and the second sequence contains the extracellular domains of hT1R1 and the transmembrane domains of hT1R2. HEK-293 cell lines were created which stably produce these hybrid taste receptors Particularly, a stable HEK-293 cell line that stably constitutively expresses the chimeric hT1R2-1 sequence, hT1R3, and a chimeric G protein G16-t25 was produced which co-expresses hT1R2-1, hT1R3, and this chimeric G protein. Additionally, a stable HEK-293 cell line was constructed that stably constitutively expresses chimeric hT1R1-2, rT1R3, and another chimeric G protein G16g44 which comprises the N-terminal residues of G16 and the last 44 carboxy residues substituted with the corresponding 44 residues of gustducin. These stable HEK-293 cell lines were used in assays for sweet and umami ligands and enhancers as described in the following examples.

EXAMPLE 2

Figure 7:
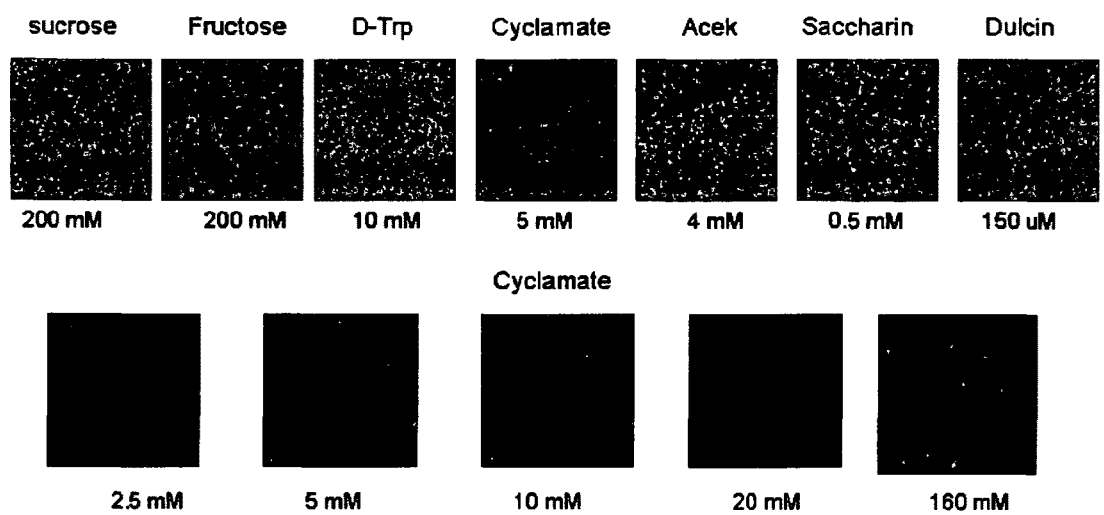
FIG. 7 contains the results of calcium imaging experiments using HEK-293 cells that express the chimeric hT1R2-1 receptor in FIG. 1 that show that this chimeric taste receptor responds to all sweeteners tested (sucrose, fructose, D-Trp, Acek, Dulcin), except for cyclamate.

The stable hT1R2-1 cell line in example 1 was screened against a number of sweet ligands at the concentrations shown in FIG. 7 and the effect on intracellular calcium and hT1R2-1 receptor activity detected by fluorimetric imaging. These assays showed that all of the sweet compounds tested activated the chimeric hT1R2-1 receptor at the tested concentrations with the exception of cyclamate. The effective concentrations (EC50s) of specific sweet compounds aspartame, D-Trp, sucrose, fructose and cyclamate to hT1R2-1/hT1R3 was also compared to the EC50s of these same compounds when used to activate the wild-type sweet receptor hT1R2/hT1R3. These results are contained in FIG. 8.

EXAMPLE 3

Figure 9:
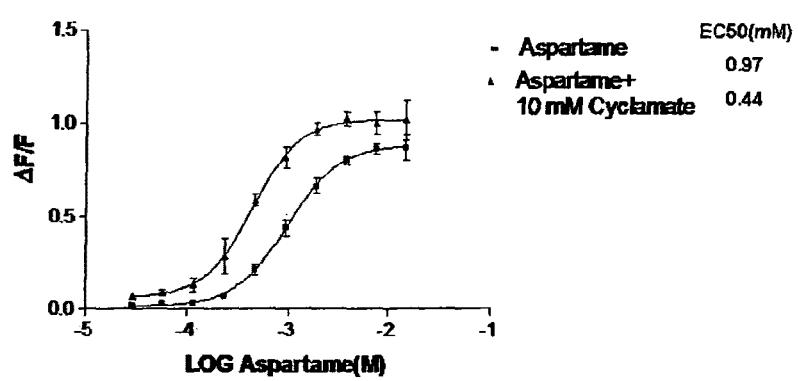
FIG. 9 contains the results of an experiment that shows that cyclamate enhances the aspartame response in a HEK-293 cell line that stably expresses the subject chimeric hT1R2-1 an unmodified hT1R3 sequence.
Figure 10:
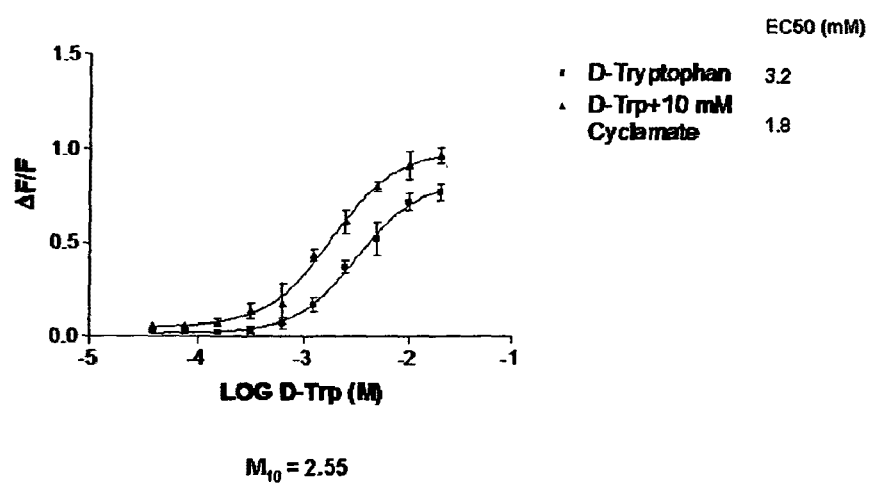
FIG. 10 contains an experiment that shows that cyclamate enhances the D-tryptophan response in a stable HEK-293 cell line that expresses hT1R2-1 chimeric taste receptor and an unmodified hT1R3 sequence.
Figure 11:
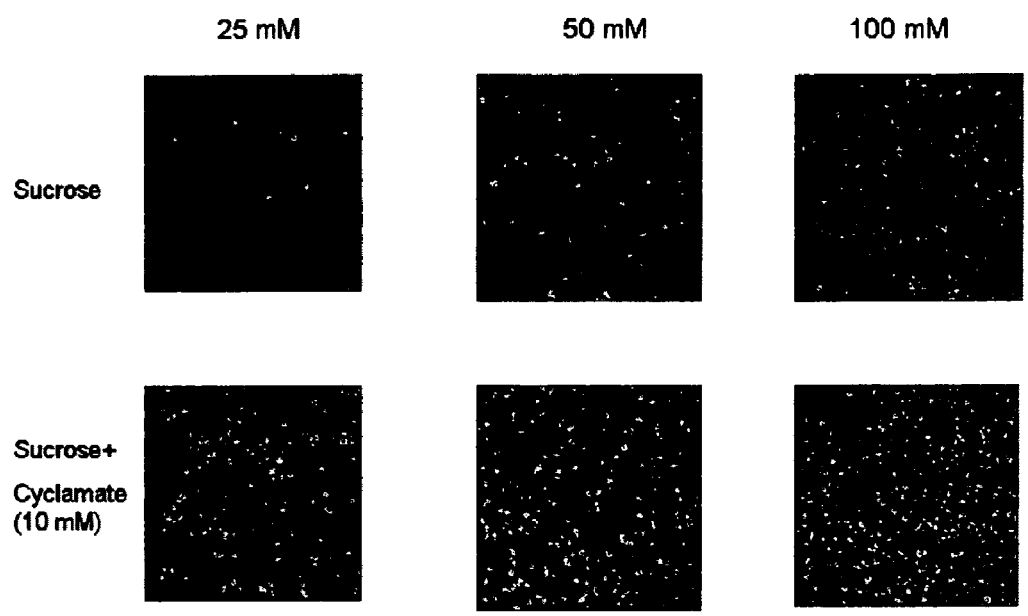
FIG. 11 contains an experiment that shows that cyclamate enhances the sucrose response in a stable cell line that expresses the subject hT1R2-1 chimeric taste receptor and an unmodified hT1R3 sequence.
Figure 12:
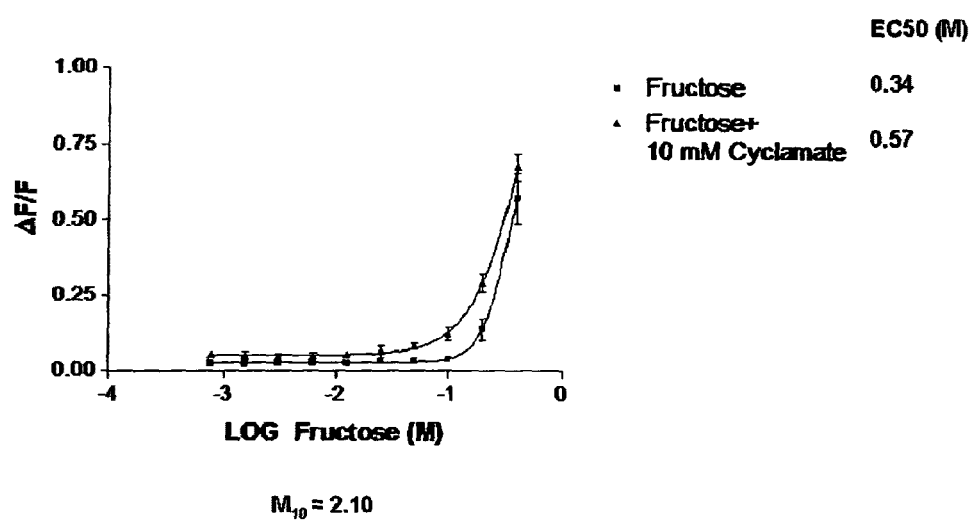
FIG. 12 contains an experiment that shows that cyclamate enhances the fructose response in a stable HEK-293 cell line that expresses the subject chimeric receptor hT1R2-1 and an unmodified hT1R3 sequence.

An assay was conducted to determine the effect of cyclamate on the activation of the chimeric hT1R2-1 taste receptor by aspartame. As shown in FIG. 9 the addition of cyclamate enhanced aspartame responses in the hT1R2-1 stable cell line. As shown in the FIG. 9 the EC50 for aspartame was 0.97 in the absence of cyclamate and 0.44 in the presence of 10 mM cyclamate. Additionally, as shown by the experimental results in FIGS. 10-12 respectively, cyclamate also enhanced D-tryptophan, sucrose and fructose activation of hT1R2-1.

EXAMPLE 4

Figure 14:
FIG. 14 contains an experiment showing that a proprietary umami ligand agonist compound '807 enhances the aspartame response in a stable HEK-293 cell line expressing hT1R2-1 and hT1R3.

Assays were also conducted to assess the effect of cyclamate on the activation of hT1R2-1 (SEQ ID NO:2) by a proprietary umami ligand referred to as '807. As shown in FIG. 13 cyclamate enhanced '807 activity. The EC50 for the '807 compound in the absence of cyclamate was 0.42 and in the presence of 5 mM cyclamate was 0.31. Also, as shown in FIG. 14 the '807 compound enhanced the activation response of hT1R2-1 to aspartame.

EXAMPLE 5

Figure 15:
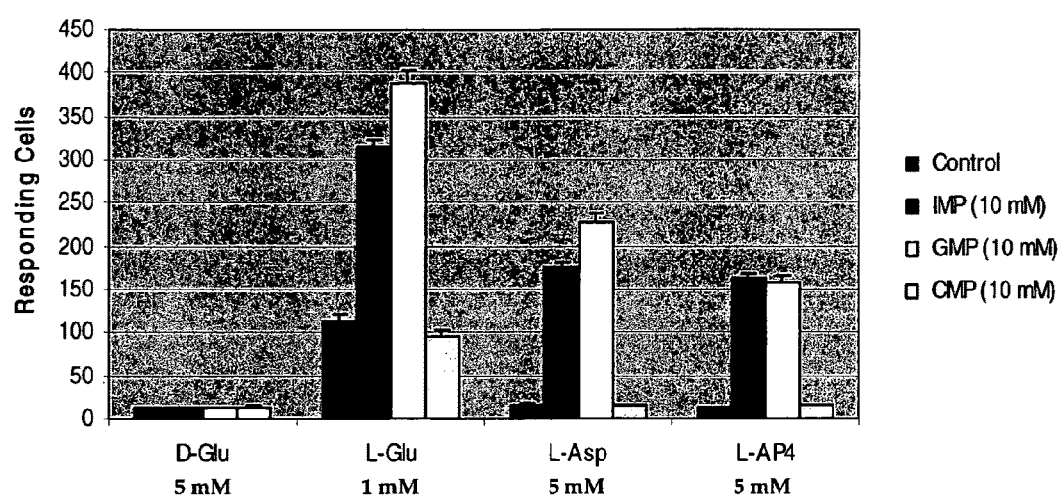
FIG. 15 contains an experiment that shows the responses of stable HEK-293 cell line that expresses the chimeric receptor hT1R1-2 (SEQ ID NO:3) and the rT1R3 receptor and shows that this chimeric receptor responds to the umami ligands L-Glu, L-Asp, and L-AP4 and that the responses were enhanced by the presence of IMP or GMP.
Figure 16:
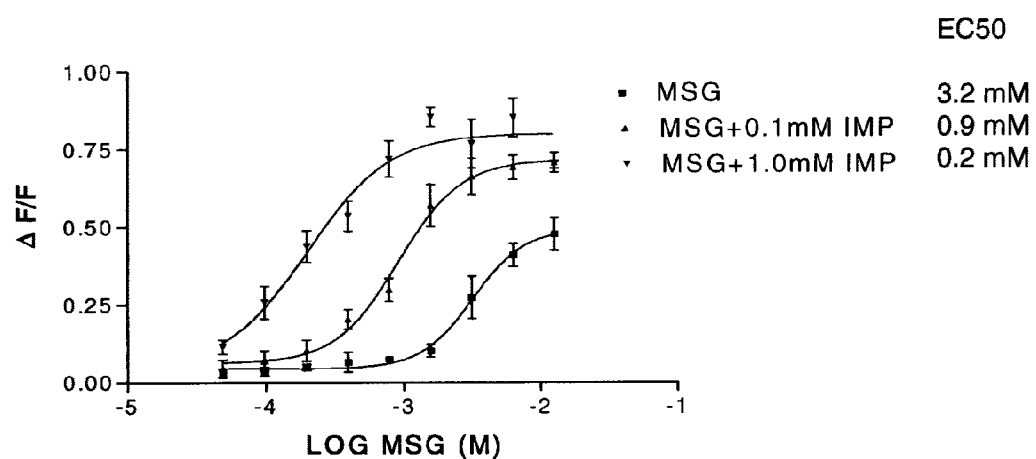
FIG. 16 shows that the activation of the chimeric hT1R1-2/rT1R3 receptor according to the invention by MSG is enhanced by IMP.

The response of chimeric umami-sweet receptor hT1R1-2 (SEQ ID NO:4) in the stable cell line co-expressing hT1R1-2 and rT1R3 to various umami ligands (L-Glu, L-Asp, and L-AP4) and to D-Glu was also assayed in the presence and absence of IMP, GMP and CMP as shown in FIG. 15. The tested umami ligands were found to activate the chimeric umami-sweet receptor. Also as shown in FIG. 16 experiments were further conducted to assess the effect of IMP on the MSG induced activation of hT1R1-2 (SEQ ID NO:4). As shown by the experimental results therein the IMP compound acted as an enhancer based on the EC50 values therein in the presence and absence of IMP.

---

What is claimed:

1. An assay for identifying putative taste modulatory compounds which comprises (i) contacting a chimeric T1R receptor polypeptide with a putative taste modulatory compound, wherein said chimeric receptor polypeptide which comprises the entire extracellular domain of a first T1R which is selected from the group consisting of human T1R1 and human T1R2 or a variant thereof possessing at least 90% sequence identity therewith and the entirety of the transmembrane domains of a second (different) human T1R relative to the first T1R which is also selected from the group consisting of human T1R1 and T1R2 or a variant thereof possessing at least 90% sequence identity therewith, wherein said chimeric receptor polypeptide alone or in association with another T1R polypeptide responds to umami or sweet taste ligands and wherein all of the remaining residues of said chimeric receptor polypeptide as a whole possess at least 90% sequence identity to all of the corresponding residues of an endogenous (unmodified) T1R polypeptide and (ii) determining whether said compound specifically binds or modulates the activity of said chimeric receptor polypeptide.

2. The assay of claim 1 wherein said second T1R is human T1R1.

3. The assay of claim 1 wherein said second T1R is human T1R2.

4. The assay of claim 1 wherein said variant extracellular and/or transmembrane domains in said chimeric receptor polypeptide possess at least 95% sequence identity to the corresponding native extracellular and/or transmembrane domains.

5. The assay of claim 4 wherein said transmembrane domains are selected from native human T1R1 or T1R2 transmembrane domains and/or said extracellular domain is selected from native human T1R1 or T1R2 extracellular domain.

6. The assay of claim 1 which uses as the chimeric receptor polypeptide the hT1R2-1 polypeptide in SEQ ID NO:2.

7. The assay of claim 1 which uses a cell that expresses said chimeric receptor polypeptide.

8. The assay of claim 7 wherein chimeric receptor polypeptide is encoded by SEQ ID NO:1 or a codon degenerate.

9. The assay of claim 7 wherein the cell is selected from a bacterial cell, yeast cell, mammalian cell, oocyte, amphibian cell, avian cell and an insect cell.

10. The assay of claim 7 wherein the cell additionally expresses a G protein selected from the group consisting of a promiscuous G protein, Gq protein, transducin, Gi protein, gustducin, transducin and chimeras thereof.

11. The assay of claim 7 wherein the cell additionally expresses a T1R3 sequence.

12. The assay of claim 1 wherein a positive compound is further evaluated in human or animal taste tests to confirm its effect on taste.

13. The assay of claim 1 which comprises assaying the effect of said compound on the activation of said chimeric taste receptor by another compound in order to detect whether it functions as an enhancer or blocker.

14. The assay of claim 13 wherein said another compound is a sweet ligand.

15. The assay of claim 13 wherein said another compound is a umami ligand.

16. The assay of claim 13 wherein said chimeric receptor polypeptide is preincubated with the putative taste modulator prior to contacting the chimeric taste receptor with a known activator of a T1R taste receptor.

17. The assay of claim 13 wherein chimeric taste receptor is preincubated with a known activator of a T1R taste receptor before assaying the effect of the putative taste modulatory compound.

18. The assay of claim 17 wherein said activator is a sweet ligand.

19. The assay of claim 18 wherein said sweet ligand is a natural sweetener or artificial sweetener.

20. The assay of claim 1 wherein the chimeric receptor polypeptide is contained on a cell membrane.

21. The assay of claim 1 which is a fluorimetric assay.

22. The assay of claim 1 which is an electrophysiological assay.

23. The assay of claim 1 which is a binding assay.

24. The assay of claim 1 wherein the chimeric receptor polypeptide is directly or indirectly covalently or non-covalently attached to a solid phase.

25. The assay of claim 7 which detects the effect of said putative taste modulatory compound on an intracellular ion in said cell.

26. The assay of claim 25 wherein said ion is calcium.

27. The assay of claim 25 wherein said ion is detected using a membrane-sensitive dye or a voltage sensitive dye.

28. The assay of claim 27 wherein the readout is fluorimetric.

29. The assay of claim 25 which detects the effect of said putative taste modulatory compound on ion polarization.

30. The assay of claim 7 which detects the effect of said compound on second messenger levels.

31. The assay of claim 30 wherein the second messenger is IP3.

32. The assay of claim 7 which detects the effect of said putative taste modulatory compound on intracellular cyclic nucleotides.

33. The assay of claim 32 wherein said nucleotides are cGMP or cAMP.

34. The assay of claim 28 which uses fluorimetric imaging.

35. The assay of claim 7 which detects the effect of said compound on G protein binding to GTPγS.

36. The assay of claim 1 which is used to detect umami enhancers.

37. The assay of claim 1 which is used to detect sweet enhancers.

* * * * *